United States Patent
Crowe et al.

(10) Patent No.: US 10,633,438 B2
(45) Date of Patent: Apr. 28, 2020

(54) POLYPEPTIDES

(71) Applicant: VHsquared Limited, Babraham, Cambridge (GB)

(72) Inventors: Scott Crowe, Cambridge (GB); Mike West, Cambridge (GB); Kevin Roberts, Cambridge (GB); Tim Carlton, Cambridge (GB); Luana Maggiore, Cambridge (GB); Marion Cubitt, Cambridge (GB); Keith Ray, Cambridge (GB)

(73) Assignee: VHsquared Limited, Cambridge, MA (US)

( * ) Notice: Subject to any disclaimer, the term of this patent is extended or adjusted under 35 U.S.C. 154(b) by 0 days.

(21) Appl. No.: 15/273,353

(22) Filed: Sep. 22, 2016

(65) Prior Publication Data

US 2017/0002069 A1 Jan. 5, 2017

Related U.S. Application Data

(63) Continuation of application No. PCT/EP2016/057021, filed on Mar. 31, 2016.

(30) Foreign Application Priority Data

Mar. 31, 2015 (EP) .................................. 15162112

(51) Int. Cl.
| | |
|---|---|
| C07K 16/24 | (2006.01) |
| A61K 39/395 | (2006.01) |
| A61K 45/06 | (2006.01) |
| A61K 31/713 | (2006.01) |
| A61K 9/19 | (2006.01) |
| A61K 31/606 | (2006.01) |
| A61K 9/00 | (2006.01) |
| A61K 31/7088 | (2006.01) |
| A61K 38/00 | (2006.01) |
| A61K 39/00 | (2006.01) |

(52) U.S. Cl.
CPC .......... C07K 16/241 (2013.01); A61K 9/0014 (2013.01); A61K 9/19 (2013.01); A61K 31/606 (2013.01); A61K 31/7088 (2013.01); A61K 31/713 (2013.01); A61K 38/00 (2013.01); A61K 45/06 (2013.01); *A61K 2039/505* (2013.01); *A61K 2039/542* (2013.01); *C07K 2317/22* (2013.01); *C07K 2317/30* (2013.01); *C07K 2317/33* (2013.01); *C07K 2317/54* (2013.01); *C07K 2317/55* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01)

(58) Field of Classification Search
CPC ..................... C07K 2317/22; C07K 2317/569
See application file for complete search history.

(56) References Cited

U.S. PATENT DOCUMENTS

| | | | |
|---|---|---|---|
| 8,399,188 B2 | 3/2013 | Zhao et al. | |
| 9,080,157 B2 | 7/2015 | Convents et al. | |
| 9,527,925 B2 | 12/2016 | Gschwind et al. | |
| 2006/0034833 A1 | 2/2006 | Beirnaert | 424/133.1 |
| 2006/0034845 A1 | 2/2006 | Silence et al. | 424/145.1 |
| 2007/0020267 A1 | 1/2007 | Fuh et al. | |
| 2007/0042399 A1 | 2/2007 | Wright et al. | |
| 2007/0077249 A1* | 4/2007 | Silence | C07K 16/18 424/145.1 |
| 2007/0178082 A1 | 8/2007 | Silence et al. | 424/131.1 |
| 2007/0237769 A1 | 10/2007 | Silence et al. | |
| 2010/0137213 A1 | 6/2010 | Fernandez et al. | 514/12 |
| 2011/0028695 A1 | 2/2011 | Revets et al. | |
| 2011/0229476 A1 | 9/2011 | Liu et al. | |
| 2014/0044730 A1 | 2/2014 | Yancopoulos et al. | |
| 2014/0186365 A1 | 7/2014 | Robinson et al. | |
| 2014/0294826 A1 | 10/2014 | Shoemaker | |
| 2015/0017183 A1 | 1/2015 | Seidah et al. | |
| 2015/0147318 A1 | 5/2015 | Bergeron et al. | |
| 2015/0337035 A1 | 11/2015 | Anderson et al. | |
| 2016/0264659 A1 | 9/2016 | Heavner et al. | |
| 2017/0002069 A1 | 1/2017 | Crowe et al. | |
| 2017/0022271 A1 | 1/2017 | Hoffman et al. | |
| 2018/0009881 A1 | 1/2018 | Crowe et al. | |
| 2018/0037639 A1 | 2/2018 | Crowe et al. | |
| 2018/0100008 A1 | 4/2018 | Crowe et al. | |

(Continued)

FOREIGN PATENT DOCUMENTS

| | | |
|---|---|---|
| WO | WO 91/02078 | 2/1991 |
| WO | WO 92/01047 | 1/1992 |

(Continued)

OTHER PUBLICATIONS

Paul, Fundamental Immunology, 3rd Edition, pp. 292-295 (Year: 1993).*
Rudikoff et al., Proc. Natl. Acad. Sci. USA, 79(6), pp. 1979-1983. (Year: 1982).*
Zabetakis et al., PLOS One, 8(10), pp. 1-7 (Year: 2013).*
Vu et al., Mol. Immunol., 34(16-17): 1121-1131. (Year: 1997).*
Kamm et al., "Practical Application of Anti-TNF Therapy for Luminal Crohn's Disease," Inflammatory Bowel Diseases, vol. 17, No. 11, pp. 2366-2391, Nov. 2011.
Yan et al., "Construction of a synthetic phage-displayed Nanobody library with CDR3 regions randomized by trinucleotide cassettes for diagnostic applications," Journal of Translational Medicine, pp. 1-12, 2014.

(Continued)

*Primary Examiner* — Hong Sang
(74) *Attorney, Agent, or Firm* — Nutter McClennen & Fish LLP

(57) ABSTRACT

There is provided inter alia a polypeptide comprising an immunoglobulin chain variable domain which binds to TNF-alpha, wherein the immunoglobulin chain variable domain comprises three complementarity determining regions (CDR1-CDR3) and four framework regions (FR1-FR4), wherein CDR1-CDR3 and FR1-FR4 are as defined in the specification.

8 Claims, 16 Drawing Sheets

Specification includes a Sequence Listing.

(56) References Cited

U.S. PATENT DOCUMENTS

| | | |
|---|---|---|
| 2018/0100009 A1 | 4/2018 | Crowe et al. |
| 2019/0008778 A1 | 1/2019 | Crowe et al. |
| 2019/0092855 A1 | 3/2019 | Crowe et al. |
| 2019/0307891 A1 | 10/2019 | Crowe et al. |

FOREIGN PATENT DOCUMENTS

| | | | |
|---|---|---|---|
| WO | WO 94/04678 | 3/1994 | |
| WO | WO 94/25591 | 11/1994 | |
| WO | WO 96/34103 | 10/1996 | |
| WO | WO 99/23221 | 5/1999 | |
| WO | WO 2002/012502 | 2/2002 | |
| WO | WO 02/48382 | 6/2002 | |
| WO | WO 2004/009776 | 1/2004 | |
| WO | WO 2004/037205 | 5/2004 | |
| WO | WO 2004/041862 | 5/2004 | |
| WO | WO 2004/041865 | 5/2004 | |
| WO | WO 2004/041867 | 5/2004 | |
| WO | WO-2004041863 A2 * | 5/2004 | ............ C07K 16/18 |
| WO | WO 2006/122786 | 11/2006 | |
| WO | WO 2006/122787 | 11/2006 | |
| WO | WO 2007/025977 | 3/2007 | |
| WO | WO 2007/048022 | 4/2007 | |
| WO | WO 2007/070948 | 6/2007 | |
| WO | WO 2007/104529 | 9/2007 | |
| WO | WO 2008/049897 | 5/2008 | |
| WO | WO 2008/101985 | 8/2008 | |
| WO | WO 2008/124170 | 10/2008 | |
| WO | WO 2008/144753 | 11/2008 | |
| WO | WO 2008/149143 | 12/2008 | |
| WO | WO 2009/021754 | 2/2009 | |
| WO | WO 2009/046168 | 4/2009 | |
| WO | 2009147248 A2 | 12/2009 | |
| WO | WO 2010/020811 | 2/2010 | |
| WO | WO 2010/045506 | 4/2010 | |
| WO | WO 2010/056550 | 5/2010 | |
| WO | WO 2010/077422 | 7/2010 | |
| WO | WO 2011/083175 | 7/2011 | |
| WO | WO 2011/135040 | 11/2011 | |
| WO | WO 2011/139629 | 11/2011 | |
| WO | WO 2012/007880 | 1/2012 | |
| WO | 2012055030 A1 | 5/2012 | |
| WO | WO 2012/078878 | 6/2012 | |
| WO | 2012131053 A1 | 10/2012 | |
| WO | WO 2012/175741 | 12/2012 | |
| WO | WO 2013/024059 | 2/2013 | |
| WO | WO 2013/058833 | 4/2013 | |
| WO | WO 2013/064701 | 5/2013 | |
| WO | 2013087857 A2 | 6/2013 | |
| WO | 2013087874 A1 | 6/2013 | |
| WO | 2013091103 A1 | 6/2013 | |
| WO | WO 2015/065987 | 5/2015 | |
| WO | 2015100409 A2 | 7/2015 | |
| WO | WO 2015/144852 | 10/2015 | |
| WO | WO 2016/065323 | 4/2016 | |
| WO | WO 2016/103093 | 6/2016 | |
| WO | WO 2016/162537 | 10/2016 | |
| WO | WO 2016/202411 | 12/2016 | |
| WO | WO 2016/202414 | 12/2016 | |
| WO | WO 2016/202415 | 12/2016 | |

OTHER PUBLICATIONS

International Searching Authority, ISR pertaining to International Application No. PCT/EP2016/057021, 8 pages, dated Aug. 8, 2016.
Harmsen et al., "Selection and optimization of proteolytically stable llama single-domain antibody fragments for oral immunotherapy," Applied Microbiology and Biotechnology, 72(3), pp. 544-551, 2006.
Hussack et al., "Engineered Single-Domain Antobodies with High Protease Resistance and Thermal Stability," PLoS One, 6(11), 15 pages, Nov. 2011.
Liu et al., "Targeting TNF-α with a tetravalent mini-antibody TNF-TeAb," Biochemical Journal, 406(2), pp. 237-246, 2007.
Mølhøj et al., "CD19-/CD3-bispecific antibody of the BiTE class is far superior to tandem diabody with respect to redirected tumor cell lysis," Molecular Immunology, 44(8), pp. 1935-1943, 2007.
Database Uniprot accession No. B5H131, http://www.uniprot.org/uniprot/B5H131, 2 pages, 2008.
Kim et al., "A Dual Target-directed Agent against Interleukin-6 Receptor and Tumor Necrosis Factor α ameliorates experimental arthritis", Scientific Reports, pp. 1-12, Apr. 2015.
Baumgart et al., "Crohn's disease," The Lancet, 380 (9853), pp. 1590-1605, 2012.
Biancheri et al., "Differenctial cleavage of anti-tumor necrosis factor-alpha agents by matrix metalloproteinase (MMP)-10 and MMP-12 in inflammatory bowel disease," ECCO, Abstract, 1 page, Dublin, 2011.
Blättler et al., "New Heterobifunctional Protein Cross-Linking Reagent That Forms an Acid-Labile Link," Biochemistry, vol. 24, pp. 1517-1524, 1985.
Chomczynski et al., "Single-Step Method of RNA Isolation by Acid Guanidinium Thiocyanate-Phenol-Chloroform Extraction," Analytical Biochemistry, vol. 162, pp. 156-159, 1987.
Coppieters et al., "Formatted Anti-Tumor Necrosis Factor α VHH Proteins Derived from Camelids Show Superior Potency and Targeting to Inflamed Joints in a Murine Model of Collagen-Induced Arthritis," Arthritis & Rheumatism, vol. 54, No. 6, pp. 1856-1866, Jun. 2006.
Danese, "New Therapies for inflammatory bowel disease: from the bench to the bedside," Gut 2012 61: 918-932 originally published online Nov. 23, 2011.
Faisst et al., "Isolation of a Fully Infectious Variant of Parvovirus H-1 Supplanting the Standard Strain in Human Cells," Journal of Virology, vol. 69, No. 7, pp. 4538-4543, Jul. 1995.
Frenken et al., "Isolation of antigen specific Llama $V_{HH}$ antibody fragments and their high level secretion by Saccharomyces cerevisiae," Journal of Biotechnology, vol. 78, pp. 11-21, 2000.
Ghahroudi et al., "Selection and identification of single domain antibody fragments from camel heavy-chain antibodies," FEBS Letters, vol. 414, pp. 521-526, 1997.
Griffiths et al., "Shark Variable New Antigen Receptor ($V_{NAR}$) Single Domain Antibody Fragments: Stability and Diagnostic Applications," Antibodies, vol. 2, pp. 66-81, 2013.
Grundström et al., "Oligonucleotide-directed mutagenesis by microscale 'shot-gun' gene synthesis," Nucleic Acids Research, vol. 13, No. 9, pp. 3305-3316, 1985.
Hamers-Casterman et al., "Naturally occurring antibodies devoid of light chains," Nature, vol. 363, pp. 446-448, Jun. 3, 1993.
Harmsen et al., "Effect of pmr1 disruption and different signal sequences on the intracellular processing and secretion of Cyamopsis tetragonoloba α-galactosidase by Saccharomyces cerevisiae," Gene, vol. 125, pp. 115-123, 1993.
Harmsen et al., "Properties, production, and applications of camelid single-domain antibody fragments," Appl Microbial Biotechnol, vol. 77, pp. 13-22, 2007.
Hendrickson et al., "Clinical Aspects and Pathophysiology of Inflammatory Bowel Disease," Clinical Microbiology Reviews, vol. 15, No. 1, pp. 79-94, Jan. 2002.
Hoogenboom et al., "Multi-subunit proteins on the surface of filamentous phage: methodologies for displaying antibody (Fab) heavy and light chains," Nucleic Acids Research, vol. 19, No. 15, pp. 4133-4137. 1991.
Huse et al., "Generation of a Large Combinatorial Library of the Immunoglobulin Repertoire in Phage Lambda," Science, vol. 246, pp. 1275-1281, Dec. 8, 1989.
Köhler et al., "Continuous cultures of fused cells secreting antibody of predefined specificity," Nature, vol. 256, pp. 495-497, Aug. 17, 1975.
Ling et al., "Approaches to DNA Mutagenesis: An Overview," Analytical Biochemistry, vol. 254, pp. 157-178, 1997.
McCoy et al., "Neutralisation of HIV-1 cell-cell spread by human and llama antibodies," Retrovirology vol. 11, No. 83, pp. 1-15, 2014.
Merchlinsky et al., "Construction of an Infectious Molecular Clone of the Autonomous Parvovirus Minute Virus of Mice," Journal of Virology, vol. 47, No. 1, pp. 227-232, Jul. 1983.

(56) References Cited

OTHER PUBLICATIONS

Miethe et al., "Production of Single Chain Fragment Variable (scFv) Antibodies in *Escherichia coli* Using the LEX™ Bioreactor," *Journal of Biotechnology*, vol. 163, pp. 105-111, Aug. 2012.

Muyldermans et al., "Sequence and Structure of $V_H$ domain from naturally occurring camel heavy chain inununoglobulins lacking light chains," *Protein Engineering*, vol. 7, No. 9, pp. 1129-1135, 1994.

Muyldermans, "Nanobodies: Natural Single-Domain Antibodies," *Annu. Rev. Biochem.*, vol. 82, pp. 775-797, 2013.

Nambiar et al., "Total Synthesis and Cloning of a Gene Coding for the Bionuclease S Protein," *Science*, vol. 223, pp. 1299-1301, 1984.

Nelson et al., "Nonoclonal antibodies," *Molecular Pathology*, vol. 53, pp. 111-117, 2000.

Nguyen et al., "Functional Heavy-chain Antibodies in Camelidae," *Advances in Immunology*, vol. 79, 37 pages.

Ortonne, "Recent developments in the understanding of the pathogenesis of psoriasis," *British Journal of Dermatology*, vol. 140 (Suppl. 54), pp. 1-7, 1999.

Padlan, "Anatomy of the Antibody Molecule," *Molecular Immunology*, vol. 31, No. 3, pp. 169-217, 1994.

Roux et al., "Structural analysis of the nurse shark (new) antigen receptor (NAR): Molecular convergence of NAR and unusual mammalian immunoglobulins," *Proc. Natl. Acad. Sci. USA*, vol. 95, pp. 11804-11809, Sep. 1998.

Sakmar et al., "Total synthesis and expression of a gene for the α-subunit of bovine rod outer segment guanine nucleotide-binding protein (transducin)," *Nucleic Acids Research*, vol. 16, No. 14, pp. 6361-6372, 1988.

Shealy et al., "Characterization of golimumab, a human monoclonal antibody specific for human tumor necrosis factor," mAbs 2:4, pp. 428-439, 2010.

Siontorou, "Nanobodies as novel agents for disease diagnoisis and therapy," *International Journal of Medicine*, vol. 8, pp. 4215-4227, 2013.

Skerra et al., "Assembly of a Functional Immunoglobulin $F_V$ Fragment in *Escherichia coli*," *Science*, vol. 240, pp. 1038-1041, 1988.

Tanha et al., "Selection by phage display of llama conventional $V_H$ fragments with heavy chain antibody $V_H$H properties," *Journal of Immunological Methods*, vol. 263, pp. 97-109, 2002.

Thomassen et al., "Large-scale production of $V_{HH}$ antibody fragments by *Saccharomyces cerevisiae*," *Enzyme and Microbial Technology*, vol. 30, pp. 273-278, 2002.

Ungar et al., "Optimizing Anti-TNF-α Therapy: Serum Levels of Infliximab and Adalimumab Are Associated With Mucosal Healing in Patients with Inflammatory Bowel Diseases," *Clinical Gastroenterology and Hepatology*, vol. 14, pp. 550-557, 2016.

Van Deventer, "Anti-TNF antibody treatment of Crohn's disease," *Ann Rheum Dis*, 58 (Suppl I) pp. I114-I120, 1999.

Van Schie et al., "The antibody response against human and chimeric anti-TNF therapeutic antibodies primarily targets the TNF binding region," *Ann Rheum Dis*, vol. 74, pp. 311-314, 2015.

Vandenbroucke et al., "Orally administered L. lactis secreting an anti-TNF Nanobody demonstrate efficacy in chronic colitis," *Mucosal Immunology*, vol. 3, No. 1, pp. 49-56, Jan. 2010.

Verma et al., "Modified Oligonucleotides: Synthesis and Strategy for Users," *Annu. Rev. Biochem.*, vol. 67, pp. 99-134, 1998.

Ward et al., "Binding activities of a repertoire of single immunoglobulin variable domains secreted from *Escherichia coli*," *Nature*, vol. 341, pp. 544-546, Oct. 12, 1989.

Wells et al., "Cassette mutagenesis: an efficient method for generation of multiple mutations at defined sites," *Gene*, vol. 34, pp. 315-323, 1985.

Crowe, S., et al., "Gastrointestinal Stability and Tissue Penetration of V565: A Novel Orally Administered Anti-TNF α Vorabody™," *VHsquared*, PEGS Europe Protein and Antibody Engineering Summit, Nov. 13-17, 2017, Lisbon, Portugal, 1 page.

Crowe, S., et al., "Oral Delivery of a Novel Engineered Anti-TNF α Domain Antibody (Vorabody™) for the Treatment of Intestinal Bowel Disease," *VHsquared*, PEGS Europe Protein and Antibody Engineering Summit, Nov. 13-17, 2017, Lisbon, Portugal, 1 page.

Crowe, S., et al., "Preclinical Assessment of a Novel Anti-TNF α Vorabody™ as an Oral Therapy for Crohn's Disease," *VHsquared*, 18th International Congress of Mucosal Immunology, Jul. 19-22, 2017, Washington, DC, 1 page.

Crowe, S., et al., "Preclinical Development of a Novel, Orally-Administered Anti-Tumour Necrosis Factor Domain Antibody for the Treatment of Inflammatory Bowel Disease," Nature.com—*Scientific Reports*, 13 pages, Mar. 21, 2018.

Nurbhai, S., et al., "Measured and Modelled Data Suggest that Oral Administration of V565, A Novel Domain Antibody to TNF-alpha, Could Be Beneficial in the Treatment of IBD," *VHsquared*, 13th Congress of ECCO, Feb. 14-17, 2018, Vienna, Austria, 1 page.

Robinson, J., et al., "A Protease-Resistant Oral Domain Antibody to TNF α Delivers High Concentrations of Active Compound in Ileal Fluid of Subjects with an Ileostomy," *VHsquared*, 25th United European Gastroenterology Week, Oct. 28-Nov. 1, 2017, Barcelona, Spain, 1 page.

Wahlich, J., et al., "Oral Delivery of a Novel Domain Antibody (Vorabody™) for the Treatment of Crohn's Disease," *VHsquared*, PEGS Europe Protein and Antibody Engineering Summit, Nov. 13-17, 2017, Lisbon, Portugal, 1 page.

West, M., et al., "Predicting Intestinal Tract Luminal Concentrations After Oral Dosing of an Anti TNF α Domain Antibody Engineered for Intestinal Protease Resistance," *VHsquared*, 2017 Antibody Engineering & Therapeutics meeting, Dec. 10-14, 2017, San Diego, USA, 1 page.

Bendig, M., "Humanization of Rodent Monoclonal Antibodies by CDR Grafting," Methods: A Companion to Methods in Enzymology, vol. 8, pp. 83-93 (1995).

Colman, P.M., "Effects of Amino Acid Sequence Changes on Antibody-Antigen Interactions," Research in Immunology, vol. 145, pp. 33-36 (1994).

Deschacht, N. et al., "A Novel Promiscuous Class of Camelid Single-Domain Antibody Contributes to the Antigen-Binding Repertoire," J. Immmunol., vol. 184, pp. 5696-5704 (2010).

Giusti, A., et al. "Somatic diversificiation of S107 from an antiphosphocholine to an anti-DNA autoantibody is due to a single base change in its heavy chain variable region," Proc. Natl. Acad. Sci. USA, vol. 84, pp. 2926-2930 (May 1987).

Horwitz, A. et al., "Secretion of functional antibody and Fab fragment from yeast cells," Proc. Natl. Acad. Sci. USA, vol. 85, pp. 8678-8682 (Nov. 1988).

Hussack, G., et al., "Neutralization of Clostridium difficile Toxin A with Single-Domain Antibodies Targeting the Cell Receptor Binding Domain," J. Biol. Chem., vol. 28(11), pp. 8961-8976 (Mar. 2011).

Hussack, G., et al., "Isolation and Characterization of Clostridium difficile Toxin-Specific Single-Domain Antibodies," Methods & Protocols, vol. 911, pp. 211-239 (2012).

Hussack, G., "Single-domain Antibody Inhibitors of Clositridium difficile Toxins," Thesis submitted to the Faculty of Graduate and Postdoctoral Studies, Dept. of Biochemistry, Microbiology and Immunology, 227 pages. (Nov. 2011).

Khantasup, K. et al., "Design and Generation of Humanized Single-chain Fv Derived From Mouse Hybridoma for Potential Targeting Application," Monoclonal Antibodies in Immunodiagnosis & Immunotherapy, vol. 34(6), pp. 404-417 (2015).

Unger, M., et al., "Selection of Nanobodies that Block the Enzymatic and Cytotoxic Activities of the Binary Clostridium Difficile Toxin CDT," Scientific Reports, vol. 5(7850), pp. 1-10 (Jan. 2015).

Yu, L., et al. "Interaction between Bevacizumab and Murine VEGF-A: A Reassessment," Invest. Ophthal. & Vis. Sci., vol. 49(2), pp. 522-527 (2008).

Crowe S., et al., "Gastrointestinal Stability and Tissue Penetration of V565: a Novel Orally Administered Anti-TNFα VorabodyTM," 10th Annual Proteins and Antibodies Congress, 2017, 1 page.

Crowe S., et al., Gastrointestinal Stability and Tissue Penetration of V565: A Novel Orally Administered Anti-TNFα VorabodyTM,

(56) References Cited

OTHER PUBLICATIONS

VHsquared, EGS Europe Protein and Antibody Engineering Summit, Nov. 13-17, 2017, Lisbon, Portugal, 1 page.

* cited by examiner

Immunoglobulin chain variable domains in mouse small intestinal and human faecal digests

POLYPEPTIDES

CROSS REFERENCE

This application is a continuation of international application PCT/EP2016/057021 filed on Mar. 31, 2016 which derives priority from EP15162112.5 filed on Mar. 31, 2015, the contents of each of which are herein incorporated by reference in their entirety.

FIELD OF THE INVENTION

The present invention relates to polypeptides comprising an immunoglobulin chain variable domain (or 'variable domain') which binds to Tumour Necrosis Factor-alpha ('TNF-alpha', 'TNF-α' or 'TNF') as well as to constructs and pharmaceutical compositions comprising these polypeptides. The present invention also relates to nucleic acids encoding such polypeptides, to methods for preparing such polypeptides, to cDNA and vectors comprising nucleic acids encoding such polypeptides, to host cells expressing or capable of expressing such polypeptides and to uses of such polypeptides, pharmaceutical compositions or constructs.

BACKGROUND OF THE INVENTION

Tumour necrosis factor-alpha is a homotrimeric pro-inflammatory cytokine involved in systemic inflammation which exists in both soluble and membrane-bound forms. TNF-alpha is secreted predominantly by monocytes and macrophages but is also secreted by tumour cell lines as well as CD4+ and CD8+ peripheral blood T lymphocytes and some cultured T and B cell lines. TNF-alpha has been implicated in inflammatory diseases, autoimmune diseases, viral, bacterial and parasitic infections, malignancies, and/or neurodegenerative diseases and is a target for specific biological therapy in autoimmune/autoinflammatory diseases such as rheumatoid arthritis and Crohn's disease.

Crohn's disease, also known as Crohn syndrome and regional enteritis, is a type of inflammatory bowel disease causing a wide variety of symptoms. It primarily causes abdominal pain, diarrhea, vomiting and/or weight loss but may also cause complications outside the gastrointestinal tract (GIT) such as anaemia, skin rashes, arthritis, inflammation of the eye, tiredness, and lack of concentration (Baumgart et al 2012 *The Lancet* 380(9853):1590-605, herein incorporated by reference in its entirety). Crohn's disease is a presently incurable life-long gastrointestinal disease that is difficult to control with conventional therapies. Crohn's disease is discussed in more detail below under 'autoimmune diseases'.

A TNF-alpha inhibitor which has sufficient specificity to TNF-alpha may be an efficient prophylactic or therapeutic pharmaceutical for preventing or treating diseases such as Crohn's disease, where TNF-alpha has been implicated as a key cytokine driving the pathology observed.

Antibody-based therapeutics have significant potential as effective treatments for autoimmune disease because they have high specificity for their target and a low inherent toxicity. Methods of treating autoimmune disease by administration of an antibody which binds TNF-alpha have been described (Kamm et al 2011 *Inflamm Bowel Dis* 17:2366-91, herein incorporated by reference in its entirety).

Three anti-TNF-alpha antibodies infliximab (trade name Remicade), adalimumab (trade name Humira) and certolizumab (or 'tertolizumab pegol', both trade name Cimzia) are used clinically for the treatment of Crohn's disease; however these antibodies are generally considered to be unsuitable for administration as oral therapeutics due to their inherent instability and susceptibility to proteolytic degradation by the digestive system, inflammatory proteases present at the sites of pathology in the intestinal tract, and intestinal microflora. These agents therefore have to be administered by intravenous infusion or subcutaneous injection which requires specialist training in order to use a hypodermic syringe or needle correctly and safely. These agents also require sterile equipment, a liquid formulation of the therapeutic polypeptide, vial packing of said polypeptide in a sterile and stable form and a suitable site on the subject for entry of the needle. Subjects commonly experience psychological stress before receiving an injection and pain while receiving an injection. Long term treatment with these systemic anti-TNF-alpha antibodies carries increased risks of serious infection and cancer. Together with the high costs of production, these factors currently restrict use of these agents to patients with more severe disease.

Several small molecule anti-inflammatory and immunosuppressive drugs are also currently in clinical development for Crohn's disease (Danese 2012 *Gut* 61:918-932 and Shealy et al 2010 *mAbs* 2:428-439, herein incorporated by reference in its entirety). Although these drugs are orally administered, many will be absorbed systemically after administration and may therefore have systemic immunosuppressive actions that are unrelated to actions against the gastrointestinal tract lesions. Furthermore, as small molecules lack the specificity of antibodies the risk of significant off target side-effects remains high.

Crohn's disease is primarily a disease of the gastrointestinal tract. The production of TNF-alpha is localised to cells present within mucosal and sub-mucosal tissues and this drives chronic inflammatory processes within the gut wall and the recruitment of additional inflammatory cells that are responsible for development of the disease immunopathology (van Deventer 1999 *Ann Rheum Dis* 58(Suppl I):I114-I120). The ability to deliver an oral therapeutic agent with high selectivity for TNF-alpha, but with exposure and activity limited to the gut, may offer efficacy similar to injectable anti-TNF-alpha antibodies, combined with significant improvements in safety due to reduced systemic exposure.

WO 2004/041862, WO 2006/122786 and Coppieters et al 2006 *Arthritis & Rheumatism* 54(6):1856-1866 (herein incorporated by reference in their entirety) disclose single domain antibodies directed against TNF-alpha and related aspects. The sequence referred to in WO 2006/122786 as "TNF1", "PMP1 C2" or "SEQ ID NO: 52") is characterised further below.

Polypeptides of the present invention may, in at least some embodiments, have one or more of the following advantages compared to anti-TNF-alpha substances of the prior art:

(i) increased affinity for TNF-alpha;
(ii) increased specificity for TNF-alpha;
(iii) increased neutralising capability against TNF-alpha;
(iv) increased cross-reactivity with TNF-alpha from different species such as human and cynomolgus monkey;
(v) increased cross-reactivity with both soluble and membrane forms of TNF-alpha;
(vi) reduced immunogenicity, for example when administered to a mouse, cynomolgus monkey or human;
(vii) increased stability in the presence of proteases, for example (a) in the presence of proteases found in the small and/or large intestine and/or IBD inflammatory proteases, for example trypsin, chymotrypsin, MMP3, MMP10, MMP12, other MMPs and cathepsin and/or (b) in the presence of proteases from gut commensal microflora and/or pathogenic bacteria, actively secreted and/or released by lysis of microbial cells found in the small and/or large intestine;

(viii) increased stability to protease degradation during production (for example resistance to yeast proteases)

(ix) increased suitability for oral administration;

(x) increased suitability for local delivery to the intestinal tract and lamina propria following oral administration;

(xi) increased suitability for expression, in a heterologous host such as bacteria such as *Escherichia coli*, or a yeast belonging to the genera *Aspergillus, Saccharomyces, Kluyveromyces, Hansenula* or *Pichia*, such as *Saccharomyces cerevisiae* or *Pichia pastoris;*

(xii) suitability for, and improved properties for, use in a pharmaceutical;

(xiii) suitability for, and improved properties for, use in a functional food;

(xiv) improved tissue penetration such as penetration of inflamed colonic mucosal epithelium and submucosal tissues to access the sub mucosal lamina propria;

(xv) remain substantially active after (a) freezing and thawing and/or (b) after long term storage in lyophilised, liquid/cream format at for example 37 or 50 degrees C.;

(xvi) decreased immunogenicity in humans for example due to increased sequence similarity to human immunoglobulins;

(xvii) increased suitability for formatting in a multispecific format;

(xviii) binding to novel epitopes.

Advantages (i) to (xviii) above may potentially be realised by the polypeptides of the present invention in a monovalent format or in a multivalent format such as a bihead format (for example homobihead or heterobihead formats).

SUMMARY OF THE INVENTION

The present inventors have produced surprisingly advantageous polypeptides comprising immunoglobulin chain variable domains which bind to TNF-alpha. These polypeptides in particular benefit from surprisingly high potency. They also neutralise both the soluble and membrane forms of TNF-alpha, are capable of cross-reacting with cynomolgus monkey TNF-alpha and remain stable on exposure to trypsin, chymotrypsin and/or proteases of the small and large intestine. In one embodiment, these polypeptides have undergone further enhancement by engineering. These further enhanced polypeptides benefit from the above advantages, retain their TNF-alpha-neutralising activity during passage through the intestinal tract and further resist degradation and/or inactivation by proteases of the intestinal tract, for example, digestive, inflammatory and microbial proteases from, for example, multiple mammalian species (rodent, pig, non-human primate and human).

It may be expected that these polypeptides have particular utility in the prevention or treatment of autoimmune and or inflammatory disease such as inflammatory bowel disease (for example Crohn's disease or ulcerative colitis), or in the prevention or treatment of mucositis, particularly when administered orally.

The present invention provides a polypeptide comprising an immunoglobulin chain variable domain which binds to TNF-alpha, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 1, CDR2 comprises a sequence sharing 50% or greater sequence identity with SEQ ID NO: 2 and (a) CDR3 comprises a sequence sharing 80% or greater sequence identity with SEQ ID NO: 3 or (b) CDR3 comprises a sequence sharing 50% or greater sequence identity with SEQ ID NO: 3 and wherein the residue of CDR3 corresponding to residue number 3 of SEQ ID NO: 3 is R, D, N, C, E, Q, G, H, I, L, K, M, F, P, S, T, W, Y or V.

Also provided is a polypeptide comprising an immunoglobulin chain variable domain which binds to TNF-alpha, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 15 CDR2 comprises a sequence sharing 50% or greater sequence identity with SEQ ID NO: 16 and CDR3 comprises a sequence sharing 50% or greater sequence identity with SEQ ID NO: 17.

Also provided is a polypeptide comprising an immunoglobulin chain variable domain which binds to TNF-alpha, wherein the immunoglobulin chain variable domain comprises three complementarity determining regions (CDR1-CDR3) and four framework regions (FR1-FR4), wherein CDR3 comprises a sequence sharing 80% or greater sequence identity with SEQ ID NO: 3.

DESCRIPTION OF THE SEQUENCES

Figure 1:
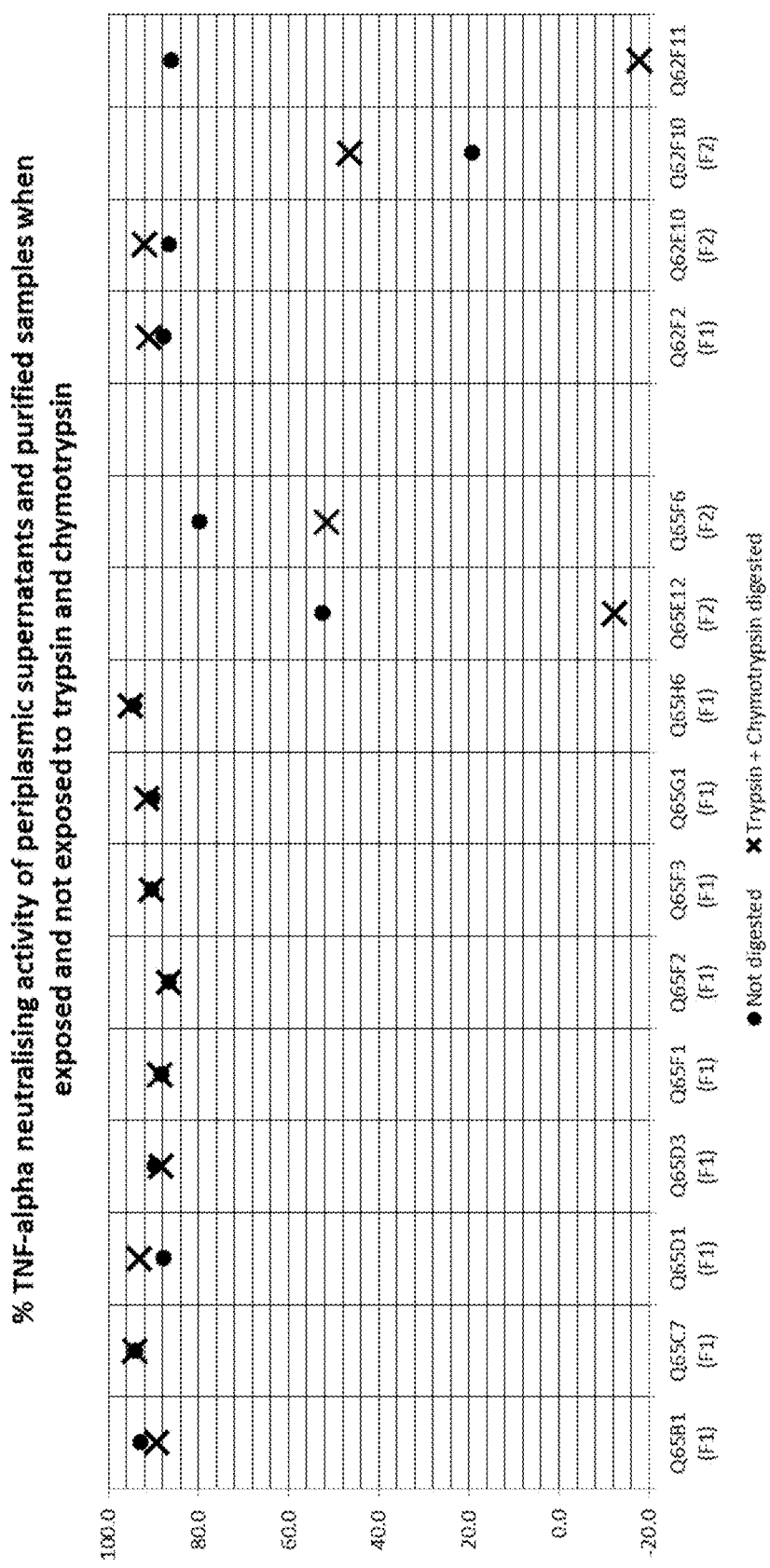
FIG. 1—% TNF-alpha neutralising activity of periplasmic supernatants and purified samples when exposed and not exposed to trypsin and chymotrypsin FIG. 2A—hs-TNF-alpha neutralization by Q65B1, Q65C7, Q62E10 and adalimumab in HEK-Nf-kB-SEAP reporter assay FIG. 2B—hs-TNF-alpha neutralization by Q65B1 and Q65D3

SEQ ID NO: 1—Polypeptide sequence of ID38F CDR1
SEQ ID NO: 2—Polypeptide sequence of ID38F CDR2
SEQ ID NO: 3—Polypeptide sequence of ID38F CDR3
SEQ ID NO: 4—Polypeptide sequence of ID38F FR1

SEQ ID NO: 5—Polypeptide sequence of ID38F FR2
SEQ ID NO: 6—Polypeptide sequence of ID38F FR3
SEQ ID NO: 7—Polypeptide sequence of ID38F FR4
SEQ ID NO: 8—Polypeptide sequence of ID38F
SEQ ID NO: 9—Polypeptide sequence of soluble human TNF-alpha (monomer)
SEQ ID NO: 10—Polypeptide sequence of membrane-bound human TNF-alpha (monomer)
SEQ ID NO: 11—Polypeptide sequence of soluble cynomolgus monkey TNF-alpha (monomer)
SEQ ID NO: 12—Polypeptide sequence of membrane-bound cynomolgus monkey TNF-alpha (monomer)
SEQ ID NO: 13—Polypeptide sequence of soluble mouse TNF-alpha (monomer)
SEQ ID NO: 14—Polypeptide sequence of membrane-bound mouse TNF-alpha (monomer)
SEQ ID NO: 15—Polypeptide sequence of Q62E10 CDR1
SEQ ID NO: 16—Polypeptide sequence of Q62E10 CDR2
SEQ ID NO: 17—Polypeptide sequence of Q62E10 CDR3
SEQ ID NO: 18—Polypeptide sequence of Q62E10 FR1
SEQ ID NO: 19—Polypeptide sequence of Q62E10 FR2
SEQ ID NO: 20—Polypeptide sequence of Q62E10 FR3
SEQ ID NO: 21—Polypeptide sequence of Q62E10 FR4
SEQ ID NO: 22—Polypeptide sequence of Q62E10
SEQ ID NO: 23—Polypeptide sequence of Q65F2
SEQ ID NO: 24—Polypeptide sequence of Q65F3
SEQ ID NO: 25—Polypeptide sequence of Q62F2
SEQ ID NO: 26—Polypeptide sequence of Q65G1
SEQ ID NO: 27—Polypeptide sequence of Q65H6
SEQ ID NO: 28—Polypeptide sequence of Q65F1
SEQ ID NO: 29—Polypeptide sequence of Q65D1
SEQ ID NO: 30—Polypeptide sequence of Q65C7
SEQ ID NO: 31—Polypeptide sequence of Q65D3
SEQ ID NO: 32—Polypeptide sequence of Q65B1
SEQ ID NO: 33—Polypeptide sequence of Q65F6
SEQ ID NO: 34—Polypeptide sequence of Q65F11
SEQ ID NO: 35—Polypeptide sequence of Q65E12
SEQ ID NO: 36—Polypeptide sequence of Q65C12
SEQ ID NO: 37—Polypeptide sequence of Q65A6
SEQ ID NO: 38—Polypeptide sequence of Q65A3
SEQ ID NO: 39—Polypeptide sequence of Q62F10
SEQ ID NO: 40—Polypeptide sequence of Q62F11
SEQ ID NO: 41—Polypeptide sequence of ID7F-EV
SEQ ID NO: 42—Polypeptide sequence of ID8F-EV
SEQ ID NO: 43—Polypeptide sequence of ID9F-EV
SEQ ID NO: 44—Polypeptide sequence of ID13F-EV
SEQ ID NO: 45—Polypeptide sequence of ID14F-EV
SEQ ID NO: 46—Polypeptide sequence of ID15F-EV
SEQ ID NO: 47—Polypeptide sequence of ID22F
SEQ ID NO: 48—Polypeptide sequence of ID23F
SEQ ID NO: 49—Polypeptide sequence of ID24F
SEQ ID NO: 50—Polypeptide sequence of ID25F
SEQ ID NO: 51—Polypeptide sequence of ID26F
SEQ ID NO: 52—Polypeptide sequence of ID27F
SEQ ID NO: 53—Polypeptide sequence of ID28F
SEQ ID NO: 54—Polypeptide sequence of ID29F
SEQ ID NO: 55—Polypeptide sequence of Q62E10-DVQLV
SEQ ID NO: 56—Polypeptide sequence of ID34F
SEQ ID NO: 57—Polypeptide sequence of ID37F
SEQ ID NO: 58—Polynucleotide sequence of 3' Primer with Spe site
SEQ ID NO: 59—Polypeptide sequence of Q65F1 CDR1
SEQ ID NO: 60—Polypeptide sequence of Q65D1 CDR1
SEQ ID NO: 61—Polypeptide sequence of ID27F CDR2
SEQ ID NO: 62—Polypeptide sequence of ID28F CDR2
SEQ ID NO: 63—Polypeptide sequence of Q65F2 CDR2
SEQ ID NO: 64—Polypeptide sequence of Q65F3 CDR2
SEQ ID NO: 65—Polypeptide sequence of Q62F2 CDR2
SEQ ID NO: 66—Polypeptide sequence of Q65F1 CDR2
SEQ ID NO: 67—Polypeptide sequence of Q65D1 CDR2
SEQ ID NO: 68—Polypeptide sequence of Q65D3 CDR2
SEQ ID NO: 69—Polypeptide sequence of Q65B1 CDR2
SEQ ID NO: 70—Polypeptide sequence of Q65F2 CDR3
SEQ ID NO: 71—Polypeptide sequence of Q65F1 CDR3
SEQ ID NO: 72—Polypeptide sequence of Q65D3 CDR3
SEQ ID NO: 73—Polypeptide sequence of Q65F6 CDR2
SEQ ID NO: 74—Polypeptide sequence of Q65F11 CDR2
SEQ ID NO: 75—Polypeptide sequence of Q65C12 CDR2
SEQ ID NO: 76—Polypeptide sequence of Q65A6 CDR2
SEQ ID NO: 77—Polypeptide sequence of Q65A3 CDR2
SEQ ID NO: 78—Polypeptide sequence of Q65F6 CDR3
SEQ ID NO: 79—Polypeptide sequence of Q65F11 CDR3
SEQ ID NO: 80—Polypeptide sequence of Q62F10 CDR3
SEQ ID NO: 81—Polynucleotide sequence of M13.rev
SEQ ID NO: 82—Polynucleotide sequence of M13.fw
SEQ ID NO: 83—Polynucleotide coding sequence of ID38F, codon optimised for yeast expression
SEQ ID NO: 84—Polynucleotide coding sequence of Q62E10, codon optimised for yeast expression
SEQ ID NO: 85—Polynucleotide coding sequence of ID38F, codon optimised for *E. coli* expression
SEQ ID NO: 86—Polynucleotide coding sequence of Q62E10, codon optimised for *E. coli* expression
SEQ ID NO: 87—Polynucleotide consisting of ID38F open reading frame for *E. coli* expression (PelB leader to c-myc-6His tag 2× stop codon)
SEQ ID NO: 88—Polynucleotide consisting of ID38F open reading frame for *E. coli* expression (PelB leader to Flag-6His tag 2× stop codon)

DETAILED DESCRIPTION OF THE INVENTION

Polypeptides Including Antibodies and Antibody Fragments Including the VH and VHH A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains. The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al 1991 Sequences of Proteins of Immunological Interest, *Fifth Edition U.S. Department of Health and Human Services*, NIH Publication Number 91-3242, herein incorporated by reference in its entirety). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulfide bonds, and the heavy chains similarity connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994 *Mol Immunol* 31:169-217).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans 2013 *Annu Rev Biochem* 82:775-797, Hamers-Casterman et al 1993 *Nature* 363(6428):446-448, Muyldermans et al 1994 *Protein Eng* 7(9):1129-1135, herein incorporated by reference in their entirety).

An antigen-binding fragment (or "antibody fragment" or "immunoglobulin fragment") as used herein refers to a portion of an antibody that specifically binds to TNF-alpha (e.g. a molecule in which one or more immunoglobulin chains is not full length, but which specifically binds to TNF-alpha). Examples of binding fragments encompassed within the term antigen-binding fragment include:

(i) a Fab fragment (a monovalent fragment consisting of the VLC, VHC, CL and CH1 domains);

(ii) a F(ab')2 fragment (a bivalent fragment comprising two Fab fragments linked by a disulfide bridge at the hinge region);

(iii) a Fd fragment (consisting of the VHC and CH1 domains);

(iv) a Fv fragment (consisting of the VLC and VHC domains of a single arm of an antibody);

(v) an scFv fragment (consisting of VLC and VHC domains joined, using recombinant methods, by a synthetic linker that enables them to be made as a single protein chain in which the VLC and VHC regions pair to form monovalent molecules);

(vi) a VH (an immunoglobulin chain variable domain consisting of a VHC domain (Ward et al *Nature* 1989 341:544-546);

(vii) a VL (an immunoglobulin chain variable domain consisting of a VLC domain);

(viii) a V-NAR (an immunoglobulin chain variable domain consisting of a VHC domain from chondrichthyes IgNAR (Roux et al 1998 *Proc Natl Acad Sci USA* 95:11804-11809 and Griffiths et al 2013 *Antibodies* 2:66-81, herein incorporated by reference in their entirety)

(ix) a VHH.

The total number of amino acid residues in a VHH or VH may be in the region of 110-130, is suitably 112-120, and is most suitably 115.

Immunoglobulin chain variable domains of the invention may for example be obtained by preparing a nucleic acid encoding an immunoglobulin chain variable domain using techniques for nucleic acid synthesis, followed by expression of the nucleic acid thus obtained According to a specific embodiment, an immunoglobulin chain variable domain of the invention does not have an amino acid sequence which is exactly the same as (i.e. shares 100% sequence identity with) the amino acid sequence of a naturally occurring polypeptide such as a VH or VHH domain of a naturally occurring antibody.

The examples provided herein relate to immunoglobulin chain variable domains per se which bind to TNF-alpha. The principles of the invention disclosed herein are, however, equally applicable to any polypeptide comprising an immunoglobulin chain variable domain which binds to TNF-alpha, such as antibodies and antibody fragments. For example, the anti-TNF-alpha immunoglobulin chain variable domains disclosed herein may be incorporated into a polypeptide such as a full length antibody. Such an approach is demonstrated by McCoy et al *Retrovirology* 2014, 11:83, who provide an anti-HIV VHH engineered as a fusion with a human Fc region (including hinge, CH2 and CH3 domains), expressed as a dimer construct.

Substituting at least one amino acid residue in the framework region of a non human immunoglobulin variable domain with the corresponding residue from a human variable domain is humanisation. Humanisation of a variable domain may reduce immunogenicity in humans.

Suitably, the polypeptide of the present invention consists of an immunoglobulin chain variable domain. Suitably, the polypeptide of the present invention is an antibody or an antibody fragment. Suitably the antibody fragment is a VHH, a VH, a VL, a V-NAR, a Fab fragment, a VL or a F(ab')2 fragment (such as a VHH or VH, most suitably a VHH).

Specificity, Affinity, Avidity and Cross-Reactivity

Specificity refers to the number of different types of antigens or antigenic determinants to which a particular antigen-binding polypeptide can bind. The specificity of an antigen-binding polypeptide is the ability of the antigen-binding polypeptide to recognise a particular antigen as a unique molecular entity and distinguish it from another.

Affinity, represented by the equilibrium constant for the dissociation of an antigen with an antigen-binding polypeptide (Kd), is a measure of the binding strength between an antigenic determinant and an antigen-binding site on the antigen-binding polypeptide: the lesser the value of the Kd, the stronger the binding strength between an antigenic determinant and the antigen-binding polypeptide (alternatively, the affinity can also be expressed as the affinity constant (Ka), which is 1/Kd). Affinity can be determined by known methods, depending on the specific antigen of interest.

Avidity is the measure of the strength of binding between an antigen-binding polypeptide and the pertinent antigen. Avidity is related to both the affinity between an antigenic determinant and its antigen binding site on the antigen-binding polypeptide and the number of pertinent binding sites present on the antigen-binding polypeptide.

Suitably, antigen-binding polypeptides of the invention will bind with a dissociation constant (Kd) of $10^{-6}$ to $10^{-12}$ M, more suitably $10^{-7}$ to $10^{-12}$ M, more suitably $10^{-8}$ to $10^{-12}$ M and more suitably $10^{-9}$ to $10^{-12}$ M.

Any Kd value less than $10^{-6}$ is considered to indicate binding. Specific binding of an antigen-binding polypeptide to an antigen or antigenic determinant can be determined in any suitable known manner, including, for example, Scatchard analysis and/or competitive binding assays, such as radioimmunoassays (RIA), enzyme immunoassays (EIA) and sandwich competition assays, and the different variants thereof known in the art.

An anti-TNF-alpha polypeptide, a polypeptide which interacts with TNF-alpha, or a polypeptide against TNF-alpha, are all effectively polypeptides which bind to TNF-alpha. A polypeptide of the invention may bind to a linear or conformational epitope on TNF-alpha. The term "binds to TNF-alpha" means binding to trimeric TNF-alpha, binding to a monomer of TNF-alpha and/or binding to a portion of a monomer of TNF-alpha.

Suitably, the polypeptide of the invention will bind to both soluble and membrane TNF-alpha. Suitably, the polypeptide of the invention will bind to human TNF-alpha. More suitably, the polypeptide of the invention will bind to both human and at least one additional primate TNF-alpha selected from the group consisting of baboon TNF-alpha, marmoset TNF-alpha, cynomolgus TNF-alpha and rhesus TNF-alpha. Most suitably, the polypeptide of the invention binds to both human and cynomolgus TNF-alpha.

Suitably, the polypeptide of the invention will neutralise both soluble and membrane TNF-alpha. Suitably, the polypeptide of the invention will neutralise human TNF-alpha. More suitably, the polypeptide of the invention will neutralise both human and at least one additional primate TNF-alpha selected from the group consisting of baboon TNF-alpha, marmoset TNF-alpha, cynomolgus TNF-alpha and rhesus TNF-alpha. Most suitably, the polypeptide of the invention neutralises both human and cynomolgus TNF-alpha.

Suitably, TNF-alpha is a polypeptide comprising SEQ ID NO: 9, more suitably TNF-alpha is a polypeptide consisting of SEQ ID NO: 9. Suitably, TNF-alpha is a polypeptide comprising SEQ ID NO: 10, more suitably TNF-alpha is a polypeptide consisting of SEQ ID NO: 10. Suitably, TNF-alpha is a polypeptide comprising SEQ ID NO: 11, more suitably TNF-alpha is a polypeptide consisting of SEQ ID NO: 11. Suitably, TNF-alpha is a polypeptide comprising SEQ ID NO: 12, more suitably TNF-alpha is a polypeptide consisting of SEQ ID NO: 12.

Polypeptides capable of reacting with TNF-alpha from humans and TNF-alpha from another species ("cross-reacting"), such as with cynomolgus monkey TNF-alpha, are advantageous because they allow preclinical studies to be more readily performed in animal models.

Suitably the polypeptide of the invention is directed against epitopes on TNF-alpha (and in particular of the TNF-alpha trimer) that lie in and/or form part of the receptor binding site(s) of the TNF-alpha trimer, such that said polypeptide of the invention, upon binding to a TNF-alpha trimer, is capable inhibiting or reducing the TNF-alpha receptor crosslinking that is mediated by said TNF-alpha trimer and/or the signal transduction that is mediated by such receptor crosslinking.

The polypeptides of the present invention bind to one or more epitope(s) on the TNF-alpha trimer. In one aspect of the invention there is provided a polypeptide which binds to the same epitope on the TNF-alpha trimer as Q65F2, Q65F3, Q62F2, Q65G1, Q65H6, Q65F1, Q65D1, Q65C7, Q65D3, Q65B1, Q65F6, Q65F11, Q65E12, Q65C12, Q65A6, Q65A3, Q62E10, Q62F10, ID7F-EV, ID8F-EV, ID9F-EV, ID13F-EV, ID14F-EV, ID15F-EV, ID22F, ID23F, ID24F, ID25F, ID26F, ID27F, ID28F, ID29F, ID34F, ID37F or ID38F.

Suitably, the polypeptide of the invention is isolated. An "isolated" polypeptide is one that is removed from its original environment. For example, a naturally-occurring polypeptide of the invention is isolated if it is separated from some or all of the coexisting materials in the natural system.

Potency, Inhibition and Neutralisation

Potency is a measure of the activity of a therapeutic agent expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target ligand and the quantitative magnitude of this response. The term half maximal effective concentration (EC50) refers to the concentration of a therapeutic agent which causes a response halfway between the baseline and maximum after a specified exposure time. The therapeutic agent may cause inhibition or stimulation. It is commonly used, and is used herein, as a measure of potency.

A neutralising polypeptide for the purposes of the invention is a polypeptide which binds to TNF-alpha, inhibiting the binding of TNF-alpha to one or both of its cognate receptors (e.g. TNFR1, TNFR2) as measured by ELISA. Alternatively, or in addition, a neutralising polypeptide for the purposes of the invention is a polypeptide which defends a cell from the effects of TNF-alpha by, for example, inhibiting the biological effect of TNF-alpha. Conventionally, anti-TNF-alpha therapeutic antibody products have used an L929 murine cell line with a cell death endpoint as a neutralisation assay (Humphreys and Wilson 1999 *Cytokine* 11(10):773-782). Methods for this purpose which utilise the L929 murine cell line include the following:

Fixed-concentration L929 assay—a fixed-concentration L929 assay can be used for a relatively quick indication of the ability of a fixed concentration of polypeptide e.g. contained within periplasmic extract to neutralise the effects of TNF-alpha cytotoxicity (as detailed in part 2.2.3 of the Examples section).

Normal L929 assay—using known concentrations of anti-TNF-alpha polypeptide, a normal L929 assay can be performed (as detailed in parts 3.2 to 3.2.3 of the Examples section) to assay the ability of an anti-TNF-alpha polypeptide to neutralise the effects of TNF-alpha cytotoxicity by ascertaining the half maximal effective concentration (EC50) of the anti-TNF-alpha polypeptide.

Suitably the polypeptide or construct of the invention neutralizes human TNF-alpha cytotoxicity in the normal L929 assay with an EC50 of 1 nM or less, such as 0.9 nM or less, such as 0.8 nM or less, such as 0.7 nM or less, such as 0.6 nM or less, such as 0.5 nM or less, such as 0.4 nM or less, such as 0.3 nM or less, such as 0.2 nM or less, such as 0.1 nM or less, such as 0.09 nM or less, such as 0.08 nM or less, such as 0.07 nM or less, such as 0.06 nM or less, such as 0.05 nM or less, such as 0.04 nM or less.

Suitably the polypeptide or construct of the invention neutralizes cynomolgus TNF-alpha cytotoxicity in the normal L929 assay with an EC50 of 1 nM or less, such as 0.9 nM or less, such as 0.8 nM or less, such as 0.7 nM or less, such as 0.6 nM or less, such as 0.5 nM or less, such as 0.4 nM or less, such as 0.3 nM or less, such as 0.2 nM or less, such as 0.1 nM or less, such as 0.09 nM or less, such as 0.08 nM or less, such as 0.07 nM or less, such as 0.06 nM or less, such as 0.05 nM or less, such as 0.04 nM or less, such as 0.03 nM or less, such as 0.02 nM or less, such as 0.01 nM or less.

Suitably, the polypeptide of the invention inhibits binding of human TNF-alpha to TNFR2 in an ELISA assay with an EC50 of 30 nM or less, more suitably 10 nM or less, more suitably 3 nM or less, more suitably 1 nM or less, more suitably 0.6 nM or less, more suitably 0.5 nM or less, more suitably 0.4 nM or less, more suitably 0.3 nM or less.

Suitably, the polypeptide of the invention inhibits binding of cynomolgus monkey TNF-alpha to TNFR2 in an ELISA assay with an EC50 of 110 nM or less, more suitably 30 nM or less, more suitably 10 nM or less, more suitably 3 nM or less, more suitably 1 nM or less, more suitably 0.6 nM or less, more suitably 0.5 nM or less, more suitably 0.4 nM or less, more suitably 0.3 nM or less.

Suitably, the polypeptide of the invention inhibits binding of human TNF-alpha to TNFR1 in an ELISA assay with an EC50 of 2 nM or less, more suitably 1 nM or less, more suitably 0.9 nM or less, more suitably 0.8 nM or less, more suitably 0.7 nM or less, more suitably 0.6 nM or less, more suitably 0.5 nM or less, more suitably 0.4 nM or less, more suitably 0.3 nM or less.

Suitably, the polypeptide of the invention inhibits soluble human TNF-alpha-induced HEK-293-NF-kappa-B SEAP reporter cell activation with an EC50 of 3 nM or less, suitably 2 nM or less, suitably 1 nM or less, suitably 0.5 nM or less, suitably 0.4 nM or less, suitably 0.3 nM or less, suitably 0.2 nM or less, suitably 0.1 nM or less, suitably 0.08 nM or less.

Suitably, the polypeptide of the invention inhibits membrane human TNF-alpha-induced HEK-293-NF-kappa-B SEAP reporter cell activation with an EC50 of 300 nM or less, suitably 150 nM or less, suitably 100 nM or less, suitably 80 nM or less, suitably 40 nM or less, suitably 30 nM or less, suitably 25 nM or less, suitably 20 nM or less, suitably 15 nM or less.

Polypeptide and Polynucleotide Sequences

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
|---|---|
| Non-polar aliphatic | Glycine |
|  | Alanine |
|  | Valine |
|  | Leucine |
|  | Isoleucine |
| Aromatic | Phenylalanine |
|  | Tyrosine |
|  | Tryptophan |
| Polar uncharged | Serine |
|  | Threonine |
|  | Asparagine |
|  | Glutamine |
| Negatively charged | Aspartate |
|  | Glutamate |

| Group | Amino acid residue |
| --- | --- |
| Positively charged | Lysine |
| | Arginine |

Suitably, a hydrophobic amino acid residue is a non-polar amino acid. More suitably, a hydrophobic amino acid residue is selected from V, I, L, M, F, W or C.

As used herein, numbering of polypeptide sequences and definitions of CDRs and FRs are as defined according to the Kabat system (Kabat et al 1991 Sequences of Proteins of Immunological Interest, Fifth Edition U.S. Department of Health and Human Services, NIH Publication Number 91-3242, herein incorporated by reference in its entirety). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings.

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

In one aspect of the invention there is provided a polynucleotide encoding the polypeptide or construct of the invention. Suitably the polynucleotide comprises or consists of a sequence sharing 70% or greater, such as 80% or greater, such as 90% or greater, such as 95% or greater, such as 99% or greater sequence identity with any one of SEQ ID NOs: 83 to 88.

More suitably the polynucleotide comprises or consists of any one of SEQ ID NOs: 83 to 88. In a further aspect there is provided a cDNA comprising said polynucleotide.

In one aspect of the invention there is provided a polynucleotide comprising or consisting of a sequence sharing 70% or greater, such as 80% or greater, such as 90% or greater, such as 95% or greater, such as 99% or greater sequence identity with any one of the portions of any one of SEQ ID NOs: 83 to 86 which encodes CDR1, CDR2 or CDR3 of the encoded immunoglobulin chain variable domain.

Suitably, the polypeptide sequence of the present invention contains at least one alteration with respect to a native sequence. Suitably, the polynucleotide sequences of the present invention contain at least one alteration with respect to a native sequence. Suitably the alteration to the polypeptide sequence or polynucleotide sequence is made to increase stability of the polypeptide or encoded polypeptide to proteases present in the intestinal tract (for example trypsin and chymotrypsin).

The Kabat Numbering System Applied to Selected Immunoglobulin Chain Variable Domain Sequences

| Region | FR1 | FR1 | FR1 | FR1 | FR1 | FR1 | FR1 | FR1 | FR1 | FR1 | FR1 | FR1 | FR1 | FR1 | FR1 | FR1 | FR1 | FR1 | FR1 | FR1 | FR1 |
|---|---|---|---|---|---|---|---|---|---|---|---|---|---|---|---|---|---|---|---|---|---|
| Residue # | 1 | 2 | 3 | 4 | 5 | 6 | 7 | 8 | 9 | 10 | 11 | 12 | 13 | 14 | 15 | 16 | 17 | 18 | 19 | 20 | 21 |
| Q62E10 | Q | V | Q | L | V | E | S | G | G | G | L | V | Q | P | G | G | S | L | R | L | S |
| Q65B1 | E | V | Q | L | V | E | S | G | G | G | L | V | Q | P | G | G | S | L | K | L | S |
| ID38F | D | V | Q | L | V | E | S | G | G | G | L | V | Q | P | G | G | S | L | K | L | S |
| TNF1 | E | V | Q | L | V | E | S | G | G | G | L | V | Q | P | G | G | S | L | R | L | S |
| Kabat numbering | H1 | H2 | H3 | H4 | H5 | H6 | H7 | H8 | H9 | H10 | H11 | H12 | H13 | H14 | H15 | H16 | H17 | H18 | H19 | H20 | H21 |

| Region | FR1 | FR1 | FR1 | FR1 | FR1 | FR1 | FR1 | FR1 | FR1 | CDR1 | CDR1 | CDR1 | CDR1 | CDR1 | FR2 | FR2 | FR2 | FR2 | FR2 | FR2 | FR2 |
|---|---|---|---|---|---|---|---|---|---|---|---|---|---|---|---|---|---|---|---|---|---|
| Residue # | 22 | 23 | 24 | 25 | 26 | 27 | 28 | 29 | 30 | 31 | 32 | 33 | 34 | 35 | 36 | 37 | 38 | 39 | 40 | 41 | 42 |
| Q62E10 | C | T | T | S | G | L | D | F | G | I | H | W | M | Y | W | F | R | Q | A | P | G |
| Q65B1 | C | A | A | S | G | F | D | F | S | S | H | W | M | Y | W | V | R | Q | A | P | G |
| ID38F | C | A | A | S | G | F | D | F | S | S | H | W | M | Y | W | V | R | Q | A | P | G |
| TNF1 | C | A | A | S | G | F | T | F | S | D | Y | W | M | Y | W | V | R | Q | A | P | G |
| Kabat numbering | H22 | H23 | H24 | H25 | H26 | H27 | H28 | H29 | H30 | H31 | H32 | H33 | H34 | H35 | H36 | H37 | H38 | H39 | H40 | H41 | H42 |

| Region | FR2 | FR2 | FR2 | FR2 | FR2 | FR2 | FR2 | CDR2 | CDR2 | CDR2 | CDR2 | CDR2 | CDR2 | CDR2 | CDR2 | CDR2 | CDR2 | CDR2 | CDR2 | CDR2 | CDR2 |
|---|---|---|---|---|---|---|---|---|---|---|---|---|---|---|---|---|---|---|---|---|---|
| Residue # | 43 | 44 | 45 | 46 | 47 | 48 | 49 | 50 | 51 | 52 | 53 | 54 | 55 | 56 | 57 | 58 | 59 | 60 | 61 | 62 | 63 |
| Q62E10 | K | E | L | E | W | V | A | E | I | N | T | N | A | L | I | T | K | Y | A | D | S |
| Q65B1 | K | E | L | E | W | L | S | E | I | N | T | N | G | L | I | T | K | Y | G | D | S |
| ID38F | K | E | L | E | W | L | S | E | I | N | T | N | G | L | I | T | H | Y | G | D | S |
| TNF1 | K | G | L | E | W | V | S | E | I | N | T | N | G | L | I | T | K | Y | P | D | S |
| Kabat numbering | H43 | H44 | H45 | H46 | H47 | H48 | H49 | H50 | H51 | H52 | H52A | H53 | H54 | H55 | H56 | H57 | H58 | H59 | H60 | H61 | H62 |

-continued

| Region | CDR2 | CDR2 | CDR2 | FR3 | FR3 | FR3 | FR3 | FR3 | FR3 | FR3 | FR3 | FR3 | FR3 | FR3 | FR3 | FR3 | FR3 | FR3 | FR3 | FR3 | FR3 |
|---|---|---|---|---|---|---|---|---|---|---|---|---|---|---|---|---|---|---|---|---|---|
| Residue # | 64 | 65 | 66 | 67 | 68 | 69 | 70 | 71 | 72 | 73 | 74 | 75 | 76 | 77 | 78 | 79 | 80 | 81 | 82 | 83 | 84 |
| Q62E10 | V | K | G | R | F | T | I | S | R | D | N | A | K | N | T | L | F | L | Q | M | N |
| Q65B1 | V | K | G | R | F | T | V | S | R | N | N | A | A | N | K | M | Y | L | E | L | T |
| ID38F | V | K | G | R | F | T | V | S | R | N | N | A | A | N | K | M | Y | L | E | L | T |
| TNF1 | V | K | G | R | F | T | I | S | R | D | N | A | K | N | T | L | Y | L | Q | M | N |
| Kabat numbering | H63 | H64 | H65 | H66 | H67 | H68 | H69 | H70 | H71 | H72 | H73 | H74 | H75 | H76 | H77 | H78 | H79 | H80 | H81 | H82 | H82A |

| Region | FR3 | FR3 | FR3 | FR3 | FR3 | FR3 | FR3 | FR3 | FR3 | FR3 | FR3 | FR3 | FR3 | CDR3 | CDR3 | CDR3 | CDR3 | CDR3 | CDR3 | CDR3 | FR4 |
|---|---|---|---|---|---|---|---|---|---|---|---|---|---|---|---|---|---|---|---|---|---|
| Residue # | 85 | 86 | 87 | 88 | 89 | 90 | 91 | 92 | 93 | 94 | 95 | 96 | 97 | 98 | 99 | 100 | 101 | 102 | 103 | 104 | 105 |
| Q62E10 | D | L | K | S | E | D | T | A | V | Y | Y | C | S | N | T | Q | N | G | A | A | K |
| Q65B1 | R | L | E | P | E | D | T | A | L | Y | Y | C | A | R | N | Q | K | G | L | N | K |
| ID38F | R | L | E | P | E | D | T | A | L | Y | Y | C | A | R | N | Q | H | G | L | N | K |
| TNF1 | S | L | K | P | E | D | T | A | L | Y | Y | C | A | R | S | P | S | G | F | N | R |
| Kabat numbering | H82B | H82C | H83 | H84 | H85 | H86 | H87 | H88 | H89 | H90 | H91 | H92 | H93 | H94 | H95 | H96 | H97 | H98 | H101 | H102 | H103 |

| Region | FR4 | FR4 | FR4 | FR4 | FR4 | FR4 | FR4 | FR4 | FR4 | FR4 | FR4 |
|---|---|---|---|---|---|---|---|---|---|---|---|
| Residue # | 106 | 107 | 108 | 109 | 110 | 111 | 112 | 113 | 114 | 115 | |
| Q62E10 | G | Q | G | V | Q | V | T | V | S | S | |
| Q65B1 | G | Q | G | T | Q | V | T | V | S | S | |
| ID38F | G | Q | G | T | Q | V | T | V | S | S | |
| TNF1 | G | Q | G | T | Q | V | T | V | S | S | |
| Kabat numbering | H104 | H105 | H106 | H107 | H108 | H109 | H110 | H111 | H112 | H113 | |

Sequences Belonging to Family 1

Suitably CDR1 of the polypeptide of the present invention comprises or more suitably consists of a sequence sharing 80% or greater sequence identity with SEQ ID NO: 1.

Alternatively, CDR1 of the polypeptide of the present invention comprises or more suitably consists of a sequence having no more than 2, more suitably no more than 1 addition(s) compared to SEQ ID NO: 1. Suitably, CDR1 of the polypeptide of the present invention comprises or more suitably consists of a sequence having no more than 2, more suitably no more than 1 substitution(s) compared to SEQ ID NO: 1. Suitably, CDR1 of the polypeptide of the present invention comprises or more suitably consists of a sequence having no more than 2, more suitably no more than 1 deletion(s) compared to SEQ ID NO: 1.

Suitably any residues of CDR1 differing from their corresponding residues in SEQ ID NO: 1 are conservative substitutions with respect to their corresponding residues. Suitably CDR1 comprises or more suitably consists of SEQ ID NO: 1. Suitably the sequence of CDR1 is SEQ ID NO: 1, SEQ ID NO: 59 or SEQ ID NO: 60.

Suitably CDR2 of the polypeptide of the present invention comprises or more suitably consists of a sequence sharing 55%, 60%, 70%, 75%, 80%, 85%, 90% or greater sequence identity, with SEQ ID NO: 2.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 2.

Suitably any residues of CDR2 differing from their corresponding residues in SEQ ID NO: 2 are conservative substitutions with respect to their corresponding residues. Suitably the residue of CDR2 corresponding to residue number 10 of SEQ ID NO: 2 is R, H, D, E, N, Q, S, T, Y, G, A, V, L, W, P, M, C, F or I (most suitably H). Suitably CDR2 comprises or more suitably consists of SEQ ID NO: 2. Suitably the sequence of CDR2 is SEQ ID NO: 61, SEQ ID NO: 62, SEQ ID NO: 2, SEQ ID NO: 63, SEQ ID NO: 64, SEQ ID NO: 65, SEQ ID NO: 66, SEQ ID NO: 67, SEQ ID NO: 68, SEQ ID NO: 69.

Suitably CDR3 of the polypeptide of the present invention comprises or more suitably consists of a sequence sharing 80% or greater sequence identity with SEQ ID NO: 3.

Alternatively, CDR3 of the polypeptide of the present invention comprises or more suitably consists of a sequence having no more than 3, more suitably no more than 2, more suitably no more than 1 addition(s) compared to SEQ ID NO: 3. Suitably, CDR3 of the polypeptide of the present invention comprises or more suitably consists of a sequence having no more than 3, more suitably no more than 2, more suitably no more than 1 substitution(s) compared to SEQ ID NO: 3. Suitably, CDR3 of the polypeptide of the present invention comprises or more suitably consists of a sequence having no more than 3, more suitably no more than 2, more suitably no more than 1 deletion(s) compared to SEQ ID NO: 3. Suitably, any substitutions are conservative, with respect to their corresponding residues in SEQ ID NO: 3.

Suitably any residues of CDR3 differing from their corresponding residues in SEQ ID NO: 3 are conservative substitutions with respect to their corresponding residues. Suitably the residue of CDR3 corresponding to residue number 3 of SEQ ID NO: 3 is R, H, D, E, N, Q, S, T, Y, G, A, V, L, W, P, M, C, F or I; or suitably R, H, D, E, N, Q, S, T, Y, G, V, L, W, P, M, C, F or I (most suitably H). Suitably the residue of CDR3 corresponding to residue number 3 of SEQ ID NO: 3 is H and any other residues of CDR3 differing from their corresponding residues in SEQ ID NO: 3 are conservative substitutions with respect to their corresponding residues. Suitably CDR3 comprises or more suitably consists of SEQ ID NO: 3.

Alternatively CDR3 of the polypeptide of the present invention comprises or more suitably consists of a sequence sharing 50%, such as 60%, such as 80% or greater sequence identity with SEQ ID NO: 3 and wherein residue number 3 of SEQ ID NO: 3 is R, D, N, C, E, Q, G, H, I, L, K, M, F, P, S, T, W, Y or V (suitably H or a conservative substitution of H; more suitably H). Alternatively residue number 3 of SEQ ID NO: 3 is H or a conservative substitution of H (most suitably H) and any other residues of CDR3 differing from their corresponding residues in SEQ ID NO: 3 are conservative substitutions. Suitably the sequence of CDR3 is SEQ ID NO: 3, SEQ ID NO: 70, SEQ ID NO: 71 or SEQ ID NO: 72

Suitably residue 1 of CDR1 is S, V or N; residues 2 to 4 are HWM and residue 5 is Y or C. Suitably, residues 1 to 9 of CDR2 are EINTNGLIT; residue 10 is H, K, S or N; residue 11 is Y, residue 12 is G, V, I or A; residue 13 is D; residue 14 is S or F; residue 15 is V or T; residue 16 is H, K, R or G and residue 17 is G. Suitably residue 1 of CDR3 is N; residue 2 is Q or E; residue 3 is H, K, M or R and residues 4 to 6 are GLN.

Some particularly suitable CDR sequences are shown in the table below. Suitably, CDR1 of the polypeptide of the invention is one of the CDR1 sequences listed below. Suitably, CDR2 of the polypeptide of the invention is one of the CDR2 sequences listed below. Suitably, CDR3 of the polypeptide of the invention is one of the CDR3 sequences listed below. Suitably, the polypeptide of the invention comprises a combination of two, or more suitably three, of the CDR sequences listed below.

Particular Family 1 CDRs of the Polypeptide of the Invention:

| CDR1 | CDR2 | CDR3 |
| --- | --- | --- |
| SHWMY (SEQ ID NO: 1) | EINTNGLITHYGDSVHG (SEQ ID NO: 61) | NQHGLN (SEQ ID NO: 3) |
| VHWMY (SEQ ID NO: 59) | EINTNGLITKYGDSVHG (SEQ ID NO: 62) | NQKGLN (SEQ ID NO: 70) |

-continued

NHWMC (SEQ ID NO: 60)   EINTNGLITHYGDSVKG         NQMGLN (SEQ ID NO: 71)
                        (SEQ ID NO: 2)

EINTNGLITSYVDSVKG         NERGLN (SEQ ID NO: 72)
                        (SEQ ID NO: 63)

EINTNGLITKYIDSVRG
                        (SEQ ID NO: 64)

EINTNGLITNYVDSVKG
                        (SEQ ID NO: 65)

EINTNGLITKYIDSVGG
                        (SEQ ID NO: 66)

EINTNGLITKYADFVKG
                        (SEQ ID NO: 67)

EINTNGLITKYADSTKG
                        (SEQ ID NO: 68)

EINTNGLITKYGDSVKG
                        (SEQ ID NO: 69)

Percentage identity of CDRs of ID38F to other Family 1 members, TNF1 and Q62F11

| Name | CDR 1 | CDR 2 | CDR 3 |
| --- | --- | --- | --- |
| Q65B1 | 100 | 94.1 | 83.3 |
| Q65F2 | 100 | 88.2 | 83.3 |
| Q65F3 | 100 | 82.4 | 83.3 |
| Q62F2 | 100 | 88.2 | 83.3 |
| Q65G1 | 100 | 82.4 | 83.3 |
| Q65H6 | 100 | 82.4 | 83.3 |
| Q65F1 | 80 | 82.4 | 83.3 |
| Q65D1 | 60 | 82.4 | 83.3 |
| Q65D3 | 100 | 82.4 | 66.7 |
| Q65C7 | 100 | 82.4 | 83.3 |
| TNF1 | 60 | 88.2 | 33.3 |
| Q62F11 | 20 | 52.9 | 13.3 |

Suitably FR1 of the polypeptide of the present invention comprises or more suitably consists of a sequence sharing 5%, 12%, 18%, 26%, 32%, 38%, 46%, 52%, 58%, 62%, 66%, 68%, 72%, 75%, 78%, 82%, 85%, 90%, 95% or greater sequence identity, with SEQ ID NO: 4.

Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 4. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 4. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 4.

Suitably any residues of FR1 differing from their corresponding residues in SEQ ID NO: 4 are conservative substitutions with respect to their corresponding residues. Suitably the residue of FR1 corresponding to residue number 1 of SEQ ID NO: 4 is G, A, V, L, I, F, P, S, T, Y, C, M, K, R, H, W, D, E or N (more suitably D or E, most suitably D). Suitably the residue of FR1 corresponding to residue number 5 of SEQ ID NO: 4 is G, A, V, L, I, F, P, S, T, Y, C, M, K, R, H, W, D, E or N (suitably V). Suitably the residues of FR1 corresponding to residue numbers 1 to 5 of SEQ ID NO: 4 are DVQLV. Suitably the residue of FR1 corresponding to residue numbers 20 and/or 24 of SEQ ID NO: 4 are an amino acid which is hydrophobic (most suitably L or A, respectively). Suitably the residue of FR1 corresponding to residue number 29 of SEQ ID NO: 4 is F. Suitably FR1 comprises or more suitably consists of SEQ ID NO: 4.

Suitably FR2 of the polypeptide of the present invention comprises or more suitably consists of a sequence sharing 10%, 15%, 25%, 30%, 40%, 45%, 55%, 60%, 70%, 75%, 85%, 90% or greater sequence identity, with SEQ ID NO: 5.

Alternatively, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 5. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 5. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 5.

Suitably any residues of FR2 differing from their corresponding residues in SEQ ID NO: 5 are conservative substitutions with respect to their corresponding residues. Suitably the residues of FR2 corresponding to residue numbers 8 to 11 of SEQ ID NO: 5 are KEXE, wherein X is R or L. Alternatively the residues of FR2 corresponding to residue numbers 9 to 12 of SEQ ID NO: 5 are GLEW. Suitably FR2 comprises or more suitably consists of SEQ ID NO: 5.

Suitably FR3 of the polypeptide of the present invention comprises or more suitably consists of a sequence sharing 8%, 15%, 20%, 26%, 32%, 40%, 45%, 52%, 58%, 65%, 70%, 76%, 80%, 82%, 85%, 90%, 92%, 95% or greater sequence identity, with SEQ ID NO: 6.

Alternatively, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 addition(s) compared to SEQ ID NO: 6. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 6. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 6.

Suitably the residue of FR3 corresponding to residue number 26 of SEQ ID NO: 6 is an amino acid which is hydrophobic (suitably A). Suitably any residues of FR3 differing from their corresponding residues in SEQ ID NO: 6 are conservative substitutions with respect to their corresponding residues. Suitably FR3 comprises or more suitably consists of SEQ ID NO: 6.

Suitably FR4 of the polypeptide of the present invention comprises or more suitably consists of a sequence sharing 5%, 10%, 20%, 30%, 40%, 50%, 60%, 70%, 80%, 90% or greater sequence identity, with SEQ ID NO: 7.

Alternatively, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 7.

Suitably any residues of FR4 differing from their corresponding residues in SEQ ID NO: 7 are conservative substitutions with respect to their corresponding residues. Suitably FR4 comprises or more suitably consists of SEQ ID NO: 7.

Suitably the polypeptide of the present invention comprises or more suitably consists of a sequence sharing 50%, 55%, 60%, 65%, 70%, 75%, 80%, 85%, 90%, 95%, 96%, 97%, 98%, 99% or greater sequence identity, with SEQ ID NO: 8.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 8. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 8. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 8.

Suitably the N-terminus of the polypeptide is D. Suitably the polypeptide comprises or more suitably consists of SEQ ID NO: 8.

Sequences Belonging to Family 2

Suitably CDR1 of the polypeptide of the present invention comprises or more suitably consists of a sequence sharing 80% or greater sequence identity with SEQ ID NO: 15.

Alternatively, CDR1 of the polypeptide of the present invention comprises or more suitably consists of a sequence having no more than 2, more suitably no more than 1, addition(s), compared to SEQ ID NO: 15. Suitably, CDR1 of the polypeptide of the present invention comprises or more suitably consists of a sequence having no more than 2, more suitably no more than 1, substitution(s) compared to SEQ ID NO: 15. Suitably, CDR1 of the polypeptide of the present invention comprises or more suitably consists of a sequence having no more than 2, more suitably no more than 1, deletion(s) compared to SEQ ID NO: 15.

Suitably any residues of CDR1 differing from their corresponding residues in SEQ ID NO: 15 are conservative substitutions with respect to their corresponding residues. Suitably CDR1 comprises or more suitably consists of SEQ ID NO: 15.

Suitably CDR2 of the polypeptide of the present invention comprises or more suitably consists of a sequence sharing 55%, 60%, 70%, 75%, 80%, 85%, 90% or greater sequence identity, with SEQ ID NO: 16.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1, addition(s) compared to SEQ ID NO: 16. Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1, substitutions(s) compared to SEQ ID NO: 16. Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1, deletions(s) compared to SEQ ID NO: 16.

Suitably the residue of CDR2 corresponding to residue number 10 and/or 16 of SEQ ID NO: 16 is R, H, D, E, N, Q, S, T, Y, G, A, V, L, W, P, M, C, F or I (more suitably H). Suitably any residues of CDR2 differing from their corresponding residues in SEQ ID NO: 16 are conservative substitutions with respect to their corresponding residues. Suitably CDR2 comprises or more suitably consists of SEQ ID NO: 16. Suitably the sequence of CDR2 is SEQ ID NO: 73, SEQ ID NO: 74, SEQ ID NO: 75, SEQ ID NO: 76, SEQ ID NO: 77 or SEQ ID NO: 16.

Suitably CDR3 of the polypeptide of the present invention comprises or more suitably consists of a sequence sharing 60% or greater sequence identity, such as 80% or greater sequence identity, with SEQ ID NO: 17.

Alternatively, CDR3 of the polypeptide of the present invention comprises or more suitably consists of a sequence having no more than 3, more suitably no more than 2, more suitably no more than 1, addition(s) compared to SEQ ID NO: 17. Suitably, CDR3 of the polypeptide of the present invention comprises or more suitably consists of a sequence having no more than 3, more suitably no more than 2, more suitably no more than 1, substitution(s) compared to SEQ ID NO: 17. Suitably, CDR3 of the polypeptide of the present invention comprises or more suitably consists of a sequence having no more than 3, more suitably no more than 2, more suitably no more than 1, deletion(s) compared to SEQ ID NO: 17.

Suitably any residues of CDR3 differing from their corresponding residues in SEQ ID NO: 17 are conservative substitutions with respect to their corresponding residues. Suitably the sequence of CDR3 is SEQ ID NO: 78, SEQ ID NO: 79, SEQ ID NO: 17 or SEQ ID NO: 80. Suitably CDR3 comprises or more suitably consists of SEQ ID NO: 17.

Suitably residues 1 to 5 of CDR1 are IHWMY. Suitably residues 1 to 9 of CDR2 are EINTNGLIT; residue 10 is L, T, H, K or V; residue 11 is Y; residue 12 is S, A, T or P; residues 13 to 15 are DSV; residue 16 is R, K or S and residue 17 is G. Suitably residue 1 of CDR3 is S, A or T; residue 2 is R or Q; residues 3 to 4 are NG; residue 5 is A or K and residue 6 is A or T.

Some particularly suitable CDR sequences are shown in the table below. Suitably, CDR1 of the polypeptide of the invention is one of the CDR1 sequences listed below. Suitably, CDR2 of the polypeptide of the invention is one of the CDR2 sequences listed below. Suitably, CDR3 of the polypeptide of the invention is one of the CDR3 sequences listed below. Suitably, the polypeptide of the invention comprises a combination of two, or more suitably three, of the CDR sequences listed below.

Particular Family 2 CDRs of the Polypeptide of the Invention:

| CDR1 | CDR2 | CDR3 |
| --- | --- | --- |
| IHWMY (SEQ ID NO: 15) | EINTNGLITLYSDSVRG (SEQ ID NO: 73) | SRNGAA (SEQ ID NO: 78) |

```
EINTNGLITLYADSVKG      ARNGAA (SEQ ID NO: 79)
(SEQ ID NO: 74)

EINTNALITTYADSVKG      TQNGAA (SEQ ID NO: 17)
(SEQ ID NO: 75)

EINTNGLITHYTDSVSG      TQNGKT (SEQ ID NO: 80)
(SEQ ID NO: 76)

EINTNALITKYADSVKG
(SEQ ID NO: 77)

EINTNGLITVYPDSVKG
(SEQ ID NO: 16)
```

Percentage identity of CDRs of 62E10 to other Family 2 members, TNF1 and Q62F11

| Name | CDR 1 | CDR 2 | CDR 3 |
|---|---|---|---|
| Q65F6 | 100 | 76.5 | 66.7 |
| Q65F11 | 100 | 88.2 | 66.7 |
| Q65E12 | 100 | 88.2 | 66.7 |
| Q62C12 | 100 | 94.1 | 66.7 |
| Q65A6 | 100 | 76.5 | 66.7 |
| Q65A3 | 100 | 100 | 100 |
| Q65F10 | 100 | 82.4 | 66.7 |
| TNF1 | 60 | 88.2 | 16.7 |
| Q62F11 | 20 | 52.9 | 13.3 |

Suitably FR1 of the polypeptide of the present invention comprises or more suitably consists of a sequence sharing 5%, 12%, 18%, 26%, 32%, 38%, 46%, 52%, 58%, 62%, 66%, 68%, 72%, 75%, 78%, 82%, 85%, 90%, 95% or greater sequence identity, with SEQ ID NO: 18.

Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 18. Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 18. Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 18.

Suitably the residue of FR1 corresponding to residue number 1 of SEQ ID NO: 4 is G, A, V, L, I, F, P, S, T, Y, C, M, K, R, H, W, D, E or N (more suitably D or E, most suitably D). Suitably the residue of FR1 corresponding to residue number 5 of SEQ ID NO: 18 is G, A, V, L, I, F, P, S, T, Y, C, M, K, R, H, W, D, E or N (suitably V). Suitably the residues of FR1 corresponding to residue numbers 1 to 5 of SEQ ID NO: 18 are DVQLV. Suitably the residue of FR1 corresponding to residue number 20 of SEQ ID NO: 18 is an amino acid which is hydrophobic (suitably L). Suitably the residue of FR1 corresponding to residue number 29 of SEQ ID NO: 18 is F. Suitably any residues of FR1 differing from their corresponding residues in SEQ ID NO: 18 are conservative substitutions with respect to their corresponding residues. Suitably FR1 comprises or more suitably consists of SEQ ID NO: 18.

Suitably FR2 of the polypeptide of the present invention comprises or more suitably consists of a sequence sharing 10%, 15%, 25%, 30%, 40%, 45%, 55%, 60%, 70%, 75%, 85%, 90% or greater sequence identity, with SEQ ID NO: 19.

Alternatively, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 19. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 19. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 19.

Suitably the residues of FR2 corresponding to residue numbers 8 to 11 of SEQ ID NO: 19 are KELE. Suitably any residues of FR2 differing from their corresponding residues in SEQ ID NO: 19 are conservative substitutions with respect to their corresponding residues. Suitably FR2 comprises or more suitably consists of SEQ ID NO: 19.

Suitably FR3 of the polypeptide of the present invention comprises a sequence sharing 8%, 15%, 20%, 26%, 32%, 40%, 45%, 52%, 58%, 65%, 70%, 76%, 80%, 82%, 85%, 90%, 92%, 95% or greater sequence identity, with SEQ ID NO: 20.

Alternatively, FR3 of the polypeptide of the present invention comprises or more suitably consists of a sequence having no more than 29, more suitably 27, more suitably 25, more suitably 23, more suitably 21, more suitably 19, more suitably 17, more suitably 15, more suitably 13, more suitably 11, more suitably 9, more suitably 7, more suitably 6, more suitably 5, more suitably 4, more suitably 3, more suitably 2, more suitably 1 addition(s) compared to SEQ ID NO: 20. Suitably, FR3 of the polypeptide of the present invention comprises or more suitably consists of a sequence having no more than 29, more suitably 27, more suitably 25, more suitably 23, more suitably 21, more suitably 19, more suitably 17, more suitably 15, more suitably 13, more suitably 11, more suitably 9, more suitably 7, more suitably 6, more suitably 5, more suitably 4, more suitably 3, more suitably 2, more suitably 1 substitution(s) compared to SEQ ID NO: 20. Suitably, FR3 of the polypeptide of the present invention comprises or more suitably consists of a sequence having no more than 29, more suitably 27, more suitably 25, more suitably 23, more suitably 21, more suitably 19, more suitably 17, more suitably 15, more suitably 13, more suitably 11, more suitably 9, more suitably 7, more suitably 6, more suitably 5, more suitably 4, more suitably 3, more suitably 2, more suitably 1 deletion(s) compared to SEQ ID NO: 20.

Suitably the residue of FR3 corresponding to residue number 26 of SEQ ID NO: 20 is an amino acid which is hydrophobic (suitably A). Suitably any residues of FR3 differing from their corresponding residues in SEQ ID NO: 20 are conservative substitutions with respect to their corresponding residues. Suitably FR3 comprises or more suitably consists of SEQ ID NO: 20.

Suitably FR4 of the polypeptide of the present invention comprises a sequence sharing 5%, 10%, 20%, 30%, 40%, 50%, 60%, 70%, 80%, 90% or greater sequence identity, with SEQ ID NO: 21.

Alternatively, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 21. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 21. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 21.

Suitably the residue of CDR2 corresponding to residue number 1 of SEQ ID NO: 21 is R, H, D, E, N, Q, S, T, Y, G, A, V, L, W, P, M, C, F or I (suitably H). Suitably any residues of FR4 differing from their corresponding residues in SEQ ID NO: 21 are conservative substitutions with respect to their corresponding residues. Suitably FR4 comprises or more suitably consists of SEQ ID NO: 21.

Suitably the polypeptide of the present invention comprises or more suitably consists of a sequence sharing 50%, 55%, 60%, 65%, 70%, 75%, 80%, 85%, 90%, 95%, 96%, 97%, 98%, 99% or greater sequence identity, with SEQ ID NO: 22.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 22. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitutions(s) compared to SEQ ID NO: 22. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 22.

Suitably the polypeptide comprises or more suitably consists of SEQ ID NO: 22. Suitably the N-terminus of the polypeptide is D. Suitably the polypeptide comprises or more suitably consists of SEQ ID NO: 55.

Suitably, the polypeptide of the present invention comprises, or more suitably consists of, a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1, substitution(s) with respect to SEQ ID NO: 22. Suitably, any substitutions are conservative, with respect to their corresponding residues in SEQ ID NO: 22.

Linkers and Multimers

A construct according to the invention comprises multiple polypeptides and therefore may suitably be multivalent. Such a construct may comprise at least two identical polypeptides according to the invention. A construct consisting of two identical polypeptides according to the invention is a "homobihead". In one aspect of the invention there is provided a construct comprising two or more identical polypeptides of the invention.

Alternatively, a construct may comprise at least two polypeptides which are different, but are both still polypeptides according to the invention (a "heterobihead").

Alternatively, such a construct may comprise (a) at least one polypeptide according to the invention and (b) at least one polypeptide such as an antibody or antigen-binding fragment thereof, which is not a polypeptide of the invention (also a "heterobihead"). The at least one polypeptide of (b) may bind TNF-alpha (for example via a different epitope to that of (a)), or alternatively may bind to a target other than TNF-alpha. Suitably the different polypeptide (b) binds to, for example: an interleukin (such as IL-1, IL-1ra, IL-4, IL-5, IL-6, IL-7, IL-8, IL-9, IL-10, IL-11, IL-12, IL-13, IL-15, IL-17, IL-18 and IL-23), an interleukin receptor (such as IL-6R and IL-7R), a transcription factor (such as NF-kB), a cytokine (such as TNF-alpha, IFN-gamma TGF-beta and TSLP), a transmembrane protein (such as gp130 and CD3), a surface glycoprotein (such as CD4, CD20, CD40), a soluble protein (such as CD40L), an integrin (such as a4b7 and AlphaEbeta7), an adhesion molecule (such as MAd-CAM), a chemokine (such as IP10 and CCL20), a chemokine receptor (such as CCR2 and CCR9), an inhibitory protein (such as SMAD7), a kinase (such as JAK3), a G protein-coupled receptor (such as sphingosine-1-P receptor), other inflammatory mediators or immunologically relevant ligands involved in human pathological processes. Thus the different polypeptide (b) binds to, for example, IL-6R, IL-6, IL-12, IL-23, IL-1-beta, IL-17A or CD3; or other inflammatory mediators or immunologically relevant ligands involved in human pathological processes.

Constructs can be multivalent and/or multispecific. A multivalent construct (such as a bivalent construct) comprises two or more binding polypeptides therefore presents two or more sites at which attachment to one or more antigens can occur. An example of a multivalent construct could be a homobihead or a heterobihead. A multispecific construct (such as a bispecific construct) comprises two or more different binding polypeptides which present two or more sites at which either (a) attachment to two or more different antigens can occur or (b) attachment to two or more different epitopes on the same antigen can occur. An example of a multispecific construct could be a heterobihead. A multispecific construct is multivalent.

Suitably, the polypeptides comprised within the construct are antibody fragments. More suitably, the polypeptides comprised within the construct are selected from the list consisting of: a VHH, a VH, a VL, a V-NAR, a Fab fragment and a F(ab')2 fragment. More suitably, the polypeptides comprised within the construct are VHHs.

The polypeptides of the invention can be linked to each other directly (i.e. without use of a linker) or via a linker. Suitably, the linker is a protease-labile or a non-protease-labile linker. The linker is suitably a polypeptide and will be selected so as to allow binding of the polypeptides to their epitopes. If used for therapeutic purposes, the linker is suitably non-immunogenic in the subject to which the polypeptides are administered. Suitably the polypeptides are all connected by non-protease-labile linkers. Suitably the protease-labile linker is of the format $[-(G_4S)_x\text{-BJB'-}(G_4S)_y\text{-}]_z$ wherein J is lysine or arginine, B is 0 to 5 amino acid residues selected from R, H, N, Q, S, T, Y, G, A, V, L, W, P, M, C, F, K or I, B' is 0 to 5 amino acid residues selected from R, H, N, Q, S, T, Y, G, A, V, L, W, M, C, F, K or I, x is 1 to 10; y is 1 to 10 and z is 1 to 10. Most suitably J is lysine, B is 0 x is 1, y is 1 and z is 1. Suitably the non-protease-labile linkers are of the format $(G_4S)_x$. Most suitably x is 6.

Vectors and Hosts

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses. adenoviruses and adeno-associated viruses), which serve equivalent functions, and also bacteriophage and phagemid systems. The invention also relates to nucleotide sequences that encode polypeptide sequences or multivalent and/or multispecific constructs. The term "recombinant host cell" (or simply "host cell"), as used herein, is intended to refer to a cell into which a recombinant expression vector has been introduced. Such terms are intended to refer not only to the particular subject cell but to the progeny of such a cell.

In one aspect of the invention there is provided a vector comprising the polynucleotide encoding the polypeptide or construct of the invention or cDNA comprising said polynucleotide. In a further aspect of the invention there is provided a host cell transformed with said vector, which is capable of expressing the polypeptide or construct of the invention. Suitably the host cell is a bacterium such as *Escherichia coli* a yeast belonging to the genera *Aspergillus, Saccharomyces, Kluyveromyces, Hansenula* or *Pichia*, such as *Saccharomyces cerevisiae* or *Pichia pastoris*.

Stability

Suitably, the polypeptide or construct of the present invention substantially retains neutralisation ability and/or potency when delivered orally and after exposure to the intestinal tract (for example, after exposure to proteases of the small and/or large intestine and/or IBD inflammatory proteases). Such proteases include enteropeptidase, trypsin, chymotrypsin, and irritable bowel disease inflammatory proteases (such as MMP3, MMP12 and cathepsin). Proteases of, or produced in, the small and/or large intestine include proteases sourced from intestinal commensal microflora and/or pathogenic bacteria, for example wherein the proteases are cell membrane-attached proteases, excreted proteases and proteases released on cell lysis). Most suitably the proteases are trypsin and chymotrypsin.

Suitably the intestinal tract is the intestinal tract of a dog, pig, human, cynomolgus monkey or mouse. The small intestine suitably consists of the duodenum, jejunum and ileum. The large intestine suitably consists of the cecum, colon, rectum and anal canal. Suitably the polypeptide or construct of the invention is substantially resistant to one or more proteases. The intestinal tract, as opposed to the gastrointestinal tract, consists of only the small intestine and the large intestine.

The polypeptide or construct of the present invention substantially retains neutralisation ability when suitably 10%, more suitably 20%, more suitably 30%, more suitably 40%, more suitably 50%, more suitably 60%, more suitably 70%, more suitably 80%, more suitably 90%, more suitably 95%, more suitably 100% of the original neutralisation ability of the polypeptide of the invention or construct is retained after exposure to proteases present in the small and/or large intestine and/or IBD inflammatory proteases.

Suitably the polypeptide or construct of the invention substantially retains neutralisation ability after exposure to proteases present in the small and/or large intestine and/or IBD inflammatory proteases for, for example, up to at least 2, more suitably up to at least 3, more suitably up to at least 4, more suitably up to at least 5, more suitably up to at least 5.5, more suitably up to at least 16, more suitably up to at least 21 or more suitably up to at least 22 hours at 37 degrees C.

Suitably 10% or more, more suitably 20% or more, more suitably 30% or more, more suitably 40% or more, more suitably 50% or more, more suitably 60% or more, more suitably 70% or more of the neutralisation ability of the polypeptide or construct of the invention is retained after 16 hours of exposure to conditions of the intestinal tract, more suitably the small or large intestine, more suitably human faecal extract.

Suitably 10% or more, more suitably 20% or more, more suitably 30% or more, more suitably 40% or more, more suitably 50% or more, more suitably 60% or more, more suitably 70% or more of the neutralisation ability of the polypeptide or construct of the invention is retained after suitably 4, 6 or 16 hours of exposure to mouse small intestinal supernatant.

Suitably 10% or more, more suitably 15% or more, more suitably 20% or more, more suitably 25% or more, more suitably 30% or more, more suitably 35% or more, more suitably 40% or more of the neutralisation ability of the polypeptide or construct of the invention is retained after 16 hours of exposure to mouse small intestinal supernatant.

Suitably 50% or more, more suitably 60% or more, more suitably 65% or more, more suitably 70% or more, more suitably 75% or more, more suitably 80% or more, more suitably 85% or more, more suitably 85% or more of the neutralisation ability of the polypeptide or construct of the invention is retained after 16 hours of exposure to mouse small intestinal supernatant.

Suitably 10% or more, more suitably 20% or more, more suitably 30% or more, more suitably 40% or more, more suitably 50% or more, more suitably 60% or more, more suitably 70% or more of the administered dose of polypeptides or constructs of the invention retain neutralisation ability against TNF-alpha and remain in the faeces of a mouse, cynomolgus monkey and/or human (suitably excreted faeces or faeces removed from the intestinal tract) after 1, 2, 3, 4, 5, 6 or 7 hours of exposure to conditions of the intestinal tract.

A polypeptide of the invention or construct of the present invention remains substantially intact when suitably 10%, more suitably 20%, more suitably 30%, more suitably 40%, more suitably 50%, more suitably 60%, more suitably 70%, more suitably 80%, more suitably 90%, more suitably 95%, more suitably 99%, most suitably 100% of the administered quantity of polypeptide of the invention or construct remains intact after exposure to proteases present in the small and/or large intestine and/or IBD inflammatory proteases.

Suitably, the polypeptide of the invention or construct of the present invention remains substantially intact after exposure to the stomach, duodenum, jejunum or ileum of cynomolgus monkey for 5 hours. Suitably, the polypeptide of the invention or construct of the present invention remains substantially intact after exposure to the caecum or colon of cynomolgus monkey for 16 hours.

Suitably a polypeptide or construct of the present invention substantially retains neutralisation ability when suitably 10%, more suitably 20%, more suitably 30%, more suitably 40%, more suitably 50%, more suitably 60%, more suitably 70%, more suitably 80%, more suitably 90%, more suitably 95%, more suitably 100% of the original neutralisation ability of the polypeptide or construct is retained after freezing and thawing.

Therapeutic Use and Delivery

A therapeutically effective amount of a polypeptide, pharmaceutical composition or construct of the invention, is an amount which is effective, upon single or multiple dose administration to a subject, in neutralising TNF-alpha to a significant extent in a subject. A therapeutically effective amount may vary according to factors such as the disease state, age, sex, and weight of the individual, and the ability of the polypeptide, pharmaceutical composition or construct to elicit a desired response in the individual. A therapeutically effective amount is also one in which any toxic or detrimental effects of the polypeptide of the invention, pharmaceutical composition or construct are outweighed by the therapeutically beneficial effects. The polypeptide or construct of the invention can be incorporated into pharmaceutical compositions suitable for administration to a subject. The polypeptide or construct of the invention can be in the form of a pharmaceutically acceptable salt.

A pharmaceutical composition of the invention may suitably be formulated for oral, intramuscular, subcutaneous or intravenous delivery. The pharmaceutical compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. Solid dosage forms are preferred. The polypeptide of the invention, pharmaceutical composition or construct may be incorporated with excipients and used in the form of ingestible tablets, buccal tablets, troches, capsules, elixirs, suspensions, syrups, wafers, and the like.

Typically, the pharmaceutical composition comprises a polypeptide or construct of the invention and a pharmaceutically acceptable diluent or carrier. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide or construct of the invention. Pharmaceutical compositions may include antiadherents, binders, coatings, disintegrants, flavours, colours, lubricants, sorbents, preservatives, sweeteners, freeze dry excipients (including lyoprotectants) or compression aids.

Most suitably, the polypeptide of the invention, pharmaceutical composition or construct of the invention is administered orally. A key problem with oral delivery is ensuring that sufficient polypeptide, pharmaceutical composition or construct reaches the area of the intestinal tract where it is required. Factors which prevent a polypeptide, pharmaceutical composition or construct of the invention reaching the area of the intestinal tract where it is required include the presence of proteases in digestive secretions which may degrade a polypeptide, pharmaceutical composition or construct of the invention. Suitably, the polypeptide, pharmaceutical composition or construct of the invention are substantially stable in the presence of one or more of such proteases by virtue of the inherent properties of the polypeptide or construct itself. Suitably, the polypeptide or construct of the invention is lyophilised before being incorporated into a pharmaceutical composition.

A polypeptide of the invention may also be provided with an enteric coating. An enteric coating is a polymer barrier applied on oral medication which helps to protect the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers.

These are polymers which are insoluble at the highly acidic pH found in the stomach, but which dissolve rapidly at a less acidic pH. Thus, suitably, the enteric coating will not dissolve in the acidic juices of the stomach (pH ~3), but will do so in the higher pH environment present in the small intestine (pH above 6) or in the colon (pH above 7.0). The pH-dependent release polymer is selected such that the polypeptide or construct of the invention will be released at about the time that the dosage reaches the small intestine.

A polypeptide, construct or pharmaceutical composition of the invention can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilisers, isotonic agents, suspending agents, emulsifying agents, stabilisers and preservatives. Acceptable carriers, excipients and/or stabilisers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as polysorbates, POE ethers, poloxamers, Triton-X, or polyethylene glycol.

A pharmaceutical composition of the invention may be delivered topically to the skin (for example for use in the treatment of an autoimmune disease such as psoriasis or eczema). Such a pharmaceutical composition may suitably be in the form of a cream, ointment, lotion, gel, foam, transdermal patch, powder, paste or tincture and may suitably include vitamin D3 analogues (e.g. calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid. If the pharmaceutical composition of the invention is to be delivered topically for the treatment of psoriasis or eczema, suitably a further substance considered to be effective in treating psoriasis or eczema may be included in the composition such as steroids especially Class 4 or Class 5 steroids such as hydrocortisone (e.g. 1% hydrocortisone cream); cyclosporin or similar macrolide agent or retinoids.

For all modes of delivery, the polypeptide, pharmaceutical composition or construct of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary polypeptide or construct concentrations in a pharmaceutical composition may range from about 1 mg/mL to about 200 mg/ml or from about 50 mg/mL to about 200 mg/mL, or from about 150 mg/mL to about 200 mg/mL.

An aqueous formulation of the polypeptide, construct or pharmaceutical composition of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated polypeptide or construct and/or minimize the formation of particulates in the formulation and/or reduce adsorption. Exemplary surfactants include polyoxyethylensorbitan fatty acid esters (Tween), polyoxyethylene alkyl ethers (Brij), alkyl-phenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the polypeptide or construct of the invention against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the polypeptide of the invention, pharmaceutical composition or construct of the invention are those to produce the desired therapeutic effect. The dosage range required depends on the precise nature of the polypeptide of the invention, pharmaceutical composition or construct, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages of polypeptide of the invention, pharmaceutical composition or construct of the invention are in the range of 50 ng-50 mg per kg, such as 50 ug-40 mg per kg, such as 5-30 mg per kg of body weight. The unit dosage can vary from less than 100 mg, but typically will be in the region of 250-2000 mg per dose, which may be administered daily or more frequently, for example 2, 3 or 4 times per day or less frequently for example every other day or once per week, once per fortnight or once per month.

In one aspect of the invention there is provided the use of the polypeptide, pharmaceutical composition or construct of the invention in the manufacture of a medicament for the treatment of autoimmune disease. In a further aspect of the invention there is provided a method of treating autoimmune disease comprising administering to a person in need thereof a therapeutically effective amount of the polypeptide, pharmaceutical composition or construct of the invention.

The word 'treatment' is intended to embrace prophylaxis as well as therapeutic treatment. Treatment of diseases also embraces treatment of exacerbations thereof and also embraces treatment of patients in remission from disease symptoms to prevent relapse of disease symptoms.

Combination Therapy

A pharmaceutical composition of the invention may also comprise one or more active agents (e.g. active agents suitable for treating the diseases mentioned herein). It is within the scope of the invention to use the pharmaceutical composition of the invention in therapeutic methods for the treatment of autoimmune diseases as an adjunct to, or in conjunction with, other established therapies normally used in the treatment of autoimmune diseases.

For the treatment of IBD (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/IL23 antibodies (e.g., ustekinumab); anti-IL6R antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are infliximab, adalimumab, certolizumab pegol or golimumab.

Hence another aspect of the invention provides a pharmaceutical composition of the invention in combination with one or more further active agents, for example one or more active agents described above.

In a further aspect of the invention, the polypeptide, pharmaceutical composition or construct is administered sequentially, simultaneously or separately with at least one active agent selected from the list above.

Similarly, another aspect of the invention provides a combination product comprising:
(A) a polypeptide, pharmaceutical composition or construct of the present invention; and
(B) one or more other active agents,
wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a polypeptide, pharmaceutical composition or construct of the present invention and another therapeutic agent, in admixture with a pharmaceutically acceptable adjuvant, diluent or carrier.

The invention also encompasses a kit of parts comprising components:
(i) a polypeptide, pharmaceutical composition or construct of the present invention in admixture with a pharmaceutically acceptable adjuvant, diluent or carrier; and
(ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of autoimmune diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Suitably the polypeptide, pharmaceutical composition or construct of the invention is for use as a medicament and more suitably for use in the treatment of an autoimmune and/or inflammatory disease.

Autoimmune Diseases and/or Inflammatory Diseases

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints and skin An inflammatory disease is a disease characterised by inflammation. Many inflammatory diseases are autoimmune diseases and vice-versa.

Autoimmune Diseases and/or Inflammatory Diseases of the GIT

The chronic inflammatory bowel diseases (IBD) Crohn's disease and ulcerative colitis, which afflict both children and adults, are examples of autoimmune and inflammatory diseases of the GIT (Hendrickson et al 2002 *Clin Microbiol Rev* 15(1):79-94, herein incorporated by reference in its entirety). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al 2002 *Clin. Microbiol Rev* 15(1): 79-94, herein incorporated by reference in its entirety). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass. Symptoms associated with gastroduodenal Crohn's disease include early satiety, nausea, emesis, epigastric pain, or dysphagia. Perianal disease is common, along with anal tags, deep anal fissures, and fistulae (Hendrickson et al 2002 *Clin Microbiol Rev* 15(1): 79-94, herein incorporated by reference in its entirety).

In these diseases the TNF-alpha is produced in the lamina propria underlying the gastrointestinal epithelium. This epithelium is disrupted in IBD and facilitates transport of the immunoglobulin chain variable domain into the lamina propria—the site of TNF-alpha production and biological action in these diseases (see Example 8). Other diseases of the GIT include for example the inflammatory disease mucositis (suitably drug- and radiation induced-mucositis) where inflammatory lesions are present in the mucosa disrupting the epithelial tight junctions which also allow the immunoglobulin chain variable domain access to the site of TNF-alpha production. In mucositis the lesions can occur anywhere from mouth to anus and for mouth and oesophagus lesions a mouthwash or cream preparation containing the variable domain may be used. For anal and rectal lesions, suppositories, creams or foams containing the variable domain would be suitable for topical application. The immunoglobulin chain variable domains will be cleared from the lamina propria or other inflammatory sites via absorption into the bloodstream at sites of inflammation or via lympatic clearance and subsequent entry into the bloodstream. The domains will therefore reach the liver via the bloodstream and will be cleared via glomerular filtration in the kidney. There is therefore good rationale that the domains will function therapeutically in diseases such as autoimmune hepatitis, type II diabetes and glomerular nephritis.

Suitably the polypeptide, pharmaceutical composition or construct of the invention is used in the treatment of an autoimmune and/or inflammatory disease of the GI (gastrointestinal) tract where TNF-alpha contributes to the pathology of such disease.

Suitably the polypeptide, pharmaceutical composition or construct of the invention is for use in the treatment of an autoimmune and/or inflammatory disease of the GI tract selected from the list consisting of Crohn's disease, ulcerative colitis, irritable bowel disease, diabetes type II, glomerulonephritis, autoimmune hepatitis, Sjogren's syndrome, celiac disease and drug- or radiation-induced mucositis (most suitably Crohn's disease).

Oral delivery of the immunoglobulin chain variable domain will ideally treat inflammatory diseases where TNF-alpha contributes to at least a proportion of the pathology and the immunoglobulin chain variable domain can access the tissue where the TNF-alpha is biologically active.

Autoimmune Diseases and/or Inflammatory Diseases of the Skin

Psoriasis is a debilitating autoimmune, dermatological, disease. Plaque psoriasis, the most common form of the disease, is characterized by red skin covered with silvery scales. Histologically the picture is one of disordered differentiation and hyperproliferation of keratinocytes within the psoriatic plaque with inflammatory cell infiltrates (Ortonne, 1999 *Brit J Dermatol* 140(suppl 54):1-7). The psoriatic skin lesions are inflammatory, red, sharply delimited plaques of various shapes with characteristic silvery lustrous scaling. The term psoriasis includes psoriasis and the symptoms of psoriasis including erythema, skin thickening/elevation and scaling.

Biological agents of use in the treatment of psoriasis include anti-TNF-alpha therapies (such as monoclonal antibodies against TNF, e.g. adalimumab and infliximab, or TNF-alpha receptor fusion proteins such as etanercept), humanised antibodies to CD11a (efalizumab) or agents which bind to CD2 such as alefacept (thereby blocking the CD2 LFA3 interaction). It should be noted that not all of the biological agents listed here have been approved for use in the treatment of psoriasis.

The polypeptide of the invention may be incorporated into a cream/ointment or other topical carrier for administration to inflammatory skin lesions where TNF-alpha contributes to the pathology of such lesions.

Suitably the polypeptide, pharmaceutical composition or construct of the invention is for use in the treatment of an autoimmune and/or inflammatory disease of the skin selected from the list consisting of pemphigus, psoriasis, eczema and scleroderma.

Suitably the polypeptide, pharmaceutical composition or construct is for use in the treatment of other autoimmune/inflammatory diseases in which TNF-alpha is responsible for a proportion of the pathology observed.

Preparative Methods

Polypeptides of the invention can be obtained and manipulated using the techniques disclosed for example in Green and Sambrook 2012 *Molecular Cloning: A Laboratory Manual* 4$^{th}$ Edition Cold Spring Harbour Laboratory Press.

Monoclonal antibodies can be produced using hybridoma technology, by fusing a specific antibody-producing B cell with a myeloma (B cell cancer) cell that is selected for its ability to grow in tissue culture and for an absence of antibody chain synthesis (Köhler and Milstein 1975 *Nature* 256:495-497 and Nelson et al 2000 *Molecular Pathology* 53(3):111-117, herein incorporated by reference in their entirety).

A monoclonal antibody directed against a determined antigen can, for example, be obtained by:

a) immortalizing lymphocytes obtained from the peripheral blood of an animal previously immunized with a determined antigen, with an immortal cell and preferably with myeloma cells, in order to form a hybridoma, b) culturing the immortalized cells (hybridoma) formed and recovering the cells producing the antibodies having the desired specificity.

Alternatively, the use of a hybridoma cell is not required. Accordingly, monoclonal antibodies can be obtained by a process comprising the steps of:

a) cloning into vectors, especially into phages and more particularly filamentous bacteriophages, DNA or cDNA sequences obtained from lymphocytes especially peripheral blood lymphocytes of an animal (suitably previously immunized with determined antigens), b) transforming prokaryotic cells with the above vectors in conditions allowing the production of the antibodies, c) selecting the antibodies by subjecting them to antigen-affinity selection, d) recovering the antibodies having the desired specificity.

Methods for immunizing camelids, cloning the VHH repertoire of B cells circulating in blood (Chomezynnski and Sacchi 1987 *Anal Biochem* 162:156-159), and isolation of antigen-specific VHHs from immune (Arbabi-Ghahroudi et al 1997 *FEBS Lett* 414:521-526) and nonimmune (Tanha et al 2002 *J Immunol Methods* 263:97-109) libraries using phage, yeast, or ribosome display are known (WO92/01047, Nguyen et al 2001 *Adv Immunol* 79:261-296 and Harmsen et al 2007 *Appl Microbiol Biotechnol* 77(1):13-22). These references are herein incorporated by reference in their entirety.

Antigen-binding fragments of antibodies such as the scFv and Fv fragments can be isolated and expressed in *E. coli* (Miethe et al 2013 *J Biotech* 163(2):105-111, Skerra et al 1988 *Science* 240(4855):1038-1041 and Ward et al *Nature* 1989 341:544-546, herein incorporated by reference in their entirety).

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli* and *S. cerevisiae*, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997 *Anal Biochem* 254(2):157-178, herein incorporated by reference in its entirety), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used (Nambiar et al 1984 *Science* 223:1299-1301, Sakamar and Khorana 1988 *Nucl. Acids Res* 14:6361-6372, Wells et al 1985 *Gene* 34:315-323 and Grundstrom et al 1985 *Nucl. Acids Res* 13:3305-3316, herein incorporated by reference in their entirety). A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma and Eckstein 1998 *Annu Rev Biochem* 67:99-134)

Expression of immunoglobulin chain variable domains such as VHs and VHHs can be achieved using a suitable expression vector such as a prokaryotic cell such as bacteria, for example *E. coli* (for example according to the protocols disclosed in WO94/04678, which is incorporated herein by reference and detailed further below). Expression of immunoglobulin chain variable domains such as VHs and VHHs can also be achieved using eukaryotic cells, for example insect cells, CHO cells, Vero cells or suitably yeast cells such as yeasts belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference and detailed further below).

Specifically, VHHs can be prepared according to the methods disclosed in WO94/04678 using *E. coli* cells by a process comprising the steps of:

a) cloning in a Bluescript vector (Agilent Technologies) a DNA or cDNA sequence coding for the VHH (for example obtained from lymphocytes of camelids or produced synthetically) optionally including a His-tag, b) recovering the cloned fragment after amplification using a 5' primer specific for the VHH containing an XhoI site and a 3' primer containing the SpeI site having the sequence TC TTA ACT AGT GAG GAG ACG GTG ACC TG (SEQ ID NO: 58), c) cloning the recovered fragment in phase in the Immuno PBS vector (Huse et al 1989 *Science* 246 (4935):1275-1281, herein incorporated by reference in its entirety) after digestion of the vector with XhoI and SpeI restriction enzymes, d) transforming host cells, especially *E. coli* by transfection with the recombinant Immuno PBS vector of step c, e) recovering the expression product of the VHH coding sequence, for instance by affinity purification such as by chromatography on a column using Protein A, cation exchange, or a nickel-affinity resin if the VHH includes a His-tag.

Alternatively, immunoglobulin chain variable domains such as VHs and VHHs are obtainable by a process comprising the steps of:

a) obtaining a DNA or cDNA sequence coding for a VHH, having a determined specific antigen binding site, b) amplifying the obtained DNA or cDNA, using a 5' primer containing an initiation codon and a HindIII site, and a 3' primer containing a termination codon having a XhoI site, c) recombining the amplified DNA or cDNA into the HindIII (position 2650) and XhoI (position 4067) sites of a plasmid pMM984 (Merchlinsky et al 1983 *J. Virol.* 47:227-232, herein incorporated by reference in its entirety), d) transfecting permissive cells especially NB-E cells (Faisst et al 1995 *J Virol* 69:4538-4543, herein incorporated by reference in its entirety) with the recombinant plasmid, e) recovering the obtained products.

Further, immunoglobulin chain variable domains such as VHHs or VHs can be produced using *E. coli* or *S. cerevisiae* according to the methods disclosed in Frenken et al 2000 *J Biotech* 78:11-21 and WO99/23221 (herein incorporated by reference in their entirety) as follows:

After taking a blood sample from an immunised llama and enriching the lymphocyte population via Ficoll (a neutral, highly branched, high-mass, hydrophilic polysaccharide which dissolves readily in aqueous solutions—Pharmacia) discontinuous gradient centrifugation, isolating total RNA by acid guanidium thiocyanate extraction (Chomezynnski and Sacchi 1987 *Anal Biochem* 162:156-159), and first strand cDNA synthesis (e.g. using a cDNA kit such as RPN 1266 (Amersham)), DNA fragments encoding VHH and VH fragments and part of the short or long hinge region are amplified by PCR using the specific primers detailed on pages 22 and 23 of WO99/23221. Upon digestion of the PCR fragments with PstI and HindIII or BstEII, the DNA fragments with a length between about 300 and 450 by are purified via agarose gel electrophoresis and ligated in the *E. coli* phagemid vector pUR4536 or the episomal *S. cerevisiae* expression vector pUR4548, respectively. pUR4536 is derived from pHEN (Hoogenboom et al 1991 *Nucl Acid Res* 19:4133-4137, herein incorporated by reference in its entirety) and contains the lacI$^q$ gene and unique restriction sites to allow the cloning of the llama VHH and VH genes. pUR4548 is derived from pSY1 (Harmsen et al 1993 *Gene* 125:115-123, herein incorporated by reference in its entirety). From this plasmid, the BstEII site in the leu2 gene is removed via PCR and the cloning sites between the SUC2 signal sequence and the terminator are replaced in order to facilitate the cloning of the VH/VHHs gene fragments. The VH/VHHs have the c-myc tag at the C-terminus for detection. Individual *E. coli* JM109 colonies are transferred to 96 well microtiter plates containing 150 ml 2TY medium supplemented with 1% glucose and 100 mg L$^{-1}$ ampicillin.

After overnight growth (37 degrees C.), the plates are duplicated in 2TY medium containing 100 mg L$^{-1}$ ampicillin and 0.1 mM IPTG. After another overnight incubation and optionally freezing and thawing, cells are centrifuged and pelleted and the supernatant can be used in an ELISA. Individual *S. cerevisiae* colonies are transferred to test tubes containing selective minimal medium (comprising 0.7% yeast nitrogen base, 2% glucose, supplemented with the essential amino acids and bases) and are grown for 48 h at 30 degrees C. Subsequently, the cultures are diluted ten times in YPGal medium (comprising 1% yeast extract, 2% bacto peptone and 5% galactose). After 24 and 48 h of growth, the cells are pelleted and the culture supernatant can be analysed in an ELISA. Absorbance at 600 nm (0D600) is optionally measured.

Further, immunoglobulin chain variable domains such as VH/VHHs can be produced using *S. cerevisiae* using the procedure as follows:

Isolate a naturally-occuring DNA sequence encoding the VH/VHH or obtain a synthetically produced DNA sequence encoding the VH/VHH, including a 5'-UTR, signal sequence, stop codons and flanked with SacI and HindIII sites (such a synthetic sequence can be produced as outlined above or for example may be ordered from a commercial supplier such as Geneart (Life Technologies)).

Use the restriction sites for transfer of the VH/VHH gene to the multi-copy integration (MCI) vector pUR8569 or pUR8542, as follows. Cut the DNA sequence encoding the VHH optionally contained within a shuttle vector, cassette or other synthetic gene construct and the MCI vector with SacI and HindIII using: 25 ul VHH DNA (Geneart plasmid or MCI vector), 1 ul SacI, 1 ul HindIII, 3 ul of a suitable buffer for double digestion such as NEB buffer 1 (New England Biolabs) overnight at 37 degrees C. Run 25 ul of digested DNA encoding the VHH and 25 ul of digested MCI vector on a 1.5% agarose gel with 1× TAE buffer and then perform gel extraction for example using QIAquick Gel Extraction Kit (Qiagen)). Set-up a ligation of digested MCI vector and digested DNA encoding the VH/VHH as follows: 100 ng vector, 30 ng VHH gene, 1.5 ul 10× ligase buffer, 1 ul T4 DNA ligase, and ddH$_2$O. Then perform ligation overnight at 16 degrees C.

Next transform the *E. coli* cells. For chemical competent XL-1 blue cells, thaw 200 ul heat competent XL-1 blue cells and add 5 ul ligation mix on ice for about 30 minutes followed by heat shock for 90 seconds at 42 degrees C. Then add 800 ul Luria-Bertani low salt medium supplemented with 2% glucose and recover cells for 2 hours at 37 degrees C. Plate cells on Luria-Bertani agar and ampicillin (100 ug/ml) plates and keep overnight at 37 degrees C. For electro competent TG1 *E. coli* cells, use an electroporation cuvette. In the electroporation cuvette: thaw 50 ul electro competent TG1 cells and 1 ul ligation mix on ice for about 15 minutes. Place the cuvette in the holder and pulse. Add 500 ul of 2TY medium and recover cells for 30 minutes at 37 degrees C. Plate 100 ul of cells on Luria-Bertani, agar, containing ampicillin (100 ug/ml) and 2% glucose plates. Keep plates at 37 degrees C. overnight.

After cloning of the VH/VHH gene into *E. coli* as detailed above, *S. cerevisiae* can be transformed with the linearized MCI vector. Before transformation is carried out, some steps are performed: (i) the DNA should be changed from circular to linear by digestion or else the DNA cannot be integrated into the yeast genome and (ii) the digested DNA should be cleaned of impurities by ethanol precipitation. Also, during the transformation process, the yeast cells are made semi-permeable so the DNA can pass the membrane.

Preparation for yeast transformation: perform a HpaI digestion of the midi-prep prepared from the selected E. coli colony expressing the VH/VHH gene as follows. Prepare a 100 ul solution containing 20 ng of midi-prep, 5 ul HpaI, 10 ul of appropriate buffer such as NEB4 buffer (BioLabs), and ddH$_2$O.

Cut the DNA with the HpaI at room temperature overnight. Next perform an ethanol precipitation (and put to one side a 5 ul sample from HpaI digestion). Add 300 ul ethanol 100% to 95 ul HpaI digested midiprep, vortex, and spin at full speed for 5 minutes. Carefully decant when a pellet is present, add 100 ul of ethanol 70%, then spin again for 5 minutes at full speed. Decant the sample again, and keep at 50-60 degrees C. until the pellet is dry. Re-suspend the pellet in 50 ul ddH$_2$O. Run 5 ul on a gel beside the 5 ul HpaI digested sample.

Yeast transformation: prepare YNBglu plates. Use 10 g agar+425 ml water (sterilised), 25 ml filtered 20×YNB (3.35 g YNB (yeast nitrogen base) in 25 ml sterilized H$_2$O) and 50 ml sterile 20% glucose and pour into petri dishes. Pick one yeast colony from the masterplate and grow in 3 ml YPD (Yeast Extract Peptone Dextrose) overnight at 30 degrees C. Next day prepare about 600 ml YPD and use to fill 3 flasks with 275 ml, 225 ml and 100 ml YPD. Add 27.5 ul yeast YPD culture to the first flask and mix gently. Take 75 ml from the first flask and put this in the second flask, mix gently. Take 100 ml from the second flask and put in the third one, mix gently. Grow until reaching an OD660 of between 1 and 2. Divide the flask reaching this OD over 4 Falcon tubes, ±45 ml in each. Spin for 2 minutes at 4200 rpm. Discard the supernatant. Dissolve the pellets in two Falcon tubes with 45 ml H$_2$O (reducing the number of tubes from 4 to 2). Spin for 2 minutes at 4200 rpm. Dissolve the pellets in 45 ml H$_2$O (from 2 tubes to 1). Spin for 2 minutes at 4200 rpm. Gently dissolve the pellets in 5 ml lithium acetate (LiAc) (100 mM), and spin for a few seconds. Carefully discard some LiAc, but retain over half of the LiAc in the tube. Vortex the cells, boil carrier DNA for 5 minutes and quickly chill in ice-water. Add to a 15 ml tube containing: 240 ul PEG, 50 ul cells, 36 uLiAc (1M), 25 ul carrier DNA, 45 ul ethanol precipitated VH/VHH. Mix gently after each step (treat the blank sample the same, only without ethanol precipitated VH/VHH). Incubate for 30 minutes at 30 degrees C., gently invert the tube 3-4 times, then heat shock for 20-25 minutes at 42 degrees C. Spin up to 6000 rpm for a brief time. Gently remove the supernatant and add 250 ul ddH$_2$O and mix. Streak all of it on an YNBglu plate until plates are dry and grow for 4-5 days at 30 degrees C. Finally, prepare YNBglu plates by dividing plates in 6 equal parts, number the parts 1 to 6, inoculate the biggest colony and streak out number 1. Repeat for other colonies from big to small from 1 to 6. Grow at 30 degrees C. for 3-4 days large until colonies are produced. The VH/VHH clones are grown using glucose as a carbon source, and induction of VH/VHH expression is done by turning on the Galactose-7-promoter by adding 0.5% galactose. Perform a 3 mL small scale culture to test the colonies and choose which one shows the best expression of the VH or VHH. This colony is then used in purification.

Purification: the VH/VHH is purified by cation exchange chromatorgraphy with a strong anion resin (such as Capto S). On day 1, inoculate the selected yeast colony expressing the VH/VHH in 5 ml YPD medium (YP medium+2% glucose) and grow the cells in 25 mL sealed sterile tubes at 30 degrees C. overnight (shaking at 180 rpm). On day 2, dilute the 5 ml overnight culture in 50 mL freshly prepared YP medium+2% glucose+0.5% galactose, grow the cells in 250 ml aerated baffled flasks at 30 degrees C. for two nights (shaking at 180 rpm). On day 4, spin the cells down in a centrifuge at 4200 rpm for 20 min. Cation exchange purification step using a strong anion resin: adjust the pH of the supernatant containing the ligand to 3.5. Wash 0.75 ml resin (+/−0.5 mL slurry) per of 50 mL supernatant with 50 mL of ddH$_2$O followed by three washes with binding buffer. Add the washed resin to the supernatant and incubate the suspension at 4 degrees C. on a shaker for 1.5 hours. Pellet the resin-bound VH/VHH by centrifugation at 500 g for 2 minutes and wash it with wash buffer. Decant supernatant and re-suspend the resin with 10 mL of binding buffer. Put a filter in a PD-10 column, pour the resin in the column and let the resin settle for a while, then add a filter above the resin. Wait until all binding buffer has run through. Elute the VH/VHH with 6×0.5 ml elution buffer. Collect the elution fractions in eppendorf tubes. Measure the protein concentration of the 6 eluted fractions with a Nanodrop. Pool the fractions that contain the VHH and transfer the solution into a 3,500 Da cutoff dialysis membrane. Dialyze the purified protein solution against 3 L of PBS overnight at 4 degrees C. On day 5, dialyze the purified protein solution against 2 L of fresh PBS for an additional 2 hours at 4 degrees C. Finally, calculate the final concentration by BCA.

Although discussed in the context of the VH/VHH, the techniques described above could also be used for scFv, Fab, Fv and other antibody fragments if required.

Multiple antigen-binding fragments (suitably VH/VHHs) can be fused by chemical cross-linking by reacting amino acid residues with an organic derivatising agent such as described by Blattler et al *Biochemistry* 24:1517-1524 (herein incorporated by reference in its entirety). Alternatively, the antigen-binding fragments may be fused genetically at the DNA level i.e. a polynucleotide construct formed which encodes the complete polypeptide construct comprising one or more antigen-binding fragments. One way of joining multiple antigen-binding fragments via the genetic route is by linking the antigen-binding fragment coding sequences either directly or via a peptide linker. For example, the carboxy-terminal end of the first antigen-binding fragment may be linked to the amino-terminal end of the next antigen-binding fragment. This linking mode can be extended in order to link antigen-binding fragments for the construction of tri-, tetra-, etc. functional constructs. A method for producing multivalent (such as bivalent) VHH polypeptide constructs is disclosed in WO 96/34103 (herein incorporated by reference in its entirety).

Suitably, the polypeptide of the invention (in particular, a VHH of the invention) can be produced in a fungus such as a yeast (for example, *S. cerevisiae*) comprising growth of the fungus on a medium comprising a carbon source wherein 50-100 wt % of said carbon source is ethanol, according to the methods disclosed in WO02/48382. Large scale production of VHH fragments in *S. cerevisiae* is described in Thomassen et al 2002 *Enzyme and Micro Tech* 30:273-278 (herein incorporated by reference in its entirety).

In one aspect of the invention there is provided a process for the preparation of the polypeptide or construct of the invention comprising the following steps:

i) cloning into a vector, such as a plasmid, the polynucleotide of the invention, ii) transforming a cell, such as a bacterial cell or a yeast cell capable of producing the polypeptide or construct of the invention, with said vector in conditions allowing the production of the polypeptide or construct, iii) recovering the polypeptide or construct, such as by affinity chromatography.

The present invention will now be further described by means of the following non-limiting examples.

EXAMPLES

Example 1: Llama Immunisation, Phage Display, Immunoglobulin Chain Variable Domain Selection and Propagation 1.1 Immunisation Protocol 1

Initially, two llamas (llama 33 and llama 35) each received 3 injections (on days 0, 14 and 28) of soluble human recombinant TNF-alpha (100 ug injected intra-muscularly, after mixing 1:1 with Stimune adjuvant) followed by 2 injections (on days 56 and 70) with THP-1 cells that had been pre-activated by incubation with bacterial lipopolysaccharide to increase membrane TNF-alpha expression ($10^7$ THP-1 cells injected subcutaneously in 1 ml PBS). A final boosting immunisation with both soluble TNF-alpha and activated THP-1 cells was given on day 84 and blood was drawn 9 days later for the isolation of peripheral blood lymphocytes and extraction of RNA for library construction.

1.2 Immunisation Protocol 2

After resting for a period of four months the llamas were re-immunised with two injections a week apart of CHO Flp-In cells that had been engineered to express a non-cleavable trans-membrane form of human TNF-alpha. Blood was drawn two weeks later for the isolation of peripheral blood lymphocytes and RNA extracted for library construction. Serum immune responses to immunisations were assessed for each of the llamas at several time-points by measuring the binding of heavy chain only antibodies to immobilised human TNF-alpha using a plate ELISA format and detection with rabbit polyclonal anti-variable domain serum and donkey anti-rabbit IgG coupled to horseradish peroxidase (HRP). Titration curves obtained showed that each of the llamas had responded to the first round of immunisations giving high titres of TNF-alpha-binding IgG heavy chain antibodies. Raised serum antibody titres were also noted following the second round of immunisations although these were somewhat lower for both animals.

1.3 Phage Library Construction

Blood cells collected from each llama at the end of each immunisation phase were used to generate four separate phage display libraries (#33, #35, #33NEW and #35NEW). Total RNA was extracted from the peripheral blood lymphocytes that were isolated from each of the immunised llamas (llamas 33 and 35). The RNA was then used to generate cDNA using reverse transcriptase and primers or random octameric oligonucleotides. PCR was then performed to amplify specifically the variable domain region of heavy chain only antibodies, using suitable primers. cDNA fragments encoding the variable domain repertoire were cloned into a phagemid vector and the library introduced into E. coli. Phages were rescued from the bacteria containing the libraries by inoculating respectively 40 and 51 ul from the glycerol stock in 50 ml medium containing glucose and ampicillin. When cultures were at log-phase, helper phage was added to infect the cultures and produce phages. Next day, produced phages were precipitated from the culture supernatant using a PEG/NaCl solution. The number of phages was determined by titration of the solution and infecting log-phase E. coli TG1 with the different phage dilutions. The highest dilution still giving rise to formation of colonies was used to calculate the phage titers. For selection on sTNF-alpha, a sterile 96-well (such as Maxisorp) plate was coated overnight at 4 degrees C. with either 1000, 250 or 63 ng/well or PBS only. Next day the wells of the plate were blocked with 4% Marvel in PBS, then the precipitated phages, which were preincubated with 2% marvel/PBS, were added to the wells. After extensive washing with PBS-Tween and PBS, bound phages were eluted either using alkaline pH shock (0.1 M Triethylamine) for 15 minutes and neutralized with 1 M Tris-HCl pH7.5 (total elution), or with competitive elution, using a 10 times excess of the TNF receptor, for two hours. The number of eluted phages was determined by titration of the elutions from the different wells followed by infection of log-phase E. coli TG1. About half of the eluted phages were rescued by infecting log-phase TG1 and selecting in medium containing ampicillin and glucose.

1.4 Library Selections for Phage with Human and Cynomolgous Monkey TNF-Alpha Binding Activity Variable domains with TNF-alpha antagonistic activity were isolated from the four phage display libraries by binding of the phage to human TNF-alpha followed by elution of TNF-alpha-specific variable domains with an excess of soluble TNFR2-Fc fusion protein (etanercept), or by batch elution. A second round of selection was then performed by binding of the eluted human TNF-alpha specific phage to cynomolgus monkey TNF-alpha such that a pool of variable domains with cross-species TNF-alpha-binding activity could be obtained.

1.4.1 First Round Library Selections of Phage Displaying Variable Domains with Human TNF-Alpha Binding Activity Phage libraries were derived from llama 33 and llama 35 in respect of each stage of immunisation (first stage immunisation: Library #33 and Library #35; second stage immunisation: Library #33NEW and Library #35NEW). A first round of selection was performed to isolate phage displaying variable domains with TNF-alpha-binding activity by panning on human TNF-alpha.

Soluble recombinant human TNF-alpha (1000, 250 or 63 ng/well) was coated directly onto wells of a hydrophilised polypropylene microwell (HPM) plate, (for example, Nunc maxisorp) and phages were allowed to attach. After extensive washing, bound phages were collected using either (i) non-selective elution by alkaline pH shock or (ii) by selective displacement of TNF-alpha-bound phages by the addition of TNFR2-Fc (etanercept 100, 25 and 6.3 ug/ml, 2 h).

Library #33 and Library #35—The numbers of phages eluted from control wells (no TNF-alpha and PBS control) were low and for both libraries there were concentration-related enrichments of phages eluted from the wells that had been pre-coated with TNF-alpha, using either of the elution methods. Overall, the enrichments of TNF-binding phage achieved in the first round selections were about 100-fold for both Libraries #33 and #35.

Library #33NEW and Library #35NEW—The number of clones recovered from the first rounds of selection of the libraries prepared from the re-immunised llamas were found to be low. This may have reflected a lower immune response of the llamas to the mTNF-alpha-CHO cells (lower number of TNF-alpha-reactive clones in total) or that the response led to the generation of mTNF-alpha reactive clones but that only a limited number of these cross-reacted with the soluble form of TNF-alpha. Phages eluted in the first round selections with TNFR2-Fc (etanercept) from the wells coated with 1000 ng/ml human TNF-alpha were expanded yielding suspensions with titres of approximately $2\times10^{12}$ phages/ml.

1.4.2 Second Round Selections for Phage Displaying Immunoglobulin Chain Variable Domains with Human and Cynomolgus Monkey TNF-Alpha Binding Activity Library #33 and Library #35—Second round selections were performed by attachment of the selected phages to soluble human or cynomolgus monkey TNF-alpha (500, 125 or 31 ng/well or PBS) that had been pre-adsorbed onto the well surface of a HPM plate. Phages bound to human TNF-alpha were eluted with soluble TNFR2-Fc (50, 12.5 and 3.1 ug/ml respectively) while those bound to cynomolgus monkey TNF-alpha were eluted using alkaline pH shock. Recoveries from the selections on cynomolgus monkey TNF-alpha were lower than those on human TNF-alpha, possibly due to lower frequencies in both libraries of phages expressing variable domains that are cross-reactive with both human and cynomolgus monkey TNF-alpha.

Library #33NEW and Library #35NEW—Second round selections were performed by attachment of the selected phages to soluble cynomolgus monkey TNF-alpha (1000, 250 or 63 ng/well or PBS) that had been pre-adsorbed onto the well surface of a HPM plate. Bound phages were eluted using alkaline pH shock.

Example 2: Primary Evaluation of Periplasmic Supernatants from Randomly Selected Immunoglobulin Chain Variable Domain Clones 2.1 Propagation and Generation of Periplasmic Extracts for Primary Evaluation Phage present in eluates from the first round selections on human TNF-alpha and second round selections on cynomolgus monkey TNF-alpha were used to infect *E. coli* TG1 cells. Colonies were randomly picked (186 clones from Libraries #33 and #35 into master plates M60-M63; 96 clones from Libraries #33NEW and Library #35NEW into master plate M65) and propagated to generate periplasmic supernatants by sequential centrifugation, resuspension in 1× PBS, freeze-thaw fracture and centrifugation of the propagated cultures (M60-63 and M65 are also referred to as 'MP60-63' and 'MP65', respectively; periplasmic supernatants are also termed periplasmic fractions (PF) or extracts).

The periplasmic extracts were screened to test for their ability to (i) inhibit the binding of soluble human TNF-alpha to TNFR2-Fc in a plate ELISA and (ii) neutralise TNF-alpha-induced cytotoxicity in the fixed concentration L929 assay. In the L929 assay the cytotoxic effect of TNF-alpha (0.5 ng/ml) is considered to be mediated via TNFR1, so variable domains with inhibitory activities in both TNF-alpha-TNFR2-binding and L929 assays are expected to suppress TNF-alpha-responses mediated via either receptor.

2.2.1 Evaluating TNF-Alpha Binding and Neutralising Activity (Master Plates M60-M63)

L929 cytotoxicity and ELISA assays were performed on all 186 periplasmic fractions obtained from clones selected from Library #33 and Library #35. The clones were arranged on 4 master plates M60, M61, M62 and M63 and periplasmic fractions were produced from these master plates. M60-61 contained clones randomly picked from Library #33 and #35. M62-63 contained clones selected from the same libraries after 2 subsequent steps of selection were performed as follows: (i) 10 ug/mL hsTNF-alpha and etanercept for the elution; (ii) hsTNF-alpha (5 ug/mL and 0.3 ug/mL) or cynomolgus sTNF-alpha (5 ug/mL and 0.3 ug/mL) followed by either selective elution with etanercept or complete elution with triethylamine. All the 186 PF were analysed by concentration-independent L929 cytotoxicity assay using resazurin.

2.2.2 Screening of Periplasmic Supernatants by ELISA (Master Plates M60-63)

The TNF-alpha concentration used for screening was 1.25 ng/ml. Periplasmic supernatants were analysed at 1/20 dilution (M60 and M61) or 1/10 dilution (M62 and M63) in 1% BSA. TNF-alpha and periplasmic supernatants were made up at twice the assay concentration, and then mixed together 1:1. Triplicate determinations were carried out for each supernatant. In addition, adalimumab at 10 nM was used as a positive neutralising antibody control. On each ELISA plate, a limited TNF-alpha dose-response (0-5 ng/ml) was also incorporated. ELISA plates for analyses of the periplasmic supernatants were coated overnight with 0.7 ug/ml, 50 ul/well etanercept. After washing and blocking, the TNF-alpha—supernatant mixtures were added and incubated for 2 h. ELISAs were developed using the biotinylated polyclonal rabbit anti-human TNF-alpha antibody, for example, BAF210 (R&D Systems) at 0.2 ug/ml followed by mAvidin—HRP and then TMB.

None of the clones on M60 or M61 had any significant TNF-alpha neutralising activity (all clones demonstrated around or less than 10% TNF-alpha neutralisation). In contrast, adalimumab gave near complete inhibition in the ELISA on all plates where it was included. Many of the clones on M62 (derived from library 33) showed good TNF-alpha neutralisation (11 clones achieving 90% or greater neutralisation and 45 clones achieving 50% or greater neutralisation). A few good neutralising clones were also found on M63 (derived from library 35), but the numbers were much lower than from M62, even though the selection methods were identical (2 clones achieving 90% or greater neutralisation and 7 clones achieving 50% or greater neutralisation).

2.2.3 Screening of Periplasmic Supernatants (PS) by Fixed Concentration L929 Cytotoxicity Assay (Master Plates M60-M63)

Materials
L929 cells (10000 cells/well)
human TNF-alpha fixed concentration for the assay: 500 pg/ml
Actinomycin D concentration: 0.75 ug/mL
PS from masterplates M60-M63 diluted in the assay 1:10
Pure anti-TNF-alpha VHH as positive control: 250 nM final concentration
human TNF-alpha short dose-response curve: 500, 125, 31.25, 7.8 pg/ml
incubation times: 24 h
resazurin cell viability reagent
Method 10000 cells/well in 100 ul were plated on day 0 in 96-well micro-plates in DMEM complete medium and incubated over night at 37 degrees C., 5% $CO_2$. On Day 1 dilution plates were set up (with volumes sufficient for triplicates for each point) and in addition each plate contained as controls:

1. DMEM complete+0.01% Triton X-100
2. DMEM complete+0.75 ug/mL Actinomycin D
3. TNF-alpha dose-response curve+0.75 ug/mL Actinomycin D The medium was removed from each well of the microplate and the cells were incubated with 100 ul of DMEM complete containing hTNF-alpha at 500 pg/mL+ 0.75 ug/mL Actinomycin D+PS (1:10) or with 100 ul of the different controls. After 24 h of incubation at 37 degrees C. 5% $CO_2$, 10 ul of resazurin was added to each well and the cells were incubated for 2 h at 37 degrees C. 5% $CO_2$. 50 ul of 3% SDS was subsequently added to each well. The plates were then read on a fluorescent plate reader at Excitation (Ex) 544 nm/Emission (Em) 590 nm.

Results

None of the periplasmic supernatants of M60-61 showed a protective effect on L929 cells against human TNF-alpha. The positive control showed protection against the effect of TNF-alpha, while the irrelevant VHH did not. Multiple periplasmic supernatants from the selected clones of M62-63 showed a protective effect on L929 cells against TNF-alpha (107 clones achieved greater than or equal to 50% survival). The positive control showed TNF-alpha neutralisation (greater than or equal to 100%), while the irrelevant VHH showed less than 10% TNF-alpha neutralisation.

2.3 Evaluating TNF-Alpha Binding and Neutralising Activity (Master Plate M65)

ELISA and L929 cytotoxicity assays were performed on M65 in the same manner as those described above in respect of M60-M63, unless stated otherwise.

2.3.1 Screening of Periplasmic Supernatants by ELISA (Master Plate M65)

M65 periplasmic supernatants of TNF-alpha specific variable domain clones (96 in total) were analysed for inhibition of TNFR-2-TNF-alpha binding by ELISA both immediately on thawing and after 18 h incubation at 37 degrees C.

ELISA plates were coated with 2 ug/ml, 50 ul/well etanercept at 4 degrees C. overnight, washed and then blocked in preparation for incubation with the TNF-alpha-variable domain mixtures. adalimumab was used at 10 nM as a positive control. The anti-TNF-alpha variable domain periplasmic supernatants were initially diluted 1:10 in 1% BSA, then mixed 1:1 with 2.5 ng/ml TNF-alpha and added to ELISA plates. Subsequent processing of ELISAs followed the protocol above described in respect of M60-63.

Twenty eight of the supernatants gave greater than 80% inhibition of TNF-alpha binding, of which 18 retained most or all inhibitory activity after incubation at 37 degrees C.

2.3.2 Screening of Periplasmic Supernatants by L929 Cytotoxicity Assay (Master Plate M65)

The L929 cytotoxicity assay was performed with a total of 96 periplasmic supernatants (PS) obtained from clones selected from 2 phage display libraries (M65—from #33NEW and #35NEW). The clones were picked after performing (i) a first round of selections on hsTNF-alpha (10 ug/mL) etanercept, and TEA for the elution and from (ii) a second round of selections on cynomolgus sTNF-alpha (10 ug/mL) followed by complete elution with triethylamine. All the 96 PS were analysed by L929 cytotoxicity assay using resazurin.

Materials

L929 cells (10000 cells/well)

human TNF-alpha fixed concentration for the assay: 500 pg/ml final concentration Dilution of PS in the assay: 1:10

Pure anti-TNF-alpha VHH as positive control: 250 nM final concentration

M65 supernatants

TNF-alpha short dose-response curve: 500, 125, 7.8 pg/ml incubation time: 22 h

Resazurin cell viability reagent

Method 10000 cells/well in 100 ul were plated on day 0 in 96 wells Costar micro-plates in DMEM complete medium and incubated over night at 37 degrees C. and 5% $CO_2$. On Day 1 dilution plates were set up (with volumes sufficient for triplicates for each point) and in addition each plate contained as controls:

1. DMEM complete+0.01% Triton X-100
2. DMEM complete+0.75 ug/mL Actinomycin D
3. TNF-alpha dose-response curve+0.75 ug/mL Actinomycin D The medium was removed from each well of the microplate and the cells were incubated with 100 ul of DMEM complete containing hTNF-alpha at 500 pg/mL+0.75 ug/mL Actinomycin D+PS (1:10) or with 100 ul of the different controls. After 22 h of incubation at 37 degrees C., 10 ul of resazurin was added to each well and the cells were incubated for 2 h at 37 degrees C., 5% $CO_2$. 50 ul of 3% SDS were subsequently added to each well. The plates were then read using a fluorescent plate reader Ex544 nm/Em590 nm.

Multiple periplasmic supernatants from the selected clones of M65 showed a protective effect on L929 cells against h-TNF-alpha. In 9 clones, the treatment with the periplasmic fractions showed greater than 120% survival of L929 cells. A total of 53 clones out of 96 showed greater than 50% TNF-alpha neutralizing activity in the L929 assay and among them 32 showed nearly complete neutralization.

2.3.3 Resistance to Inactivation by Trypsin and Chymotrypsin

Supernatants (and purified samples) were tested for resistance of the variable domain clones to inactivation by trypsin and chymotrypsin based on the retention of their TNF-binding activity in the TNF-TNFR2 ELISA.

Method

Trypsin and chymotrypsin were dissolved separately (in half of the final volume) in 1 mM Tris-HCl pH 8.0, 20 mM $CaCl_2$ and then mixed together to obtain a final concentration of 3 mg/mL each (3 times the assay concentration). 20 uL of each periplasmic extract was incubated with 10 uL of PBS (not digested) or with 10 uL of 3 mg/mL trypsin+chymotrypsin mix (digested) for 75 min at 37 degrees C. 30 uL of ice-cold 2× protease stop solution (2% BSA, 1× PBS, 5 mM NaETDA, 4 mM AEBSF, 0.6 µM Aprotinin, 260 µM Bestatin, 2 mM EDTA, 28 µM E-64, 2 µM Leupeptin, 1 mM PBSF) were added to each sample, and subsequently 140 uL of 1× PBS, 1% BSA were added to each sample to reach a final 1:10 dilution of the periplasmic extracts. A range of concentrations including a top concentration of 3 uM in 1% BSA was prepared for each purified sample. 10 uL of purified sample was incubated with 10 uL of trypsin and chymotrypsin mix (or PBS for undigested sample) and 10 uL of trypsin/chymotrypsin buffer. The periplasmic and purified samples were stored over-night at −80 degrees C. and tested the next day in the TNFR-2-TNF-alpha ELISA assay. ELISA plates were coated with 0.7 ug/ml, 50 ul/well etanercept overnight, washed and then blocked in preparation for incubation with the TNF-alpha-variable domain samples. TNF-alpha variable domain samples were mixed 1:1 with 5 ng/ml h-TNF-alpha (to obtain a TNF-alpha assay concentration of 2.5 ng/mL and samples diluted 1:20) and 50 uL of each sample were added to the ELISA plates. After incubation at 4 degrees C., ELISA plates were washed and incubated with 0.2 ug/mL of biotinylated polyclonal rabbit anti-h-TNF-alpha antibody for 1 h at RT. The ELISA plates were then washed, incubated with 1:1000 modified-avidin-HRP conjugate (mAvidin-HRP) (mAvidin, for example, ExtrAvidin® (Sigma) is a modified form of egg white avidin that retains the high affinity and specificity of avidin for biotin, but does not exhibit the nonspecific binding at physiological pH that has been reported for avidin) for 1 h at RT, washed again, and 100 uL of TMB ELISA substrate were added to each sample. After 30 min the reaction was stopped with 50 uL of 0.5M $H_2SO_4$ and the ELISA plates were read for absorbance at 450 nm.

Results 11 variable domains (Q65B1-Q65F6) were from periplasmic supernatants and 4 variable domains (Q62F2-Q62F11) were from purified samples. 10 variable domains in periplasmic supernatant and 2 purified variable domains were found to have good or excellent trypsin and chymotrypsin resistance. 10 of these variable domains were later found to belong to the same family (Family 1, see part 2.4 below) and 2 of these variable domains were later found to belong to the same family (Family 2, see part 2.4 below). Q62F11, which belongs to neither Family 1 nor Family 2, was not protease resistant. The result with Q62F10 is thought to be due to experimental error (FIG. 1).

2.4 Primary Evaluation Summary

M62 and M63: Of the 186 clones originally picked, 52 of the periplasmic supernatants showed greater than or equal to 50% neutralisation of human soluble TNF-alpha in the L929 cell cytotoxicity assay as well as greater than or equal to 50% inhibition of TNF-alpha-TNFR2 binding activity in the ELISA assay. A sequence analysis performed on 25 of the variable domain clones with greatest neutralising activities showed that these could be grouped into families. Representative clones were selected from the different family groups. The variable domain DNA sequences were re-cloned for high-level expression in *E. coli* and the purified variable domains generated for more detailed evaluation studies.

M65: Of the 96 clones originally picked, 53 of the periplasmic supernatants showed greater than 50% neutralising activity against human soluble TNF-alpha in the L929 cell cytotoxicity assay as well as greater than or equal to 50% inhibition of TNF-alpha-TNFR2 binding activity in the ELISA assay, with 32 showing nearly complete neutralization in both assays. To identify the most stable clones, the periplasmic supernatants (96 in total) were analysed for inhibition of TNFR-2-TNF-alpha binding by ELISA both immediately on thawing and after 18 h incubation at 37 degrees C. Eighteen of the supernatants retained most or all of the TNFR-2-TNF-alpha binding inhibitory activity. The most active periplasmic supernatants (28/96) were then selected to test for inhibition of cynomolgus monkey TNF-induced L929 cell cytotoxicity. A sequence analysis performed on 36 of the variable domain clones with greatest TNF-alpha neutralising activities and resistance to proteases showed that these could be grouped with the M62 and M63 derived variable domains into families. Representative M65 derived clones were selected from the different family groups. The variable domain DNA sequences were re-cloned for expression in *E. coli* and the purified variable domains generated for more detailed evaluation studies.

Example 3: Evaluation of Purified *E. coli* Recombinant Variable Domains 3.1 Production of Selected Variable Domain Clones in *E. coli*

DNA sequences of the variable domains selected from M62, M63 and M65 were re-cloned for production in *E. coli* and then the expressed variable domains were purified as follows.

Selected variable domains were subcloned from the phagemid vector into the expression plasmid pMEK222 (pMEK222 is a gene3 deleted version of the phagemid pUR8100, and where the cloned variable domain is followed by c-myc and 6His tags, two stop codons and the M13 terminator sequence (see WO2013/064701)). The variable domain genes were digested with SfiI and Eco91I and ligated into pMEK222 cut with the same restriction enzymes. *E. coli* strain BL21 DE3 was transformed by the ligations and plated on LB-agar plates supplemented with ampicillin and 2% glucose. Transformants were screened using colony PCR. Amplifications using the primers M13.rev (SEQ ID NO: 81) and M13.fw (SEQ ID NO: 82) led to the generation of plasmids containing inserts of 700 by and of ~350 by (empty plasmids) observed by PCR.

Variable domains were produced from pMEK222 by inoculation of a fresh overnight grown culture at 1/100 dilution in 800 ml 2× YT, 0.1% glucose and 100 ug/ml ampicillin and grown for 2 h at 37 degrees C. Subsequently, 1 mM isopropyl beta-D-1-thiogalactopyranoside (IPTG) was added and the culture was grown for an additional 5 h at 37 degrees C. Bacteria were harvested by centrifugation and resuspended into 30 mL PBS. Bacteria were frozen by incubation at −20 degrees C. overnight. Bacteria were thawed at room temperature and fractionated by centrifugation. To the soluble fraction, which contains the variable domain, $Co^{2+}$ agarose beads, for example, Talon resin (Thermo Scientific) were added to bind His-tagged variable domain. After washing the beads, bound variable domains were eluted with PBS supplemented with 150 mM imidazole. Finally, fractions containing the variable domains were dialyzed against PBS to remove the imidazole.

TNF-alpha-neutralising activities of the purified variable domains were evaluated in several in vitro assay systems to assess efficacy against soluble and membrane forms of human TNF-alpha and soluble cynomolgus monkey TNF-alpha.

3.2 Inhibition of TNF-Alpha-Induced Cytotoxicity of L929 Cells

The assay of variable domains with TNF-alpha-neutralising activity was carried out using an L929 murine cell line and a biological read-out based on the induction of cytotoxicity by soluble human (or cynomolgus monkey) TNF-alpha. L929 cells (10000 cells/well) were cultured for 24 h in the presence of soluble TNF-alpha (500 pg/ml) and actinomycin (0.75 ug/mL) together with dilutions of the purified variable domains. At the end of the experiment cytotoxicity was determined using resazurin. The inhibition of soluble human TNF-induced cytotoxicity of mouse L929 cells was tested to determine TNF-alpha neutralising activity of each of the *E. coli* recombinant Q62, Q63 and Q65 series variable domains against human and cynomolgus monkey TNF.

3.2.1 Purified Immunoglobulin Chain Variable Domains Selected from M62 and M63

Materials

L929 cells (10000 cells/well)

Sterile polypropylene 96-well plates h-TNF-alpha fixed concentration for the assay: 500 pg/ml Actinomycin D concentration: 0.75 ug/mL Purified variable domains (from MP 62-63) including Q62F2, Q62F11, Q62E10, Q62F10

Range of dilutions of the purified variable domains: 300 nM-5 µM (1:3 dilutions)

human-TNF-alpha dose-response curve: 3 ng/mL-0.5 pg/mL

Cynomolgus monkey TNF-alpha dose-response curve: 10 ng/mL-0.2 pg/mL

Adalimumab dose-response curve: 10 nM-0.5 µM incubation times: 22 h

Resazurin cell viability reagent

Method 10000 cells/well in 100 ul were plated on day 0 in 96 wells micro-plates in DMEM complete medium and stored over night at 37 degrees C. and 5% $CO_2$. On Day 1 dilution plates were set up (with volumes sufficient for triplicates for each point) and in addition the plates contained as controls:

1. DMEM complete+0.75 ug/mL Actinomycin D
2. DMEM complete+0.75 ug/mL Actinomycin D+0.5 ng/mL h-TNF-alpha
3. DMEM complete+0.01% Triton (only in the plate containing Cyno-TNF-alpha dose response)
4. DMEM complete (only in the plate containing Cyno-TNF-alpha, h-TNF-alpha and adalimumab dose responses)

The medium was removed from each well of the microplates and the cells were incubated with 100 ul of each variable domain dilution or with 100 ul of the different controls. After 22 h of incubation at 37 degrees C. and 5% $CO_2$, 10 ul of resazurin were added to each well and the cells were incubated for 2 h at 37 degrees C. 50 ul of 3% SDS were subsequently added to each well. The plates were then read using a fluorescent plate reader Ex544 nm/Em590 nm.

3.2.2 Purified Immunoglobulin Chain Variable Domains Selected from M65

Materials

L929 cells (10000 cells/well)

Sterile polypropylene 96-well plates

DMEM

Human TNF-alpha concentration: 500 pg/ml

Cynomolgus monkey TNF-alpha concentration: 500 pg/ml

Actinomycin D concentration: 0.75 ug/mL

Purified variable domains from M65 including Q65D1, Q65D3, Q65B1, Q65C7, Q65A3, Q65E12, Q65F6

Range of dilutions of the purified variable domains: 300 nM-5 μM (1:3 dilutions)

Human TNF-alpha and Cynomolgus TNF-alpha dose-response curves: 10 ng/mL-0.5 pg/mL Adalimumab dose-response curve: 10 nM-0.5 μM incubation times: 22 h Resazurin cell viability reagent Method 10000 cells/well in 100 ul were plated on day 0 in 96 wells micro-plates in DMEM complete medium and stored over night at 37 degrees C. and 5% $CO_2$. On day 1 serial dilutions 1:3 (in DMEM+Act.D+TNF) for each purified variable domain were set up (with volumes sufficient for triplicates for each point) starting from a top concentration of 300 nM. For adalimumab the top concentration used was 10 nM.

The following controls were added to the plates:

1. DMEM complete+0.75 ug/mL Actinomycin D
2. DMEM complete+0.75 ug/mL Actinomycin D+0.5 ng/mL of h-TNF-alpha or cyno-TNF-alpha
3. DMEM complete+0.01% Triton (only in the plate containing the TNF-alpha dose responses)
4. DMEM complete (only in the plates containing the TNF-alpha dose responses)

The medium was removed from each well of the microplates and the cells were incubated with 100 ul of each variable domain dilution or with 100 ul of the different controls. After 22 h of incubation at 37 degrees C. and 5% $CO_2$, 10 ul of resazurin was added to each well and the cells were incubated for 2 h at 37 degrees C. 50 ul of 3% SDS was subsequently added to each well. The plates were then read using a fluorescent plate reader Ex544 nm/Em590 nm.

3.2.3 Results of L929 Cytotoxicity Assays

TABLE 1(a)

Anti-TNF-alpha clones derived from M62 and M63: inhibition of human and cynomolgus TNF-induced L929 cell cytotoxicity

| Clone ID | Family | Inhibition of human and cynomolgus TNF-induced L929 cell cytotoxicity EC50 (nM) | |
|---|---|---|---|
| | | Human TNF | Cynomolgus TNF |
| Q62F2 | 1 | 1 | 0.8 |
| Q62F11 | — | 6 | 1.5 |
| Q62E10 | 2 | 0.2 | <0.1 |
| Q62F10 | 2 | 2 | 1.3 |

TABLE 1(b)

Anti-TNF-alpha clones derived from M65: inhibition of human and cynomolgus TNF-induced L929 cell cytotoxicity

| Clone ID | Family | Inhibition of human and cynomolgus TNF-induced L929 cell cytotoxicity EC50 (nM) | |
|---|---|---|---|
| | | Human TNF | Cynomolgus TNF |
| Q65D3 | 1 | 0.15 | 0.1 |
| Q65D1 | 1 | 0.1 | 0.06 |
| Q65B1 | 1 | 0.04 | 0.01 |
| Q65C7 | 1 | 0.15 | 0.03 |
| Q65A3 | 2 | 0.15 | 0.04 |
| Q65E12 | 2 | 4 | 4 |
| Q65F6 | 2 | 1.5 | 1 |
| Adalimumab | | 0.1 | 0.04 |

It can be seen that variable domains belonging to Family 1 generally showed extremely effective inhibition of both human and cynomolgus TNF-alpha-induced cytotoxicity and variable domains belonging to Family 2 also generally showed very effective inhibition of both human and cynomolgus TNF-alpha-induced cytotoxicity. A number of variable domains showed similar performance to adalimumab.

3.3 Inhibition of TNF-TNFR2 Binding Activity (Purified Immunoglobulin Chain Variable Domains Selected from M65)

Maxisorb plates were coated with etanercept (50 ul/well of 0.7 ug/ml). Variable domains were diluted and mixed with either human or cynomolgus monkey TNF-alpha (1.25 ng/ml) to allow binding before adding to the ELISA plates. TNF-alpha bound to etanercept was detected with biotinylated rabbit polyclonal anti-TNF-alpha antibody (0.2 ug/ml) and mAvidin-HRP followed by TMB and the level of competition by the variable domain for TNF-alpha binding to etanercept was determined. Particular variable domains were capable of binding to human and cynomolgus monkey TNF-alpha leading to inhibition of TNF-alpha-TNFR2 interactions.

3.3.1 Results of TNF-TNFR2 Binding Activity Assays

TABLE 2(a)

Anti-TNF-alpha clones derived from M62 and M63 - inhibition of human and cynomolgus TNF-alpha binding to TNFR2

| Clone ID | Family | Inhibition of TNF-alpha-TNFR2 binding (ELISA) EC50 (nM) | |
|---|---|---|---|
| | | Human TNF | Cynomolgus TNF |
| Q62F2 | 1 | 0.7 | 1.3 |
| Q62F11 | — | 2.3 | 1.4 |
| Q62E10 | 2 | 0.8 | 1.2 |
| Q62F10 | 2 | 30 | 108 |
| Adalimumab | — | | 0.3 |

TABLE 2(b)

Anti-TNF-alpha clones derived from M65 - inhibition of human and cynomolgus TNF-alpha binding to TNFR2

| Clone ID | Family | Inhibition of TNF-TNFR2 Binding (ELISA) EC50 (nM) | |
|---|---|---|---|
| | | Human TNF | Cynomolgus TNF |
| Q65D3 | 1 | 0.33 | 0.45 |
| Q65D1 | 1 | 0.37 | 0.32 |
| Q65B1 | 1 | 0.29 | 0.45 |
| Q65C7 | 1 | 0.35 | 0.32 |
| Q65A3 | 2 | 1.3 | 1.1 |
| Q65E12 | 2 | 47 | 65 |
| Q65F6 | 2 | 13 | 24 |

It can be seen that variable domains belonging to Family 1 generally showed extremely effective inhibition of both human and cynomolgus TNF-alpha-TNFR2 binding and variable domains belonging to Family 2 also generally showed very effective inhibition of both human and cynomolgus TNF-alpha-TNFR2 binding. A number of variable domains showed similar or better performance to adalimumab.

3.4 Inhibition of Soluble TNF-Alpha-Induced Activation of NF-kB/SEAP HEK-293 Reporter Cells The potencies of selected variable domains were measured initially based on the inhibition of cytotoxicity of soluble TNF-alpha towards murine L929 cells. To confirm that these variable domains were also effective and potent in an assay using human cells, experiments were performed using HEK-293-NF-kB-SEAP reporter cells. NF-kB/SEAP HEK-293 cells are stably transfected with the SEAP (secreted alkaline phosphatase) reporter gene under the transcriptional control of an NF-kB response element. Induction of the reporter gene by soluble human TNF-alpha was confirmed and the ability to inhibit this response by TNF-alpha-neutralising antibodies was demonstrated. In these cells activation of the SEAP reporter gene is dependent on the NF-kB pathway, which is activated by soluble TNF-alpha via cell membrane TNFR1 receptors.

In the first experiment Q65B1 (Family 1), Q65C7 (Family 1), Q62E10 (Family 2) and adalimumab were tested. In the second experiment Q65D3 was compared to Q65B1.

3.4.1 Inhibition by Q65B1, Q65C7, Q62E10 and Adalimumab

Materials
HEK-293 NF-kB/SEAP cells (Imgenex): $3.5 \times 10^4$ cells/well, $2 \times 10^4$ cells/well (ii), $10^4$ cells/well (ii)
sterile 96-well plates
DMEM (Sigma, D6429) supplemented with 10% FBS, Pen/Strep, and 500 ug/mL Geneticin antibiotic (G418, Invitrogen, 10131027)
Human TNF-alpha (Invitrogen, PHC3015) concentration: 2 ng/ml
Purified immunoglobulin chain variable domains Q65B1, Q65C7, Q65D3, Q65E5, Q65E6 and Q62E10
Range of dilutions of immunoglobulin chain variable domains and adalimumab: 500 nM-2 µM; 150 nM-1 µM; (3.5 fold dilutions)
Human TNF-alpha dose-response curves: 10 ng/mL-0.01 ng/mL
Controls in the plates:
  cell medium (CM)
  human soluble TNF-alpha ("hs-TNF-alpha") at 2 ng/ml
  0.01% Triton X-100 (for TNF dose response)
Incubation times: 22.5 h
QuantiBlue medium (InvivoGen): 200 uL
  Supernatant volume tested: (i) 10 uL, (ii) 10 uL and 20 uL
  Time-point reading: 2 h 45 min
BioRad Plate reader (620 nm)

Methods $3.5 \times 10^4$ cells/well of NF-kB/SEAP HEK-293 cells were plated in 100 uL on day 0 in 96-well sterile flat bottom micro-plates and stored over night at 37 degrees C. and 5% $CO_2$. On day 1 serial dilutions (3.5 fold) for each purified immunoglobulin chain variable domain were set up (with volumes sufficient for triplicates) in 100 uL of HEK medium containing 2 ng/mL hs-TNF-alpha. The medium was removed from the assay plates and substituted with 100 uL of each sample dilutions. After 22.5 h at 37 degrees C. and 5% $CO_2$, 10 uL or 20 uL of each supernatant were mixed with 200 uL of pre-warmed Quanti Blue medium (InvivoGen) in a 96 well flat bottom NUNC plate. Following 2 h 45 min of incubation at 37 degrees C. in dark with shaking, the SEAP production was measured with the BioRad plate reader at 620 nm.

Figure 2A:
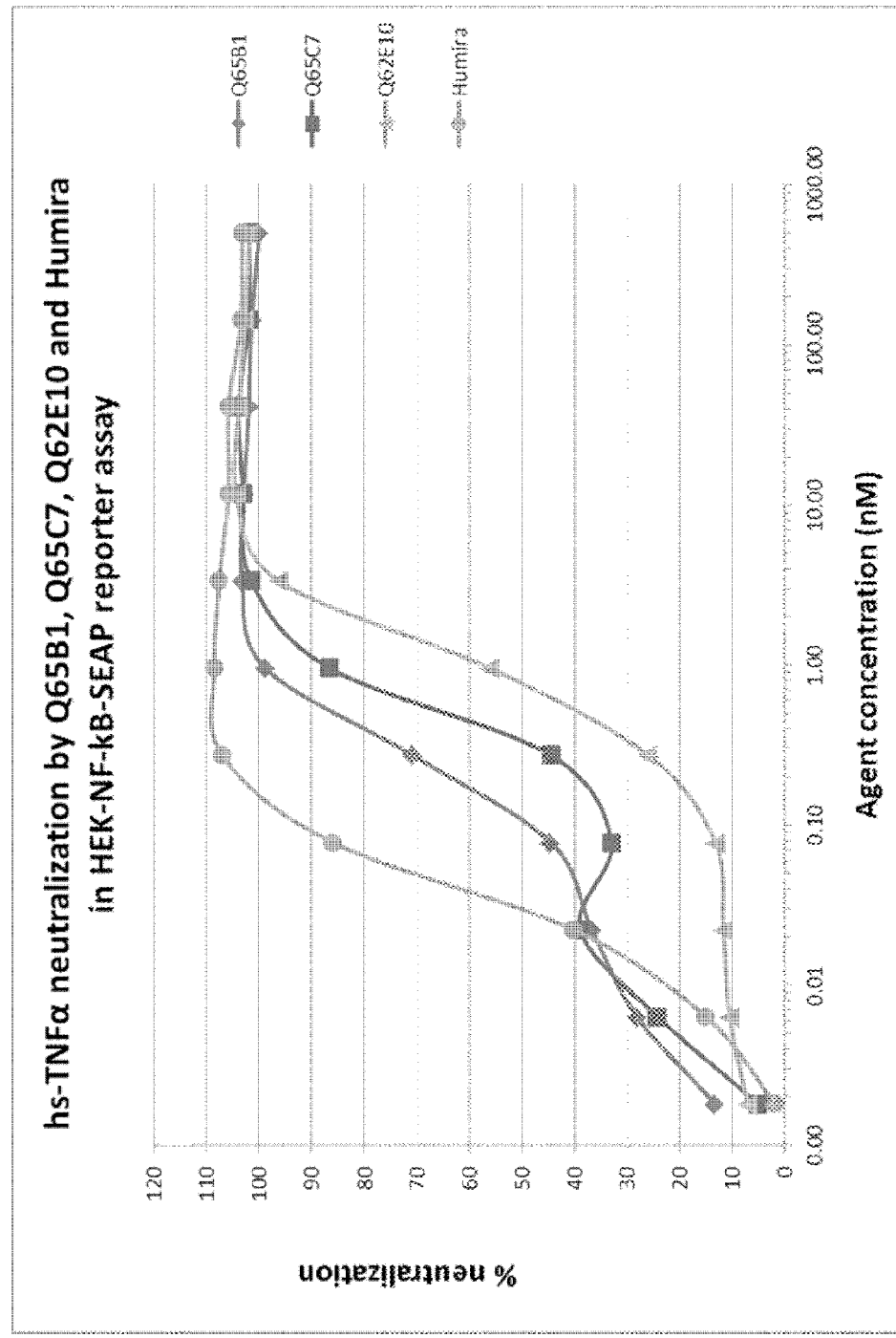

Results showed that Q65B1 (Family 1), Q65C7 (Family 1) and Q62E10 (Family 2), achieved maximal inhibition of induced cell activation induced by soluble human TNF-alpha. Results showed that these immunoglobulin chain variable domains potently and effectively inhibit responses to soluble TNF-alpha mediated via TNFRs expressed on human cells (FIG. 2A).

3.4.2 Inhibition by Q65D3 and Q65B1 (Both Family 1)

Materials and methods were as described above under point 3.4.1, except for different numbers of cells/well ($3.5 \times 10^4$, $2 \times 10^4$, and $1 \times 10^4$) and volumes of cell supernatant after stimulation with TNF (10 uL and 20 uL).

Results

Figure 2B:
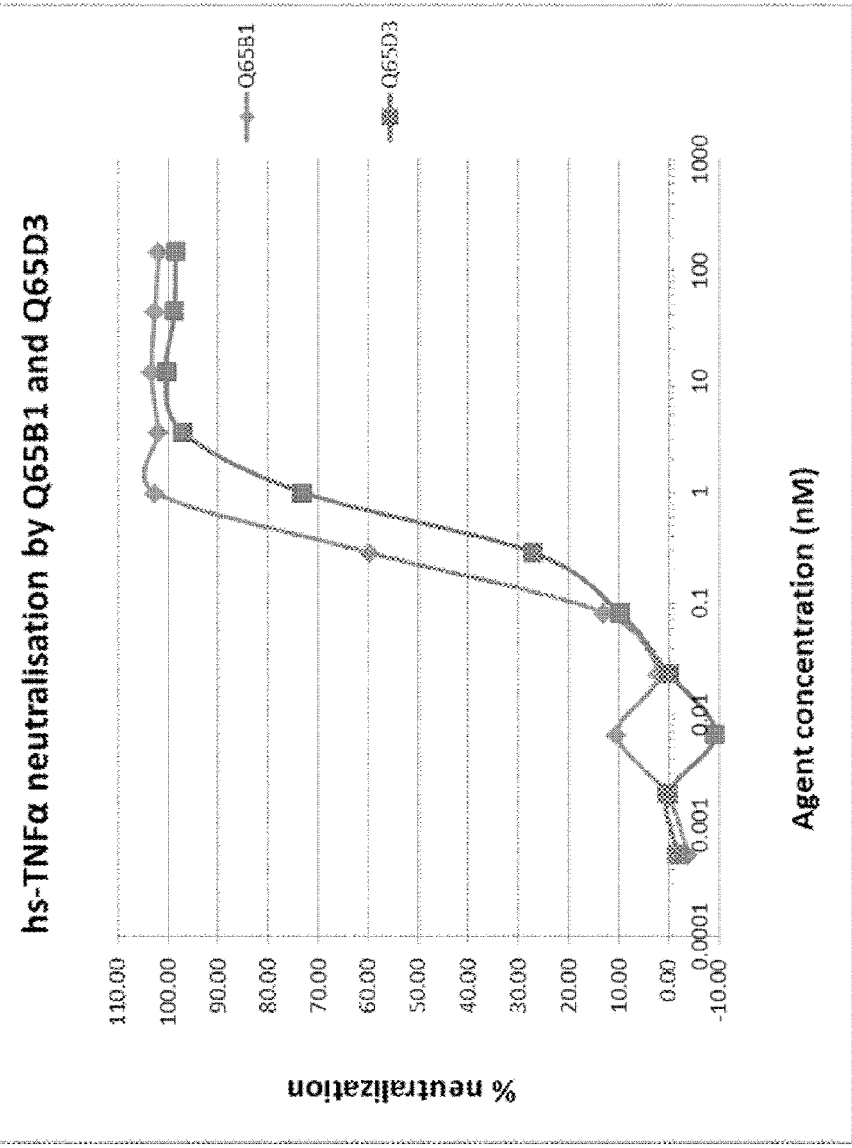

Both Q65B1 and Q65D3 are able to completely neutralize the activity of human soluble TNF-alpha on the HEK-293 NF-kB/SEAP reporter cells, with EC50 values of around 0.2 nM for Q65B1 and 0.6 nM for Q65D3 (FIG. 2B).

3.5 Inhibition of Membrane TNF-Alpha Induced Cell Activation

Both soluble and membrane-bound TNF-alpha can induce activation of cells expressing TNF-alpha-receptors and both forms are considered to contribute to inflammation and pathology in Crohn's disease. Variable domains capable of binding and neutralising both soluble and membrane-bound TNF-alpha activity are likely to be the most effective.

A cell contact reporter assay was developed to ensure that variable domains could be identified with the ability to inhibit membrane-TNF-alpha induced cell activation. A CHO cell line was created that constitutively expresses a non-cleavable transmembrane form of human TNF-alpha (mTNF-alpha-CHO). In co-culture with the NF-kB/SEAP HEK-293 cells, the mTNF-alpha-CHO cells induced activation of the reporter gene. The ability of the different variable domains to inhibit mTNF-alpha induced cell activation could therefore be determined.

3.5.1 Results of Membrane TNF-Alpha Induced Cell Activation Assays

TABLE 3(a)

Anti-TNF-alpha clones derived from M62 and M63 - inhibition of mTNF-alpha-induced NF-kB/SEAP HEK-293 reporter cell activation

| Clone ID | Family | Inhibition of mTNF-alpha-induced HEK-NF-kB SEAP Reporter (EC50 = nM) |
|---|---|---|
| Q62F2 | 1 | 34 |
| Q62F11 | — | 40 |
| Q62E10 | 2 | 80 |
| Q62F10 | 2 | — |
| Adalimumab | | 1-3 |

TABLE 3(b)

Clones derived from M65 - inhibition of mTNF-alpha-induced HEK-NF-kB SEAP reporter cell activation

| Clone ID | Family | Inhibition of mTNF-alpha-induced HEK-NF-kB SEAP Reporter (EC50 = nM) |
|---|---|---|
| Q65D3 | 1 | 16.0 |
| Q65D1 | 1 | 15.3 |
| Q65B1 | 1 | 10.9 |
| Q65C7 | 1 | 14.1 |
| Q65A3 | 2 | 23.9 |
| Q65E12 | 2 | 173.8 |
| Q65F6 | 2 | 109.6 |
| Adalimumab | | 1.2 |

It can be seen that variable domains belonging to Family 1 generally showed effective inhibition of mTNF-alpha and variable domains belonging to Family 2 also generally showed inhibition of mTNF-alpha.

Example 4: Cross-Reactivity with Adalimumab

Adalimumab 1 pg/ml was coated onto HPM plates then incubated with human TNF-alpha in the absence or presence of the different variable domains. After washing to remove free TNF-alpha-variable domain complexes, TNF-alpha remaining bound to the immobilised mAb was detected by incubation with biotinylated rabbit polyclonal anti hTNF-alpha antibody; mAvidin-HRP followed by TMB were then added for ELISA colour development.

Results

Q62E10 (Family 2), Q62F2 (Family 1), Q62F10 (Family 2), Q65A3 (Family 2), Q65B1 (Family 1), Q65C7 (Family 1), Q65D1 (Family 1), Q65D3 (Family 1), Q65E12 (Family 2), Q65F6 (Family 2) and Q62F11 (neither Family 1 nor Family 2), showed complete inhibition of TNF-alpha binding to adalimumab.

Example 5: Stability of Purified E. coli Recombinant Anti-TNF-Alpha Immunoglobulin Chain Variable Domains in Supernatant from Mouse Small Intestine The purified variable domains were tested in the presence of a supernatant extract prepared from the pooled small intestinal contents of several mice. Following incubation of the variable domains in the presence of the intestinal extract for different time periods, TNF-alpha-binding activities of the "digested" variable domain samples were assayed using the h-TNF-alpha-TNFR2 ELISA.

Mouse Small Intestine Supernatants

Mouse small intestines were excised, the solid contents removed and the intestines were rinsed with 1 ml of 0.9% saline. The solid and liquid parts were combined in 1.5 mL microfuge tubes, vortexed to homogeny and centrifuged at 16 k xrcf for 10 minutes at 4 degrees C. The supernatants were removed and stored at −80 degrees C. before use.

Plates and Antigens

The anti-TNF-alpha variable domains were assayed on HPM plates coated with 1 ug/mL etanercept (50 uL/well) overnight at 4 degrees. The plates were blocked with 1% BSA for a minimum of 1 hour before use in the assay.

Protease Stop Solution

Protease inhibitor cocktail tabs were dissolved in 5 mL protease stop buffer (2% BSA, 1× PBS, 5 mM NaEDTA) to make a 20× protease inhibitor stock solution. A 2× protease stop solution (as described in section 2.3.3) was produced by diluting the 20× protease inhibitor solution 1 in 10 with a 1 in 100 dilution of PMSF in protease stop buffer Methods Digests Variable domain stock solutions were prepared in 0.4% BSA at 250 ug/mL. To 55.2 uL of SI supernatant on ice, 4.8 ul of variable domain was added and mixed by vortexing. 25 uL was immediately removed and mixed with 25 uL of ice-cold protease stop solution (undigested control), and frozen at −80 degrees C. A second aliquot of 25 ul was moved to a single well in a polycarbonate thin-walled PCR plate and incubated for 1 to 24 hours at 37 degrees C. (digested variable domain). After incubation, the digested variable domain samples were placed on ice and 25 uL of ice-cold protease stop solution was added to each tube. The samples were frozen at −80 degrees C. before assay.

ELISA

The variable domains were diluted in 1% BSA+1× protease inhibitor solution, made by diluting 20× protease inhibitor stock solution in 1% BSA, and mixed 1:1 with 5 ng/mL h-TNF-alpha. TNF-alpha mix was transferred to the blocked HPM ELISA plates coated with 1 ug/mL etanercept. The plates were incubated for 2 h washed 4× with PBS 0.5% PEG20 (PBST), dried and then incubated with biotinylated rabbit polyclonal anti-human TNF-alpha antibody (50 uL/well, 0.27 ug/mL) for 1 hour with shaking at RT. After 1 h, the plates were washed 4× with PBST, dried by tapping and then incubated with mAvidin-HRP (50 uL/well, 1/1000 dilution) with shaking at RT for 30 min. The plates were then washed with PBST 4×, dried by tapping and developed using 100 uL TMB. Standard curves of the variable domains (in PBS) were run alongside the digested/non-digested samples. The top concentration of the variable domains used in the standard curve and test samples was 300 ng/mL and 200 ng/mL respectively.

Data Analyses

The level of inhibition achieved by the variable domain was calculated by subtracting the signal in the digested and undigested-control variable domains from a TNF-only control (maximal signal). This gave the signal reduction for each variable domain, which is proportional to the amount of variable domain in the sample. The % survival was calculated by dividing the signal reduction of the digested variable domain by the signal reduction of the non-digested variable domain for a single dilution.

Results

62F2 and 65B1 (both Family 1) showed greater than 80% survival, 62E10 showed greater than 70% survival (Family 2), 65D1 and 65C7 (Family 1) showed around 50% survival.

A time course study was then performed to measure performance at 1 h, 3 h and 7 h. The results broadly agreed with the previous small intestinal supernatant work.

Example 6: Optimisation of Selected Anti-TNF-Alpha Immunoglobulin Chain Variable Domains Variable domains investigated so far have not been mutated and purified variable domains have all included C-terminal tags (c-myc-6His or Flag-6His). Mutants were designed to explore whether the modification of N-terminal amino acids, or absence of C-terminal-tags, when combined with mutations to Q65B1, would lead to further increased stability.

6.1 Constructs and Mutations (i) A set of Q65B1 monomer mutants (ID7F-EV, ID8F-EV ID9F-EV, ID13F-EV, ID14F-EV and ID15F-EV; all including His-tags) were designed to investigate the effects of particular mutations on protease resistance.

(ii) A set of bihead constructs (ID22F-ID29F) were designed which included mutated Q65B1 monomer variants and removing His-tags.

(iii) A set of Q65B1 monomer mutants were designed which included mutating the beginning of the sequence to DVQLV and removing His-tags to investigate possibilities for future yeast expression optimisation (DVQLV mutants ID37F and ID38F compared to EVQLV equivalents ID32F (ID32F is ID8F-EV without His-tag) and ID34F, respectively).

Further details of these constructs and mutations are shown in the tables below. Mutations are shown underlined and emboldened relative to the parent Q65B1 monomer sequence.

Details of Constructs and Mutations

| | FR1 | CDR1 | FR2 | CDR2 | FR3 | CDR3 | FR4 |
|---|---|---|---|---|---|---|---|
| ID7F-EV (SEQ ID NO: 41) | EVQLVESGGGLVQPGASLKLSCAASGFDFSSHWMY | | WVRQAPGKELEWLS | EINTNGLITKYGDSVKG | RFTVSANNAANKMYLELTRLEPEDTALYYCAR | NQKGLN | KGQGTQVTVSS |
| ID8F-EV (SEQ ID NO: 42) | EVQLVESGGGLVQPGGSLKLSCAASGFDFSSHWMY | | WVRQAPGKELEWLS | EINTNGLITKYGDSVKG | RFTVSRNNAANKMYLELTRLEPEDTALYYCAR | NQKGLN | KGQGTQVTVSS |
| ID9F-EV (SEQ ID NO: 43) | EVQLVESGGGLVQPGGSLKLSCAASGFDFSSHWMY | | WVRQAPGKELEWLS | EINTNGLITKYGDSVHG | RFTVSANNAANKMYLELTRLEPEDTALYYCAR | NQKGLN | KGQGTQVTVSS |
| ID13F-EV (SEQ ID NO: 44) | EVQLVESGGGLVQPGGSLKLSCAASGFDFSSHWMY | | WVRQAPGKELEWLS | EINTNGLITKYGDSVKG | RFTVSANNAANKMYLELTRLEPEDTALYYCAR | NQHGLN | KGQGTQVTVSS |
| ID14F-EV (SEQ ID NO: 45) | EVQLVESGGGLVQPGGSLKLSCAASGFDFSSHWMY | | WVRQAPGKELEWLS | EINTNGLITKYGDSVKG | RFTVSANNAANKMYLELTRLEPEDTALYYCAR | NQKGLN | HGQGTQVTVSS |
| ID15F-EV (SEQ ID NO: 46) | EVQLVESGGGLVQPGGSLKLSCAASGFDFSSHWMY | | WVRQAPGKELEWLS | EINTNGLITKYGDSVKG | RFTVSANNAANKMYLELTRLEPEDTALYYCAR | NQHGLN | HGQGTQVTVSS |
| ID22F (SEQ ID NO: 47) | EVQLVESGGGLVQPGGSLKLSCAASGFDFSSHWMYGGGGSGGGGSGGGGSGGGGSGGGGS | | WVRQAPGKELEWLS | EINTNGLITKYGDSVKG | RFTVSANNAANKMYLELTRLEPEDTALYYCAR | NQKGLN | KGQGTQVTVSS |
| ID23F (SEQ ID NO: 48) | EVQLVESGGGLVQPGGSLKLSCAASGFDFSSHWMYGGGGSGGGGSGGGGSGGGGSGGGGS | | WVRQAPGKELEWLS | EINTNGLITHYGDSVKG | RFTVSANNAANKMYLELTRLEPEDTALYYCAR | NQKGLN | KGQGTQVTVSS |
| ID24F (SEQ ID NO: 49) | EVQLVESGGGLVQPGGSLKLSCAASGFDFSSHWMYGGGGSGGGGSGGGGSGGGGSGGGGS | | WVRQAPGKELEWLS | EINTNGLITHYGDSVKG | RFTVSANNAANSMYLELTRLEPEDTALYYCAR | NQKGLN | KGQGTQVTVSS |
| ID25F (SEQ ID NO: 50) | EVQLVESGGGLVQPGGSLKLSCAASGFDFSSHWMYGGGGSGGGGSGGGGSGGGGSGGGGS | | WVRQAPGKELEWLS | EINTNGLITHYGDSVKG | RFTVSANNAANSMYLELTRLEPEDTALYYCAR | NQHGLN | KGQGTQVTVSS |

-continued

| | FR1 | CDR1 | FR2 | CDR2 | FR3 | CDR3 | FR4 |
|---|---|---|---|---|---|---|---|
| ID26F (SEQ ID NO: 51) | EVQLVESGGGLVQPGGSLKLSCAASGFDFSSHWMY GGGSGGGGSGGGGSGGGGSLKLSCAASGFDFSSHWMY | | WVRQAPGKELEWLS | EINTNGLITHYGDSVKG | RFTVSRNNAANSMYLELTRLEPEDTALYYCAR | NQHGLN | KGQGTQVTVSS |
| ID27F (SEQ ID NO: 52) | EVQLVESGGGLVQPGGSLKLSCAASGFDFSSHWMY GGGSGGGGSGGGGSGGGGSLKLSCAASGFDFSSHWMY | | WVRQAPGKELEWLS | EINTNGLITHYGDSVKG | RFTVSRNNAANSMYLELTRLEPEDTALYYCAR | NQHGLN | KGQGTQVTVSS |
| ID28F (SEQ ID NO: 53) | EVQLVESGGGLVQPGGSLKLSCAASGFDFSSHWMY GGGSGGGGSGGGGSGGGGSLKLSCAASGFDFSSHWMY | | WVRQAPGKELEWLS | EINTNGLITKYGDSVHG | RFTVSRNNAANKMYLELTRLEPEDTALYYCAR | NQKGLN | KGQGTLVTVSS |
| ID29F (SEQ ID NO: 54) | EVQLVESGGGLVQPGGSLKLSCAASGFDFSSHWMY GGGSGGGGSGGGGSGGGGSLKLSCAASGFDFSSHWMY | | WVRQAPGKELEWLS | EINTNGLITKYGDSVHG | RFTVSRNNAANKMYLELTALEPEDTALYYCAR | NQKGLN | KGQGTLVTVSS |
| ID34F (SEQ ID NO: 56) | EVQLVESGGGLVQPGGSLKLSCAASGFDFSSHWMY | | WVRQAPGKELEWLS | EINTNGLITHYGDSVHG | RFTVSRNNAANKMYLELTRLEPEDTALYYCAR | NQHGLN | KGQGTQVTVSS |
| ID37F (SEQ ID NO: 47) | EVQLVESGGGLVQPGGSLKLSCAASGFDFSSHWMY | | WVRQAPGKELEWLS | EINTNGLITHYGDSVHG | RFTVSRNNAANKMYLELTALEPEDTALYYCAR | NQHGLN | KGQGTQVTVSS |
| ID37F (SEQ ID NO: 47) | DVQLVESGGGLVQPGGSLKLSCAASGFDFSSHWMY | | WVRQAPGKELEWLS | EINTNGLITHYGDSVKG | RFTVSRNNAANKMYLELTRLEPEDTALYYCAR | NQKGLN | KGQGTQVTVSS |
| ID38F (SEQ ID NO: 8) | DVQLVESGGGLVQPGGSLKLSCAASGFDFSSHWMY | | WVRQAPGKELEWLS | EINTNGLITHYGDSVKG | RFTVSRNNAANKMYLELTALEPEDTALYYCAR | NQHGLN | KGQGTQVTVSS |

6.2.1 Effects on Potency and Resistance to Intestinal Proteases (i) ID7F-EV, ID8F-EV ID9F-EV, ID13F-EV, ID14F-EV and ID15F-EV Naïve mouse small intestinal supernatant: the contents of the small intestines from seven C57BL/6 male mice were removed with 0.9% saline, combined, homogenised and centrifuged. The resulting supernatant was removed, aliquoted and frozen.

Human Faecal Supernatant Pool: the faecal samples were turned into slurries with addition of 1× PBS. The slurries were then pooled, centrifuged and the supernatants removed, aliquoted and stored at −80 degrees C. This process removes the faecal matrix, including any cellular material.

The anti-TNF-alpha variable domains were assayed on HPM plates coated with 1 ug/mL etanercept (50 uL/well), overnight. The plates were blocked with 1% BSA for a minimum of 1 hour before use in the assay. A 2× protease stop solution was produced as described in Example 5.

Digests

Variable domain stock solutions at 250 ug/mL were prepared in 0.34% (3400 ug/mL) BSA. To 55.2 uL of faecal or small intestinal supernatant on ice, 4.8 ul of variable domain was added and mixed by vortexing. 25 uL was immediately removed and mixed with 25 uL of ice-cold protease stop solution (undigested control), and frozen at −80 degrees C. Aliquots of 25 ul were placed in wells of a polycarbonate thin-walled PCR plate and incubated for 17 h or 7 h respectively at 37 degrees C. After incubation, the digested variable domain samples were placed on ice and 25 uL of ice-cold protease stop solution was added to each tube. The samples were frozen at −80 degrees C. before assay.

ELISA

The variable domains were diluted in 1% BSA+1× protease inhibition solution as described in Example 5, mixed 1:1 with 5 ng/mL h-TNF-alpha, and incubated at RT for 1 h. The variable domain TNF-alpha mixture was then loaded onto blocked ELISA plates coated with 1 ug/mL etanercept and incubated for 2 hours with shaking at RT. The plates were washed 4× with PBST, dried by tapping and incubated with the biotinylated rabbit anti human-TNF-alpha polyclonal antibody (50 uL/well, 0.3 ug/mL) for 1 hour with shaking at RT. After 1 h, the plates were washed and as before and incubated with mAvidin-HRP (50 uL/well, 1/1000 dilution) with shaking at RT for 30 min. The plates were then washed and dried as before and developed using 100 uL TMB. Standard curves of the variable domains (in PBS) were run alongside the digested/non-digested samples. The top concentration of the variable domains used in the standard curve and test samples was 100 ng/mL.

Data Analyses

After digestion, the variable domain concentrations were measured using the TNFR2-interference ELISA. In this assay, the variable domains are mixed with TNF-alpha. The remaining level of TNF-alpha is then measured. The concentration of variable domain is inferred from the amount of TNF-alpha inhibited from binding the TNFR2 receptor that is bound to the ELISA plate. Raw OD450 values were adjusted with blank readings taken from wells containing 1% BSA only. Standard curves were plotted using Graphpad Prism using non-linear regression to fit four-parameter curves. variable domain concentrations in the test samples were calculated in Graphpad Prism using the standard curve. The % survival was calculated by dividing the average variable domain concentration in the 0-time point wells by the average variable domain concentration for a single time point. The standard error of the ratio of two means was calculated.

Results

Evaluation of the Q65B1 variable domain monomers showed that inclusion of these mutations surprisingly did not greatly affect TNF-alpha neutralisation potency (TNF-alpha-TNFR2 ELISA) of the modified variable domains.

Figure 3:
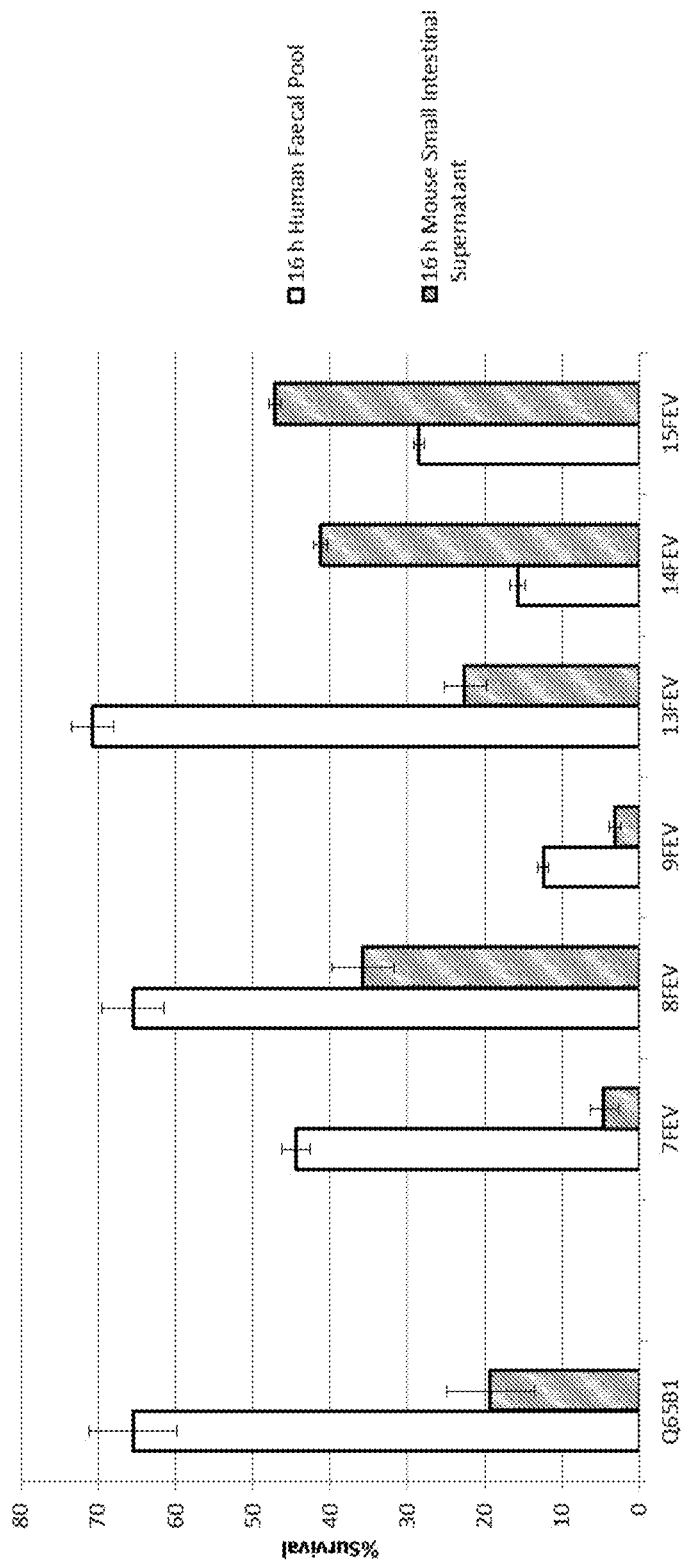
FIG. 3—Immunoglobulin chain variable domains in mouse small intestinal and human faecal digests FIG. 4A—hs-TNF-alpha neutralisation by ID32F, ID34F, Q65B1 and infliximab (first experiment)

ID8F-EV and ID13F-EV showed improved resistance to inactivation by proteases present in mouse intestinal and human faecal supernatant extracts (FIG. 3).

(ii) Constructs ID22F-ID29F

Materials

HEK-293 NF-kB/SEAP cells: $10^4$ cells/well in 50 uL 96-well plates

DMEM supplemented with 10% FBS, Pen/Strep, and 500 ug/mL Geneticin antibiotic (G418)

Human TNF-alpha concentration: 2 ng/ml

Purified homo bi-head variable domains: ID22F-ID29F

Variable domain dilutions: 20 nM-2.1 pM; 2.5 fold dilutions

Incubation time: 23 h

SEAP colourmetric substrate medium: 200 uL; supernatant volume tested: 20 uL; time-point reading: 2 h Plate reader (620 nm)

Methods $10^4$ cells/well of NF-kB/SEAP HEK-293 cells were plated in 50 uL in 96-well flat bottom microplates and incubated overnight at 37 degrees C. and 5% $CO_2$. The following day serial dilutions (2.5 fold) for each purified variable domain were set up at double the assay concentration (with volumes sufficient for triplicates) in 50 uL of HEK medium containing 4 ng/mL hs-TNF-alpha. Variable domains and TNF-alpha were incubated for 1 h at RT and shaken before adding 50 uL of each dilution to the assay plates. After 23 h at 37 degrees C. and 5% $CO_2$, 20 uL of each supernatant were mixed with 200 uL of pre-warmed SEAP medium in 96 well flat bottom plates. Following 2 h incubation at 37 degrees C. in the dark with shaking, the SEAP production was measured with a plate reader at absorbance 620 nm.

Results

The Q65B1 homo-bihead derivatives (including those with changes K59H, K65H, K78S, K101H) were equally potent and effective with EC50 values between 0.02 nM-0.03 nM in the soluble TNF-induced HEK293-NF-kB-SEAP reporter assay. Potency of the Q65B1 homo bihead was increased approximately 10-fold relative to the monomer.

(iii) ID32F, ID34F, ID37F, ID38F

To avoid the possibility of generating a product with a cyclised N-terminal glutamate if expressed in yeast, the effects of changing the N-terminal amino acid of the Q65B1-based variable domain from a glutamic acid to an aspartic acid residue (which is not susceptible to cyclisation) was investigated. Mutants were generated of Q65B1 to produce the corresponding Q65B1 with N-terminal D residue and variants combining each of these with the favourable protease resistance mutations.

sTNF-Alpha Neutralising Ability of ID-32F, ID-34F, ID-37F, and ID-38F Using NF-kB/SEAP HEK-293 Cell Reporter Assay To confirm that ID-38F and ID-34F neutralize soluble human TNF-alpha, these variable domains were tested in the NF-kB/SEAP HEK-293 cellular reporter assay in comparison to the commercial anti-TNF-alpha antibody infliximab (Remicade). Results were obtained from two separate experiments performed on different days.

Materials

HEK-293 NF-kB/SEAP cells (Imgenex): $10^4$ cells/well in 50 uL sterilised 96-well plates DMEM (Sigma, D6429) supplemented with 10% FBS, Pen/Strep, and 500 ug/mL Geneticin antibiotic (G418, Invitrogen, 10131027)

Human TNF-alpha (Invitrogen, PHC3015) concentration: 2 ng/ml 5 purified variable domains: ID-32F, ID-34F, ID-37F, ID-38F and Q65B1 infliximab dilution: 10 nM-1 µM (1st exp); 2 nM-1 pM (2nd exp)

Variable domain dilutions: 10 nM-1 µM (1st exp); 5 nM-1 µM (2nd exp)

Incubation time: 22 h

QuantiBlue medium (InvivoGen): 200 uL; supernatant volume tested: 20 uL; time-point reading: 2 h BioRad Plate reader (620 nm)

Methods $10^4$ cells/well of NF-kB/SEAP HEK-293 cells were plated in 50 uL in 96-well sterilised flat bottom micro-plates and incubated over night at 37 degrees C. and 5% $CO_2$. The following day serial dilutions of variable domains and infliximab (2.5 fold) were set-up at double the assay concentration in HEK medium containing 4 ng/mL hs-TNF-alpha (for Exp 1). In the second experiment serial dilutions (1.9 fold for the variable domain and 2.2 fold for adalimumab) were set up at 4× the assay concentration in 120 uL of HEK medium. 100 uL of each dilution were then diluted 1:1 with 100 uL of HEK medium containing 8 ng/mL hsTNF-alpha (4×) to have variable domains and TNF-alpha at double the assay concentrations. Variable domains and TNF were incubated for 1 h at RT shaking before adding 50 uL of each dilution to the assay plates. After 22 h incubation at 37 degrees C. and 5% $CO_2$, 20 uL of each supernatant were mixed with 200 uL of pre-warmed Quanti Blue medium in 96 well flat bottom NUNC plates. Following 2 h incubation at 37 degrees C. in dark with shaking, the SEAP production was measured with the BioRad plate reader at 620 nm.

Results

Figure 4A:
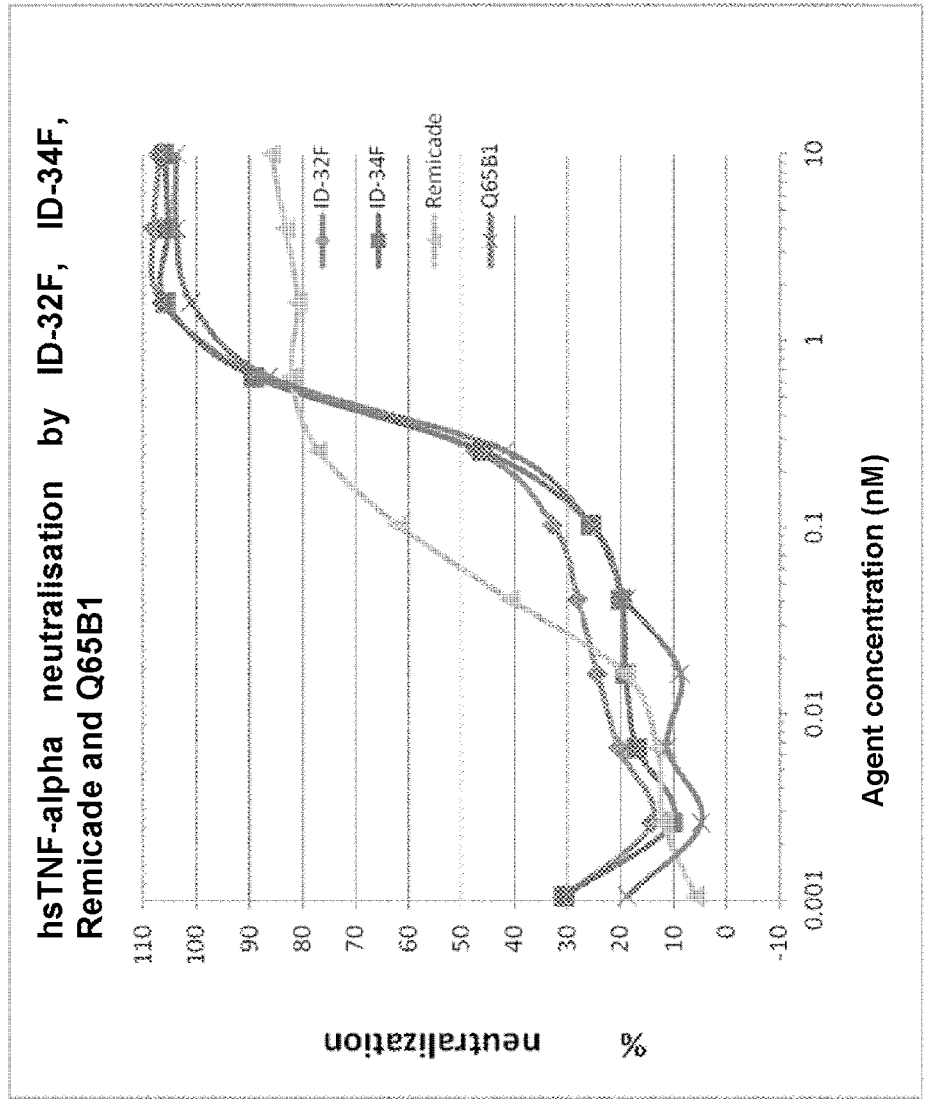
FIG. 4B—hs-TNF-alpha neutralisation by ID32F, ID34F and Q65B1 (second experiment)
FIG. 4C—hs-TNF-alpha neutralization by ID37F, ID38F and Remicade (second experiment)
Figure 4B:
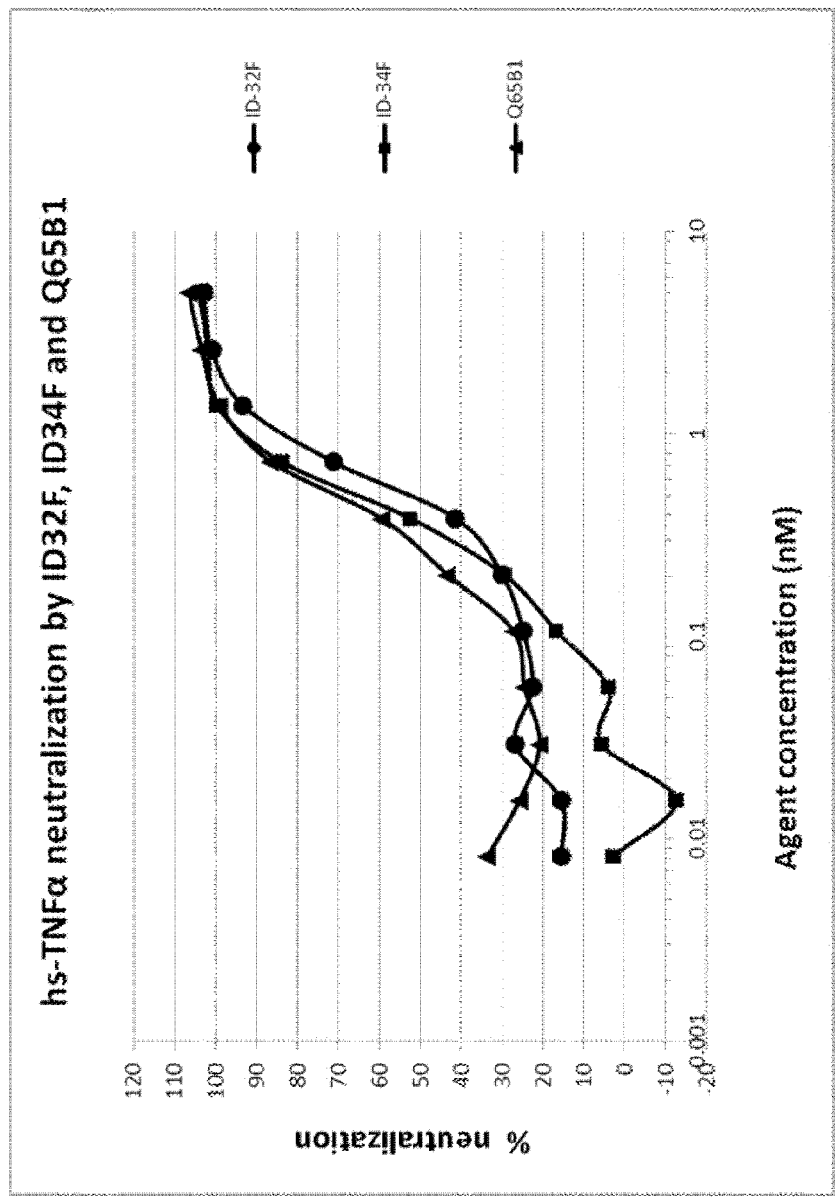
Figure 4C:
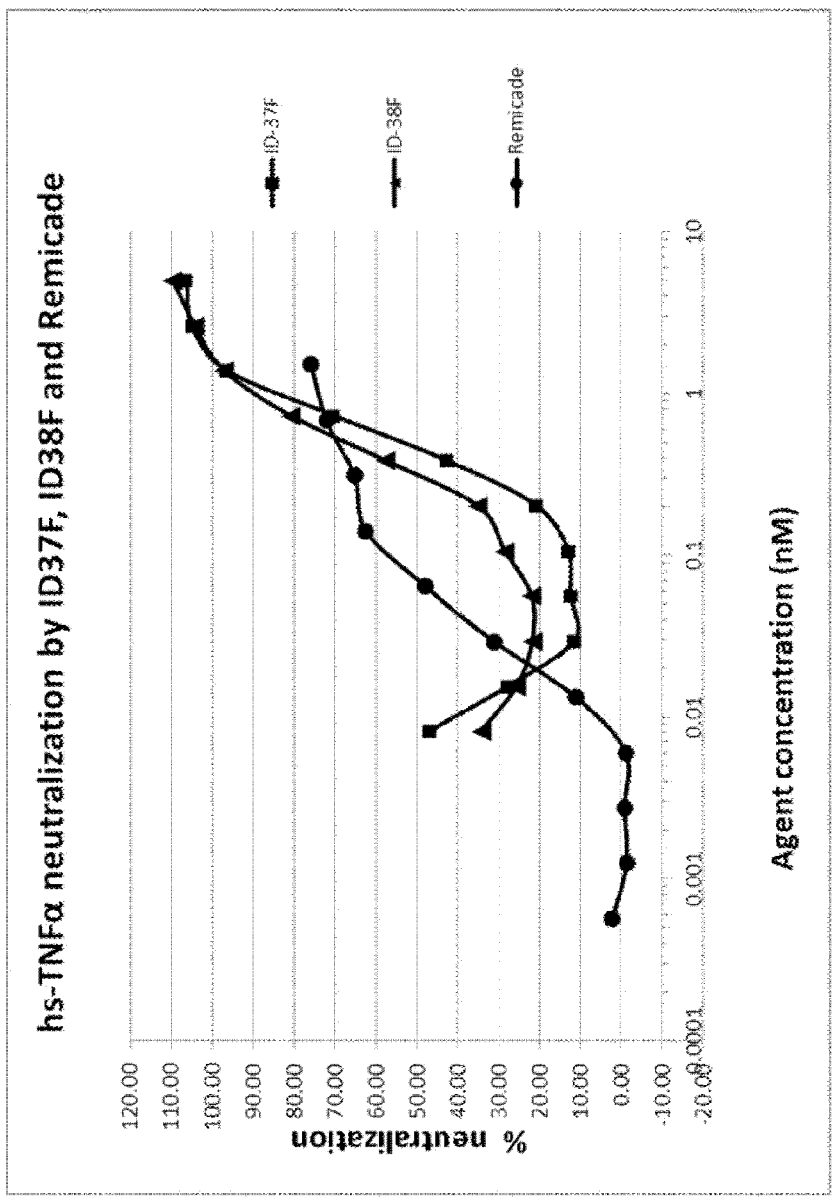

The results of experiment 1 are shown in FIG. 4A and the results of experiment 2 are shown in FIGS. 4B and 4C. All the variable domains show complete sTNF-alpha neutralisation and similar potencies with EC50 values between 0.3 nM and 0.5 nM. It is clear that the addition of the mutations in these variable domains does not affect the potency of these variable domains in neutralising sTNF-alpha. Infliximab does not give a complete sTNF-alpha neutralization in either of the experiments showing nearly plateaued dose-response curves with ~80% maximum neutralization at roughly 2 nM.

mTNF-Alpha Neutralising Activity of ID-34F, ID-38F, Q65B1, ID-8FEV, Adalimumab, and Infliximab Using NF-kB/SEAP HEK-293 Cellular Reporter Assay To confirm that ID-38F and ID-34F neutralize membrane bound TNF-alpha, these variable domains were tested in the NF-kB/SEAP HEK-293 cellular reporter assay in comparison to 2 progenitors (Q65B1 and ID8F-EV). 2 commercial anti-TNF-alpha antibodies (adalimumab and infliximab) were tested in the same assay for reference.

Materials:

NF-kB/SEAP HEK-293 cells (Imgenex) concentration: $3.5 \times 10^4$ cells/well

Stable TNF-alpha_DEL expressing Flp-In CHO Cell Line (Invitrogen & GeneArt, Life Technogies): 25×103 cells/well 2 purified anti-TNF-alpha mutant variable domains: ID-34F and ID-38F 2 purified anti-TNF-alpha variable domains: Q65B1 and ID8F-EV 2 antibodies: adalimumab and infliximab Variable domain/Ab dilutions: 300 nM-0.11 nM (2.2 fold dilutions)

Incubation time: 24 h

QuantiBlue medium (InvivoGen): 200 uL; supernatant volume tested: 10 uL; time-point reading: 2 h BioRad Plate reader (620 nm)

Methods:

$3.5 \times 10^4$ cells/well of NF-kB/SEAP HEK-293 cells in 50 uL were plated on day 0 in 96-wells flat bottom micro-plates and stored over night at 37 degrees C. and 5% $CO_2$. On day 1 serial dilutions for each purified variable domain were set up (with volumes sufficient for triplicates) at three folds the assay concentrations in 50 uL of HEK medium. 50 uL of each variable domain dilution (3×) were added to the assay plates and the plates were then stored at 37 degrees C. and 5% $CO_2$ for 1 h. 50 uL of m-TNF-alpha CHO cells (25000 cells/50 uL) prepared in HEK-medium were added to the HEK-assay plates to have the final variable domain assay concentrations (1×). The cells were incubated for 24 h at 37 degrees C. and 5% $CO_2$. On day 2, 10 uL of each supernatant were mixed with 200 uL of pre-warmed Quanti Blue medium (InvivoGen). After 2 h incubation at 37 degrees C. in dark with shaking, the SEAP production was measured using the BioRad plate reader at 620 nm. The resultant dose response curves were analysed by GraphPad Prism software.

Results

TABLE 4 mTNF-alpha neutralisation by anti-TNF-alpha variable domains and commercial anti-TNF-alpha antibodies

| Variable domain/ antibody | EC50 (nM) |
| --- | --- |
| ID-34F | 4.71 |
| ID-38F | 5.16 |
| Q65B1 | 8.72 |
| ID8F-EV | 7.69 |
| Adalimumab | 3.14 |
| Infliximab | 3.79 |

ID-34F and ID-38F show similar potencies in neutralizing the membrane-bound TNF-alpha indicating that changing the N-terminal amino acid of the variable domain from E to D does not affect the potency of the variable domain. ID-34F and ID-38F seem to be slightly more potent than the parental monomers Q65B1 and ID-8FEV against mTNF. ID-34F and ID-38F are only marginally less potent than the commercial antibodies adalimumab and infliximab in neutralizing mTNF-alpha.

TNFR1 ELISA Comparison of ID38F

As TNFR1 is also thought to play a role in TNF-alpha pathology, an ELISA was performed to test the abilities of ID38F and adalimumab in preventing binding of TNF to TNFR1.

Method

A sterile 96-well microtitre plate was coated with 50 ul 0.5 ug/ml hTNFR1 (R&D Systems) per well overnight at 4 degrees C. Plate was washed in PBST using a plate washer and blocked for 1 hour in 200 ul 1% BSA per well. A threefold dilution series beginning at 30 nM for each antibody was incubated with 2.5 ng/ml TNF-alpha for 1 hour, 50 ul/well of which was then added to the washed plate and incubated for 5 hours. The plate was washed and incubated with 50 ul/well of a 1/1000 dilution of biotinylated rabbit alpha-hTNF (Peprotech P31AB7) in 1% BSA and incubated overnight at 4 degrees C. The plate was washed and incubated with 50 ul/well of a 1/1000 dilution of mAvidin HRP in 1% BSA for 1 hour before a final wash and incubation with 100 ul/well TMB substrate. The reaction was stopped after 20 minutes with 50 ul/well 0.5 M $H_2SO_4$ and absorbance was read at 450 nm. EC50 values were calculated from ELISA data in GraphPad Prism.

Results

TABLE 5

| Anti-TNF agent | EC50 (pM) |
|---|---|
| ID38F | 610.0 |
| Adalimumab | 200.5 |

ID38F is able to neutralise binding of TNF-alpha to TNFR1 at a sub-nanomolar EC50. Higher potency of adalimumab in this assay may reflect the fact that this molecule is divalent while ID38F is monovalent.

TNFR2 ELISA and Stability Assays

Evaluation of the TNF-alpha-binding activities of the variable domain monomers in the TNFR2 ELISA showed that changing the N-terminal amino acid of the variable domain from E to D had no significant effect.

Stabilities of the variable domain monomers were tested as previously by measuring their resistance to inactivation by proteases present in mouse small intestinal and human faecal supernatants. Changing the N-terminal amino acid of the variable domain from E to D had only a very slight effect on protease stability.

6.2.2 Summary

These results have shown that a monomer related to Q65B1, with the N-terminal sequence DVQLV and amino acid changes K59H and K101H ("ID38F"), in particular, has potent TNF-alpha-neutralising activity, excellent resistance to inactivation by small intestinal and faecal proteases and the potential for production of a product that is not susceptible to pyroglutamation if it were to be expressed in yeast.

Example 7: Stability to Intestinal and IBD Inflammatory Proteases 7.1 Evidence of Stability to Proteases Present in Inflamed IBD Tissue Protease activities that can lead to rapid degradation of therapeutic antibodies are up-regulated in Crohn's disease (MMP3, MMP12, cathepsin) (Biancheri et al ECCO, Dublin 2011 Abstract P007, herein incorporated by reference in its entirety)). It was therefore important to investigate the stabilities of anti-TNF-alpha variable domains in the presence of the purified inflammatory proteases and in more complex IBD mucosal tissue lysates.

Recombinant human MMP-3 and recombinant human MMP-12 were obtained from commercial suppliers for example, R&D systems (513-MP-010 and 917-MP-010 respectively). Enzyme activations and 22-hour incubations were conducted in TCNB assay buffer: 50 mM Tris, 10 mM $CaCl_2$, 150 mM NaCl, 0.05% (w/v) polyoxyethylene (23) lauryl ether, for example Brij-35, pH 7.5. MMPs were activated by pre-incubation, prior to use in the main assay. To activate rhMMP-3, the enzyme was diluted to 20 ug/mL in TCNB containing 5 ug/mL chymotrypsin and incubated at 37 degrees C. for 30 minutes. Following activation, chymotrypsin activity was inhibited by the addition of PMSF to a final concentration of 2 mM. PMSF should not affect rhMMP-3 activity adversely. rhMMP-12 was activated by diluting to 50 µg/mL in TCNB and incubating at 37 degrees C. for 30 hours. No further additives or inhibitors were used to activate rhMMP-12.

Materials

Monomer ID34F, bihead ID25F, etanercept, adalimumab and infliximab.

Methods

Test compounds, prepared in TCNB buffer, were mixed with activated rhMMP-3 and rhMMP-12 on ice. Test compounds were present at the beginning of the assay at a concentration of 30 ug/mL. rhMMP-3 was present at a starting assay concentration of 12 ug/mL. rh-MMP-12 was present at a starting assay concentration of 30 ug/mL. Each compound was tested in the presence of both enzymes and a TCNB buffer only control to check for enzyme-independent degradation over the course of the assay. Enzymes were also incubated with TCNB only to provide 'no compound' controls. The final volume of all reactions at t=0 hours=30 uL. At t=0 hours, 10 uL of the starting assay volume was removed and added to 10 uL 2× protease inhibitor solution in protease stop buffer (1× PBS 2% BSA, 5 mM EDTA, as described in Example 5) on ice to stop the reaction. T=0 samples were frozen at −80 degrees C. The remaining 20 uL reaction volumes were sealed in a PCR assay plate and incubated at 37 degrees C. for 22 hours.

Following 22 hour incubation the majority of the reactions were found to be at ~20 uL. 20 uL 2× protease inhibitor solution in protease stop buffer (1× PBS 2% BSA, 5 mM EDTA) was added to stop the reaction. T=22 hr samples were frozen at ~80 degrees C. Assay samples were analysed by Western blotting. Samples were diluted to the equivalent of 6.6 ng/uL test compound in load dye and 15 uL was loaded (100 ng of each test compound/lane, assuming no change in test compound concentration over the course of the experiment) into a 10% Bis-Tris gel. The equivalent volume of the 'no test compound' controls was also loaded. A chemiluminescent MW protein Ladder, for example Super signal (Pierce) was added as a standard at 5 uL/lane. Samples were electrophoresed in SDS-MES buffer and transferred to nitrocellulose membranes using a7 minute transfer program on semi-dry blotting machine, for example, the iBlot. The membranes were blocked overnight at 4 degrees C. in block solution (1% BSA, 2% skim milk powder, 0.05% PEG20, 1× PBS pH7.4). Variable domains were detected using 1) Primary: Rabbit polyclonal anti-Q65B1(-Flag-6His) (terminal bleed serum) at 1/1000 in block solution and 2) Secondary: HRP-conjugated polyclonal Swine-anti-Rabbit IgG antibody at 1/1000 plus 1% normal goat serum) in block solution. Etanercept, Adalimumab and Infliximab were detected using peroxidase-conjugated anti-human IgG specific for Gamma-chains (Dako, P0214) at 1/1000 in block solution (no secondary antibody used). Blots were washed for 6×5 minutes in 25 mL PBST (1× PBS, 0.1% PEG20) between each incubation step to remove non-specifically bound antibody. Pierce Super-Signal ECL (34087) was used to develop the blots, which were visualised using an ImageQuant (LAS4000), varying the exposure time, where necessary.

Results

Figure 5A:
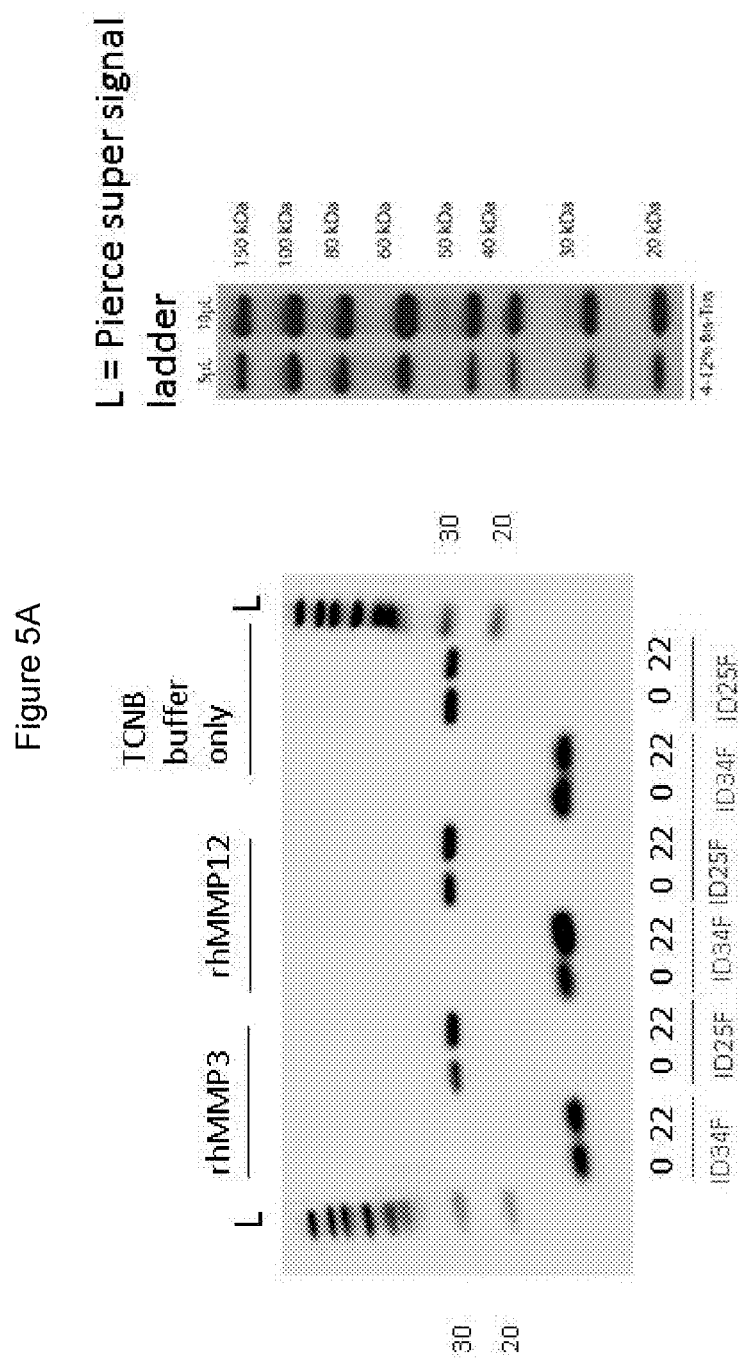
FIG. 5A—Stability of ID34F and ID25F in IBD proteases
Figure 5B:
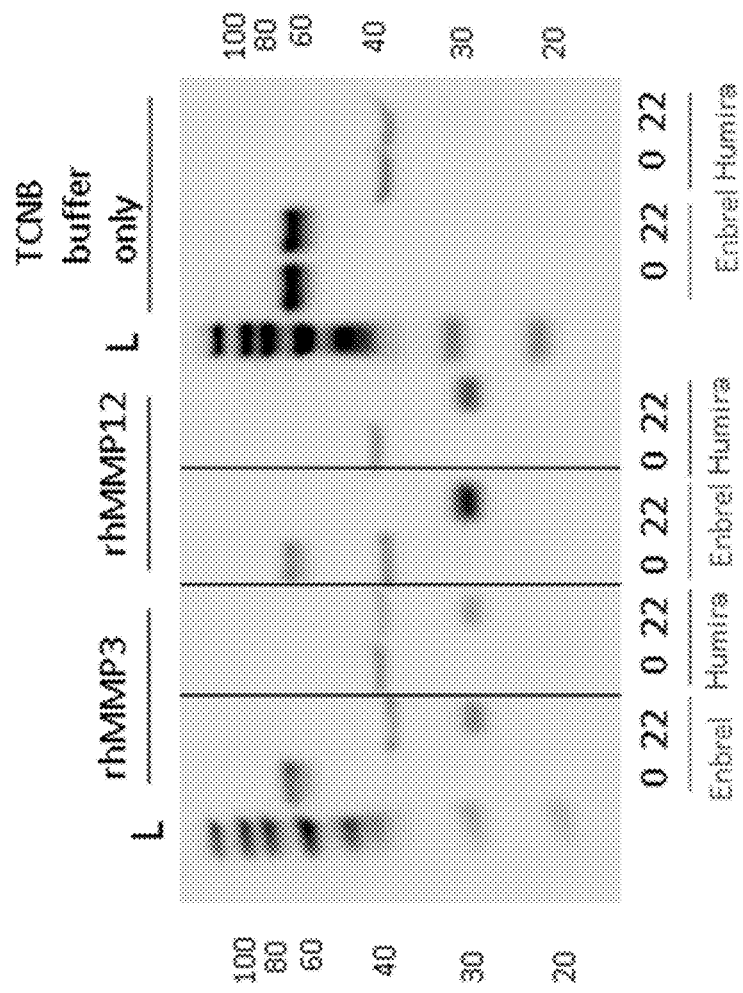
FIG. 5B—Stability of etanercept and adalimumab in IBD proteases
Figure 5C:
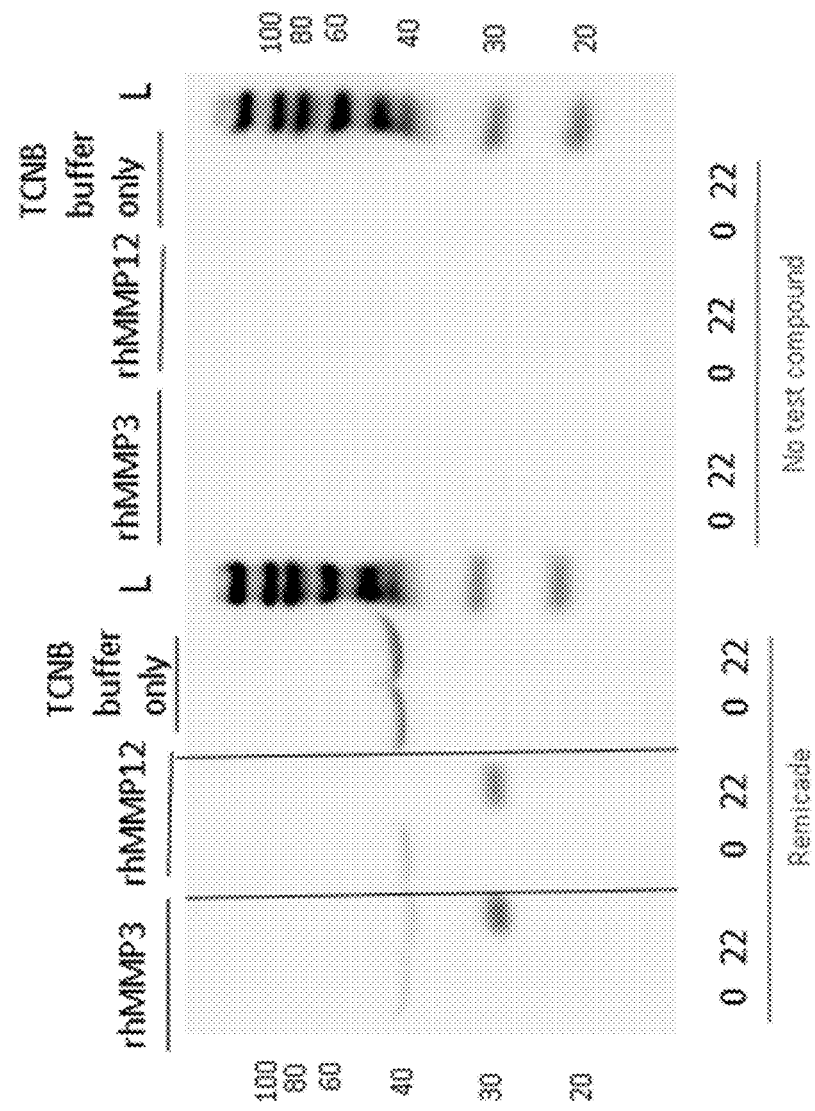
FIG. 5C—Stability of infliximab in IBD proteases

ID34F (Q65B1 K59H and K101H variant) and ID25F (a homobihead of ID34F) appear fully resistant to both rh- MMP3 and rh-MMP12 in vitro after 22 hours incubation (FIG. 5A). By comparison, each of the clinical biological agents Etanercept, Adalimumab, and Infliximab undergo either partial, or total, cleavage of the full-length molecule to generate lower MW fragments (FIGS. 5B and 5C). The analyses show bands corresponding to the monomer (15 kDa) and bihead (30 kDa) that are unchanged following treatment.

7.2 Evidence of Stability in Intestinal Fluids and Faecal Extracts from the Pig and Monkey ID32F, ID34F, ID8F-EV and Q65B1 were each incubated in the presence of supernatants from (a) swine duodenum for 5 and a half hours, (b) mouse small intestine for 5 and a half hours and (c) human faeces for 21 hours. The variable domains tested showed good stability in these extracts from different GI regions. The corresponding approximate % survival for each variable domain were as follows:

TABLE 6

|  | Swine duodenum | Mouse small intestine | Human faeces |
| --- | --- | --- | --- |
| ID32F | 80 | 55 | 40 |
| ID34F | 90 | 70 | 70 |
| ID8F-EV | 120 | 80 | 60 |
| Q65B1 | 90 | 60 | 60 |

7.3 Stability of ID8F-EV in Extracts Prepared from Luminal Contents from Different Regions of the Monkey Gastrointestinal Tract ID8F-EV was incubated for 5 hours in stomach, duodenum, jejunum and ileum supernatants, and for 16 hours in caecum and colon supernatants. After incubation, the % survival of ID8F-EV was between approximately 60% and 90%.

Example 8: Local Delivery of Immunoglobulin Chain Variable Domains to the Intestinal Tract and Access to Lamina Propria Following Oral Administration The variable domains of the invention are unlikely to bind to murine TNF-alpha, however, demonstration of local delivery to the intestinal tract and penetration of the lamina propria following oral administration in a mouse model of IBD provides evidence that neutralisation of TNF-alpha may be achieved at sites of intestinal inflammation.

8.1 Colonic Epithelial Penetration of 65B1 after Ex Vivo Incubation in Lumens of Colon Segments Taken from Normal and DSS Colitis Mice Methods DSS colitis was induced in two mice using a standard protocol. 2% dextran suphate (MP biomedical) was administered in drinking water for 7 days, after which mice were kept for a further 3 days to allow peak development of disease. The mice were then killed, along with 2 normal mice, and the colons removed. Colon luminal contents were gently washed out with PBS, then segments were ligated with thread and processed as shown below. Colon segments were loaded with 3 ug/ml 65B1 in RPMI containing 2% FCS and 15 mM HEPES, then the open segment ends were ligated, and the segments incubated by gently rocking in RPMI+2% FCS+15 mM HEPES in a culture flask at RT for 1.75 h. Colon segments were then cut, washed briefly, and either fixed in paraformaldehyde, or embedded in optimal cutting temperature compound (OCT) and snap frozen. Tissue sections were collected from the proximal colon tissue. 6 um sections were cut and were fixed in ice-cold acetone for 90 seconds. The sections were air dried and stored at −20 degrees C. until assayed. Two serial sections for each mouse were used to stain for each antibody set.

Immunohistochemistry

Slides were thawed and sections were blocked with 3% fatty acid free-BSA in PBS for 30 minutes at room temperature. Primary antibody incubation (either rabbit polyclonal anti variable domain, or a rabbit control polyclonal antibody) was carried out overnight (~18 hours) at 4 degrees C. in a humidified chamber. A set of three slides for each colon tissue block was stained as follows (one slide per treatment):

Vehicle (3% FAF-BSA in PBS as described above)

10 ug/ml affinity purified rabbit polyclonal control antibody 10 ug/ml anti-variable domain affinity purified rabbit polyclonal antibody (AB1219).

After incubation each section was washed three times for three minutes with ice cold-PBS. All sections were stained with a goat ant-rabbit IgG Alexa Fluor 594 antibody at 20 ug/ml (Molecular Probes A11037) and 1 ug/ml Hoescht 33342 (to identify cell nuclei) in vehicle for six hours in the dark at room temperature. Following incubation with secondary antibody, sections were washed as described previously followed by a final wash with Milli Q water. Sections were air dried in the dark, mounted with an antifadant media (Citifluor, AF1) and covered with a glass coverslip. Slides were kept in the dark at 4 degrees C. until viewed. Slides were viewed next day using an Olympus AX70 microscope and images were captured sequentially for each flurochrome (Alexa Fluor 488 and UV) using Image Pro-Plus (v7.0, Media Cybernetics). Exposure levels were set using sections from control or DSS mice treated with the control rabbit antibody polyclonal and at least two random fields of view were captured from each slide from each animal.

Results

In contrast to the images of normal mouse colon, 65B1 associated fluorescence is greatly increased in colon sections from DSS colitis mice. The hematoxylin and eosin (H&E) section revealed extensive inflammation, which presumably severely compromised the epithelial barrier function, allowing ready access of 65B1 to the underlying lamina propria. Whilst there was little or no 65B1 transepithelial penetration in colon segments from normal mice, extensive penetration occurred in the DSS colitis mouse colon segments. The findings suggest that disease induced alterations in epithelial barrier function have allowed the variable domains access to the submucosal tissue.

8.2 Examination of Penetration of 65B1 into the Colonic Mucosa of Normal and DSS Colitis Mice after Oral Gavage Materials and Methods Q65B1 (3.35 mg/ml=222.3 uM)

1M sodium bicarbonate solution

Dried milk (Marvel),

Rabbit anti variable domain antibody, pAB 1219

Control rabbit pAb

Goat anti rabbit Alexa 594 nm (Molecular Probes, A11037)

DSS colitis was induced in 3 C57BL/6 mice by administering 2% dextran suphate (MP biomedical) in drinking water for 7 days, after which mice were kept for a further 3 days to allow peak development of disease. On the day of dosing, all the DSS colitis mice, and 3 normal mice were given 100 ul of 0.1M NaHCO$_3$, 450 mg/ml dried milk, then ~10 minutes later two normal mice and two DSS colitis mice with the most severe disease (as judged by body weight measurements) were given 150 ul of 0.1M NaHCO$_3$ containing 65B1, 33.6 uM final concentration (equivalent to 76 ug) and 450 mg/ml dried milk, whilst the other two mice (one normal and one DSS colitis) received vehicle only. Mice were killed at 3.25-3.5 h post 65B1 dosing, and the gastrointestinal tracts were removed. Colons were isolated, the luminal contents gently squeezed out, then washed briefly in RPMI media containing 2% fetal calf serum, after which they were snap-frozen as described in the enclosed protocol.

Results

Colons from mice that received no 65B1 provided material to establish background fluorescence against which 65B1 specific fluorescence could be judged. VHH associated fluorescence was red whilst the cell nuclei, labelled using Hoechst 33342, were blue. Mouse 1, which received only vehicle, showed the colon background fluorescence, whilst mice 2 and 3 were dosed with 65B1. There is little if any difference in red fluorescence between the colons from the three mice, showing that 65B1 penetration of normal mouse colon is negligible, as expected. The H&E stained section showed a typical colon structure with no obvious inflammation. In contrast to the normal mice, there were areas of extensive inflammation and in some places significant epithelial damage had occurred. There was a clear increase in 65B1 associated fluorescence in the DSS colitis mice receiving the variable domain compared with the DSS colitis mouse receiving vehicle only, indicating transepithelial penetration into the lamina propria.

This result demonstrates that an orally given variable domain can access the colonic submucosa of mice with induced colitis. Access of this compartment in patients with IBD is a necessary prerequisite for therapeutic efficacy.

Example 9: Effects of ID38F and Infliximab on the Phosphorylation of Signalling Proteins Present in Ex Vivo Cultures of IBD Biopsy Tissue Due to antibody-based anti-TNF-alpha therapeutics generally lacking cross-reactivity with, for example, murine TNF-alpha, it has not been possible to assess the efficacy of the immunoglobulin chain variable domains of the present invention in a mouse-based preclinical model of IBD. However, it has been shown that local intestinal delivery of anti-murine TNF-alpha antibody domain-secreting lactobacilli is sufficient to suppress colonic inflammation in a mouse model of IBD (Vandenbroucke et al 2010 Mucosal Immunology 3(1):49-56, herein incorporated by reference in its entirety). Results of these studies provide preclinical validation for the concept of an orally-administered anti-human TNF domain antibody-based approach for the prevention or treatment of IBD.

Infliximab are effective for the treatment of IBD. Infliximab is thought to act primarily by neutralising the biological activity of TNF leading to inhibition of the downstream pro-inflammatory effects of the cytokine. Activation of the many different cell types present in diseased tissue by TNF and secondary inflammatory mediators involves multiple receptor signalling pathways resulting in the phosphorylation of receptors, protein kinases and transcription factors. Experiments have shown that (i) patterns of protein phosphorylation are altered in IBD vs normal intestinal tissue and that (ii) patterns of phosphorylation are sensitive to inhibitors of specific pro-inflammatory mechanisms.

It was investigated (i) whether the TNF-neutralising activity of ID38F can be demonstrated in ex vivo cultures of IBD tissue based on changes in the patterns of tissue protein phosphorylation and (ii) to compare effects of ID38F with the clinically effective anti-TNF mAb infliximab.

Organ Culture

Perendoscopic colonic biopsies or surgical ileal mucosal specimens from patients with active IBD were placed (one biopsy per well) in 24-well plates (VWR International, Lutterworth, UK) in 300 ul serum-free HL-1 medium (Cambrex BioScience, Wokingham, UK) supplemented with 100 U/ml penicillin and 100 ug/ml streptomycin, and cultured at 37 degrees C., 5% $CO_2$ with the following stimuli:

IgG1 10 ug/ml
Infliximab 10 ug/ml
ID38F 4 ug/ml
Control non-anti-TNF-alpha immunoglobulin chain variable domain) 4 ug/ml After 48 h culture, biopsies and supernatants were snap frozen and stored at −70 degrees C.

Phospho-Array Analysis Procedure

For the analysis of phospho-protein content IBD tissue samples were thawed, lysed in RIPA Buffer (Sigma-Aldrich, St. Louis, Mo.) supplemented with phosphatase inhibitor cocktail 2 (Sigma-Aldrich) and protease inhibitor cocktail (Sigma-Aldrich), both at 1%. Protein concentrations of the lysates were determined by the Bio-Rad Protein assay (Bio-Rad Laboratories, Hemel Hempstead, UK) and samples diluted to 1.0 mg/ml in Array Diluent Buffer. Analysis of the phospho-protein profiles was performed using PathScan RTK Signalling Antibody Array Kits (Cell Signaling Technology with chemiluminescent readout #7982). The multiplexed array is a slide-based antibody array founded upon the sandwich immunoassay principle. The array kit allows for the simultaneous detection of 28 receptor tyrosine kinases and 11 important signaling nodes, when phosphorylated at tyrosine or other residues (see Table 7A). Target-specific capture antibodies, biotinylated protein (positive control) and nonspecific IgG (negative control) were spotted in duplicate onto nitrocellulose-coated glass slides. Analysis of the tissue lysates was performed according to the manufacturer's instructions using the reagents provided. Briefly, each diluted lysate was incubated on the slide followed by a biotinylated detection antibody cocktail. Streptavidin-conjugated HRP and LumiGLO® Reagent were then used to visualize the bound detection antibody by chemiluminescence. An image of the slide was captured on standard chemiluminescent sensitive film. An image of the film was obtained by scanning on a HP LaserJet Pro 100 colour scanner and the spot intensities quantified using ImageJ software.

TABLE 7A

Target Kinases and Signalling Proteins Included on the Array

| Receptor Tyrosine Kinases | | Signalling Nodes |
|---|---|---|
| EGFR/ErbB1 pan-Tyr | PDGFR pan-Tyr | Akt/PKB/Rac Thr308 |
| HER2/ErbB2 pan-Tyr | c-Kit/SCFR pan-Tyr | Akt/PKB/Rac Ser473 |
| HER3/ErbB3 pan-Tyr | FLT3/Flk2 pan-Tyr | p44/42 MAPK (ERK1/2) Thr202/Tyr204 |
| FGFR1 pan-Tyr | M-CSFR/CSF-1R pan-Tyr | S6 Ribosomal Protein Ser235/236 |
| FGFR3 pan-Tyr | EphA1 pan-Tyr | c-Abl pan-Tyr |
| FGFR4 pan-Tyr | EphA2 pan-Tyr | IRS-1 pan-Tyr |
| InsR pan-Tyr | EphA3 pan-Tyr | Zap-70 pan-Tyr |
| IGF-IR pan-Tyr | EphB1 pan-Tyr | Src pan-Tyr |
| TrkA/NTRK1 pan-Tyr | EphB3 pan-Tyr | Lck pan-Tyr |
| TrkB/NTRK2 pan-Tyr | EphB4 pan-Tyr | Stat1 Tyr701 |
| Met/HGFR pan-Tyr | Tyro3/Dtk pan-Tyr | Stat3 Tyr705 |
| Ron/MST1R pan-Tyr | Axl pan-Tyr | |
| Ret pan-Tyr | Tie2/TEK pan-Tyr | |

TABLE 7A-continued

Target Kinases and Signalling Proteins Included on the Array

| Receptor Tyrosine Kinases | Signalling Nodes |
|---|---|
| ALK pan-Tyr | VEGFR2/KDR pan-Tyr |

Data Analysis

A "background" signal was measured for each blot and this was subtracted from the uncorrected phospho-protein signals. It was noted that negative values were obtained for some "background-subtracted" phospho-protein values. This was likely due to the method used to read the arrays which involved exposure to X-ray film and scanning of the negative image rather than direct measurement of light output. In cases where the signal measured for a phospho-protein in an ID38F (or infliximab) treated lysate gave a negative value after background correction but the corrected value for the corresponding control non-anti-TNF-alpha immunoglobulin chain variable domain (or IgG) treatment was positive, the level of inhibition was scored as >50%.

Visual assessment of the array data showed that both ID38F and infliximab produced inhibitory effects on some of the phospho-proteins in some of the tissues. To look for effects of the anti-TNF treatments on each of the different phospho-proteins, signals taken from the ID38F and infliximab arrays were compared directly with those from the corresponding control variable domain and IgG arrays and the signal ratios (ID38F/control variable domain and infliximab/IgG) calculated. To assess whether there was a consistent pattern of inhibition by the anti-TNF antibodies in tissues from the different patients, those phospho-proteins that were inhibited by ≥50% in tissues from at least 3 of the 4 CD patients were highlighted (see Table 7B).

TABLE 7B

Phospho-proteins inhibited (>50% in 3 of 4 CD Biopsies) by ID38F or infliximab

| | Phosphoproteins Inhibited (>50% in 3 of 4 IBD Biopsies) | |
|---|---|---|
| Biological Functions | ID38F vs control variable domain | infliximab vs IgG |
| Macrophage apoptotic cell clearance | AXL TYRO3 | AXL — |
| T Cell Signalling/Adhesion | EphA3 Lck | EphA3 ZAP70 |
| Angiogenesis | VEGFR2 TIE2 EphB4 | VEGFR2 TIE2 — |
| Pain/Neuronal Regulation | EphB1 | |
| Cell Activation/Survival/ Signalling | AKT ERK1/2 S6 Ribosomal Protein — | AKT ERK1/2 S6 Ribosomal Protein SRC ALK PDGFR |
| Haematopoiesis | | FLT3 |
| Epithelial Cell Regulation | EphA1 — | EphA1 EphA2 |

Based on these criteria, analysis of the raw array data shows that ID38F treatment consistently inhibited 12/39 phospho-proteins while infliximab inhibited 14/39 phospho-proteins of which 8 were shared with ID38F. Functions of these proteins are all relevant to signaling pathways and immunological processes that are likely to be important in IBD inflammation and/or pathology. When results of the analyses using the "uncorrected" and "control-normalised" data were compared the set of 12 phospho-proteins inhibited by ID38F was the same in both cases; for infliximab, 12 phosphoproteins were identified as common to both analyses.

To further analyse the array data, "control-normalised" values taken from the ID38F and infliximab arrays were compared directly with the "control-normalised" values from the corresponding control variable domain and IgG arrays and the ratios calculated as previously. A consistent pattern of inhibition by the anti-TNF antibodies was again noted based on those phospho-proteins that were inhibited by ≥50% in tissues from at least 3 of the 4 IBD patients (see Table 7C).

TABLE 7C

Phosphoproteins identified by calculation of ratios from array data normalised to the average positive control signal on each array

| | Phosphoproteins Inhibited (>50% in 3 of 4 CD Biopsies) | |
|---|---|---|
| Biological Functions | ID38F vs control variable domain | infliximab vs IgG |
| Macrophage apoptotic cell clearance | AXL TYRO3 | AXL — |
| T Cell Signalling/ Adhesion | EphA3 Lck | EphA3 — |
| Angiogenesis | VEGFR2 TIE2 EphB4 | VEGFR2 TIE2 — |
| Pain/Neuronal Regulation | EphB1 | RET |
| Cell Activation/Survival/ Signalling | AKT ERK1/2 S6 Ribosomal Protein — | AKT ERK1/2 S6 Ribosomal Protein SRC PDGFR |
| Haematopoiesis | | FLT3 cKit |
| Epithelial Cell Regulation | EphA1 — | EphA1 EphA2 |

ID38F treatment inhibited 12/39 phospho-proteins while infliximab inhibited 14/39 phospho-proteins of which 8 were shared with ID38F. When results of the analyses using the "uncorrected" and "control-normalised" data were compared the set of 12 phospho-proteins inhibited by ID38F was the same in both cases; for infliximab, 12 phosphoproteins were identified as common to both analyses.

Conclusion

In cultures of inflamed IBD tissue taken from human patients with active disease, treatment ex vivo with ID38F or with the clinically effective monoclonal antibody infliximab can inhibit the phosphorylation of a set of proteins that include receptor tyrosine kinases and targets involved in cell signaling. Evidence that treatment with structurally different antibodies inhibited the phosphorylation of an almost identical set of 8 proteins in 3 of the 4 tissues strongly suggests that the effects of both antibodies are due to the neutralization of endogenous TNF-driven processes. Inhibition of the set of phospho-proteins by ID38F or infliximab was seen in tissue biopsies taken from at least 3 of the 4 IBD patients. Lack of inhibition of particular phospho-proteins in one of the IBD tissues may have reflected inter-patient differences in disease and/or differences in the cellularity of biopsies taken from different sites of inflammation.

This study provides evidence that the pattern of tissue phosphoproteins inhibited by ID38F is almost identical to that achieved with a clinically relevant concentration of infliximab.

Example 10: Neutralising Potency Comparison of ID38F (a Polypeptide According to the Present Invention) and Anti-TNF-Alpha Polypeptides of the Prior Art The neutralising potency of ID38F was compared in one and the same assay to that of the following anti-TNF-alpha polypeptides of the prior art:

TNF1 (a VHH disclosed in WO2006122786, therein SEQ ID NO: 52)
TNF3 (a VHH disclosed in WO2006122786, therein SEQ ID NO: 60)
TNF30 (a VHH disclosed in WO2006122786, therein SEQ ID NO: 96)
VHH #3E (a VHH disclosed in WO2004041862, therein SEQ ID NO: 4)
Adalimumab (commercially available human monoclonal antibody)

Materials
L929 cells ($10^4$ cells/well)
96-well plates (Costar)
DMEM (Invitrogen) supplemented with Pen/Strep+2 mM L-glutamine
Human TNF-alpha (Invitrogen) concentration: 500 pg/ml
Actinomycin D concentration (Sigma): 0.75 ug/mL
ID38F purified from *S. cerevisiae*
ID38F Flag-His tagged purified from *E. coli*
Adalimumab
TNF1, TNF3, TNF30, VHH #4E purified from *E. coli* with Flag-His tags
Range of dilutions: 5 μM-30 nM (1:3 dilutions)
Incubation times: 23 h
Alamar Blue cell viability reagent (Invitrogen, DAL1100): 10 uL/well
3% SDS
Microplate reader (Fluostar Optima) (OD590 nm)

Method $10^4$ L929 cells/well in 100 ul were plated on day 0 in 96 well micro-plates (Costar) in DMEM complete medium and stored over night at 37° C. and 5% $CO_2$. On day 1 serial dilutions 1:3 (in DMEM+Act.D) for each purified VHH/Ab were set up at doubled the assay concentrations (with volumes sufficient for triplicates) starting from a top concentration of 60 nM. 165 uL of each dilution were then diluted 1:1 with 165 uL of hTNF-alpha 2× (1 ng/mL) prepared in DMEM+Act.D. 0.9 mL of TNF 2× were diluted with 0.9 mL of CM+Act. D to have the TNF only control in the assay. The medium was removed from each well of the assay microplates and the cells were incubated with 100 uL of each TNF+VHH dilution, CM+act. D or TNF only control. After 23 h of incubation at 37° C. and 5% $CO_2$, 10 ul of Alamar Blue were added to each well, the cells were incubated for 2 h at 37° C. and 5% $CO_2$, and 50 ul of 3% SDS were subsequently added to each well. The plates were then read at 590 nm.

Results

Figure 6:
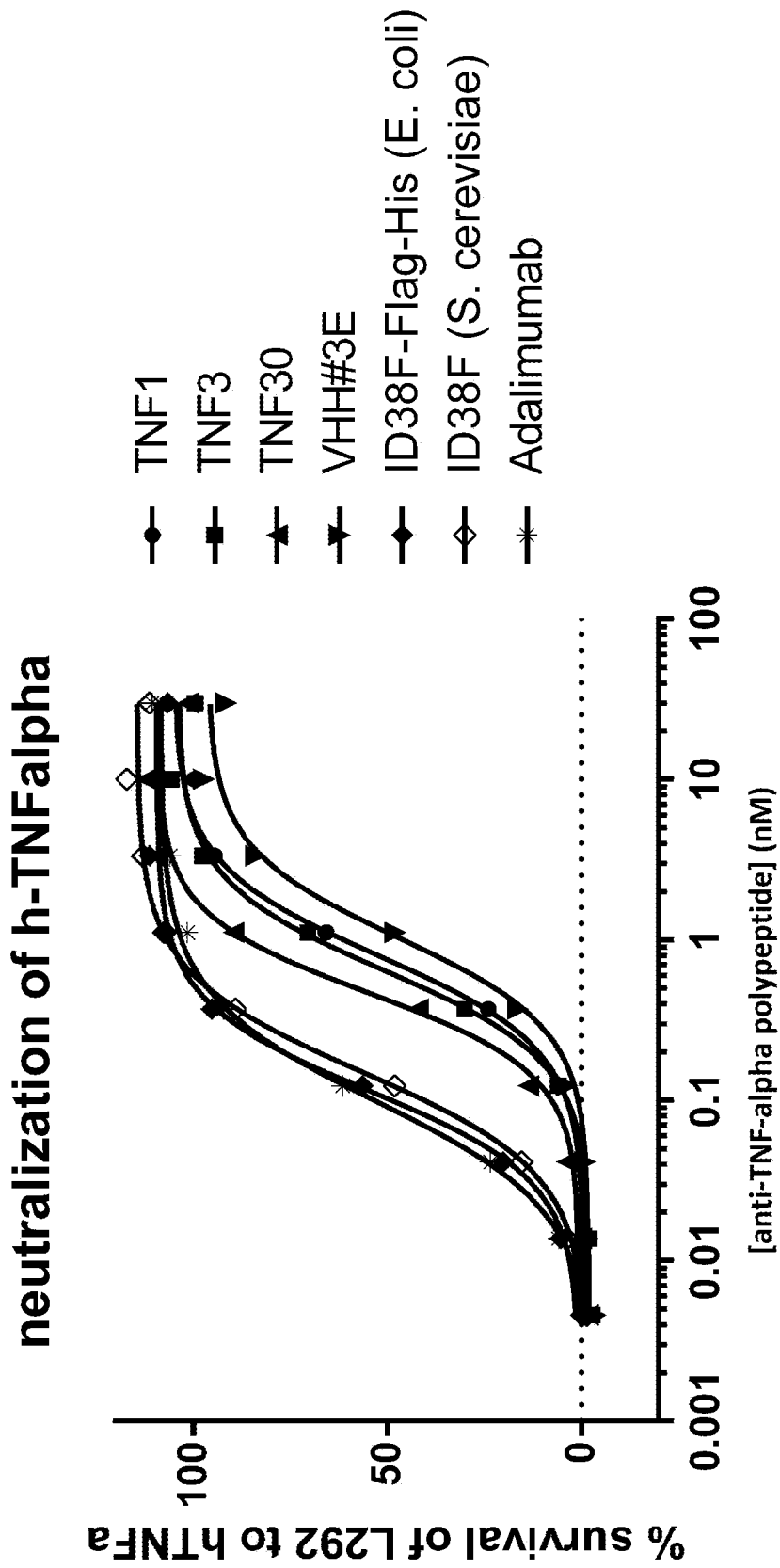
FIG. 6—Neutralisation of h-TNF-alpha by anti-TNF-alpha polypeptides of the prior art FIG. 7—Calculated luminal [anti-TNF ICVD] in cynomolgus monkey gastrointestinal tract sections FIG. 8—Total % recovery of anti-TNF ICVD from cynomolgus monkey gastrointestinal tracts FIG. 9—Humira competition ELISA OD450 data FIG. 10—anti-TNF ICVD concentration in pooled cynomolgus monkey faeces FIG. 11—Calculated anti-TNF ICVD recovered from pooled cynomolgus monkey faeces

The resultant neutralisation curves (produced with GraphPad Prism, using 4 parameter non-linear regression curve) are shown in FIG. 6. EC50 values are shown in Table 8.

TABLE 8

| Anti-TNF-alpha polypeptide | EC50 (nM) |
|---|---|
| TNF1 | 0.751 |
| TNF3 | 0.631 |
| TNF30 | 0.420 |
| VHH#3E | 1.110 |
| ID38F-Flag-His (*E. coli*-produced) | 0.102 |
| ID38F (*S. cerevisiae*-produced) | 0.127 |
| Adalimumab | 0.091 |

It can be seen from FIG. 6 and Table 8 that VHH #3E was the least potent anti-TNF-alpha polypeptide in neutralising human soluble TNF-alpha-induced cytotoxicity in L929 cells. ID38F (both *E. coli*- and *S. cerevisiae*-produced) had an approximately 4 fold-1 log lower EC50 than that of the prior art anti-TNF-alpha VHHs.

Example 11: Formulation of an Anti-TNF-Alpha ICVD of the Invention into a Pharmaceutical Composition A solid pharmaceutical composition comprising one of the anti-TNF-alpha ICVDs of the invention disclosed herein was produced in the form of mini-tablets by dry granulation and compression. This anti-TNF-alpha ICVD is a 115 amino acid, 12.6 kDa polypeptide with a pI of 6.8 and an aqueous solubility of greater than 30 mg/mL. The ICVD binds with high affinity to, and has potent neutralising activity against, human and Cynomolgus monkey TNF-alpha.

The mini-tablets were presented in different presentations, wherein each presentation contained a different quantity of mini tablets in different sizes of capsules. The main presentation used in the examples detailed below was a size 00 HPMC capsule containing 15 enterically coated mini-tablets (total 185 mg of pharmaceutically active binding polypeptide). The mini-tablet cores had a diameter of 3 mm (excluding coating thickness). The components contained in each mini-tablet and therefore in the 15 mini-tablets contained in the capsule are listed in Table 9 below.

TABLE 9

| Name of mini tablet component | Function | % w/w in composition | Quantity (mg/capsule) 185 mg dose (15 mini-tablets) | Quantity (mg) 12 mg dose (1 mini-tablet) |
|---|---|---|---|---|
| Mini-tablet cores | | | | |
| Total polypeptide | Active pharmaceutical ingredient (API) | 45.7 | 225 | 15 |

TABLE 9-continued

| Name of mini tablet component | Function | % w/w in composition | Quantity (mg/capsule) 185 mg dose (15 mini-tablets) | Quantity (mg) 12 mg dose (1 mini-tablet) |
|---|---|---|---|---|
| Mannitol | Compression aid | 12.0 | 59.25 | 3.95 |
| Microcrystalline cellulose | Compression aid | 14.6 | 72 | 4.8 |
| Croscarmellose sodium | Super disintegrant | 3.1 | 15 | 1 |
| Magnesium stearate | Lubricant | 0.8 | 3.75 | 0.25 |
| Sub coating | | | | |
| Hydroxypropylmethyl cellulose pH sensitive enteric coating | Polymer coat | 3.8 | 18.75 | 1.25 |
| Eudragit ® L100 | Enteric polymer coat | 11.7 | 57.76 | 3.85 |
| Triethyl citrate | Plasticiser | 2.3 | 11.51 | 0.77 |
| Talc | Anti-tacking agent | 5.9 | 28.93 | 1.93 |
| Sodium lauryl sulphate | Surfactant | 0.04 | 0.20 | 0.01 |

The total polypeptide in the composition has a purity of approximately 70-90% such that 225 mg of polypeptide contains 185 mg of pharmaceutically active binding polypeptide.

The mini-tablets were produced by the following methodology.

The lyophilised polypeptide was blended with mannitol and a portion of the magnesium stearate and dry slugged to increase its density. This material was then passed through a screen, blended with the other mini-tablet excipients (microcrystalline cellulose, croscarmellose sodium and the remaining magnesium stearate) and compressed to produce the mini-tablets.

The mini-tablets were then coated with a 5% solution of hydroxylpropyl methyl cellulose in ethanol:water 80:20, dried and the solvent removed to create a sub-coat and a smoother surface. The mini-tablets were then coated with Eudragit® L100 polymer, together with triethyl citrate, talc and sodium lauryl sulphate, as an organic solution in isopropyl alcohol and water and dried to create a pH-sensitive enteric coat. The resulting approximately 3 mm diameter mini-tablets were then filled into capsules at the doses given above. The pH sensitive enteric coating had a thickness of 100-170 um. The anti-TNF-alpha ICVD of the invention used in this formulation is also referred to below as "pharmaceutically active binding polypeptide", "ICVD" and "polypeptide".

Example 12: Administration to Cynomolgus Monkeys: Polypeptide Concentration in Different Intestinal Tract Compartments and in Faeces 12.1 Polypeptide Concentration in Different Intestinal Tract Compartments A study was conducted to assess the release profile of a composition similar to that of Example 11 through regions of the intestinal tract when orally administered to female Cynomolgus monkeys. The release profile was assessed by analysis of polypeptide concentration in the different intestinal tract compartments.

A single capsule containing 11 mini-tablets was administered orally to each of three Cynomolgus monkeys (the monkeys are referred to as M234, M236 and M238). The mini-tablet composition varied from that of Example 11 in that each mini-tablet contained an additional 1 mg of methylene blue (dye) and a dose of 141 mg of the ICVD. 8 of the mini-tablets also contained 0.7 mg of isoprenalin. The methylene blue dye was for visual analysis of the distribution of dissolved mini-tablets through the gastrointestinal (GI) tract (not discussed herein) and the isoprenalin was for use in a study monitoring heart rate (not discussed herein).

Four hours after oral dosing, the animals were culled. The gastrointestinal tracts were carefully removed, the different GI compartments ligated then cut and the luminal contents and washes collected. The number of undissolved and partially dissolved mini tablets were noted and these mini tablets were removed. The samples were then homogenised and frozen until analysis. After initial centrifugation of the slurries for 5 min at 5000 rpm at 10° C., 1 ml of supernatant was removed from each sample and centrifuged at 13300 rpm in a microfuge at the same temperature for 5 min. The supernatants were then centrifuged again under the same conditions, but for 20 min, after which, they were analysed using a standard Humira competition ELISA. All dilutions of samples and Humira and the ICVD standard were prepared in PBS containing 1% BSA, 0.6M NaCl, 1% human AB serum, 0.05% Tween 20 and 2× protease inhibitors. ICVD concentrations were interpolated from a standard curve using a 4 parameter, non-linear curve fitting equation in GraphPad Prism. ICVD concentrations in undiluted GI tract samples were derived by taking the means of the best interpolated data multiplied by the supernatant dilution factor.

No intact mini-tablets were found in the stomach, duodenum, jejunum or ileum of either M236 or M238. In M234, 4 intact mini-tablets were found in the stomach, 1 in the duodenum and 1 in the jejunum. No partially dissolved mini-tablets were found in any GI tract region of any monkey.

Figure 7:
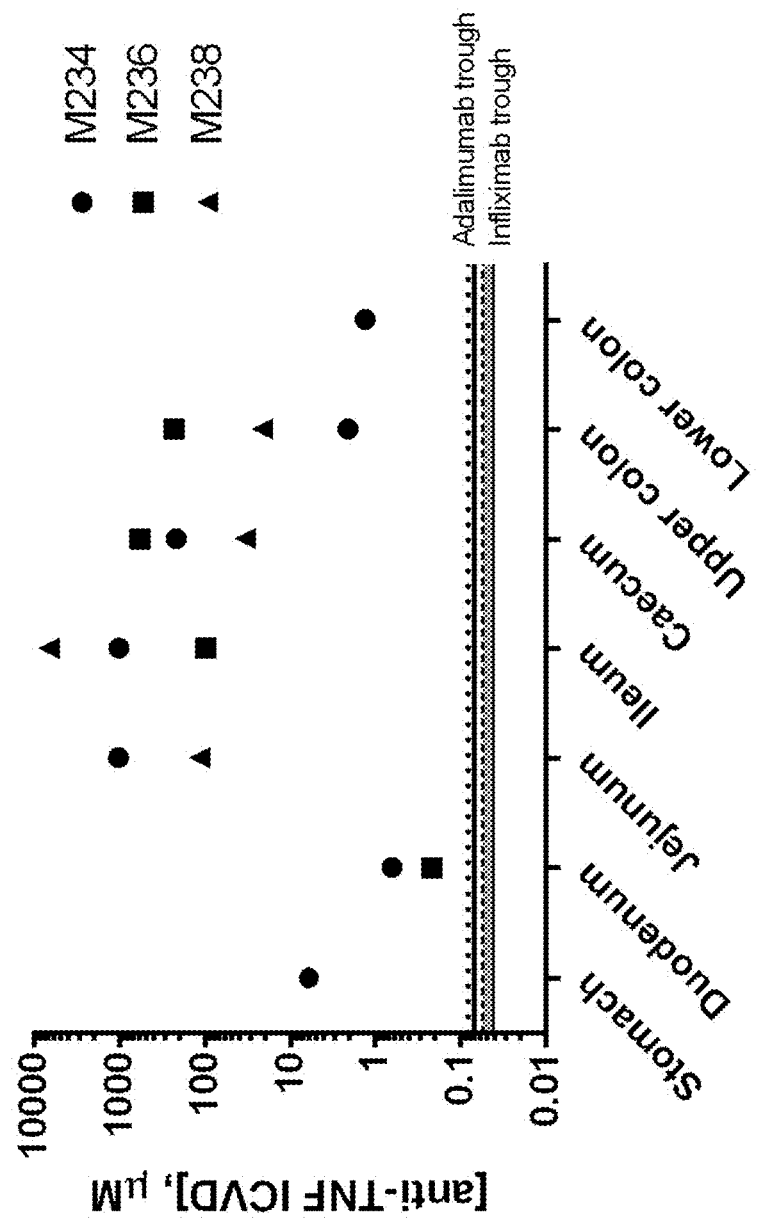

Preparation of the slurry supernatants necessitated adding large volumes of buffer, inevitably diluting the ICVD. In FIG. 7, the expected luminal concentrations of ICVD are presented. These were calculated, assuming that the luminal GI tract contents have a specific gravity of 1, by multiplying the supernatant ICVD concentrations by the fold dilution on addition of buffer. As shown, very high ICVD concentrations (0.1→1 mM) are likely to occur in the lumen of some monkey GI tract compartments.

ICVD was only detected in the contents of one Cynomolgus monkey stomach (M234). ICVD was also found at high concentrations in the contents of the ileum, caecum and upper colon of all monkeys. In addition, M234 and M238 were detected at high concentrations in the contents of the jejunum (see FIG. 7).

Figure 8:
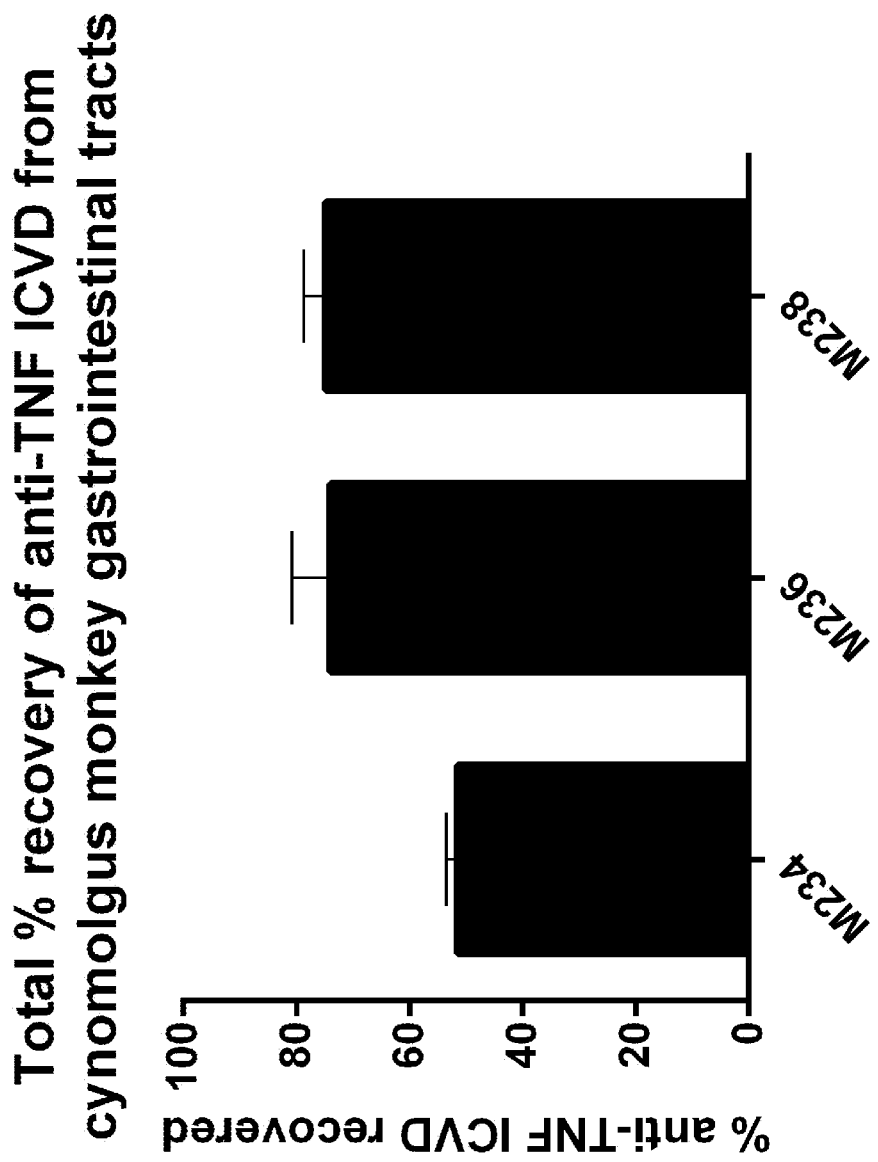

Finally, the % ICVD recovered was calculated, assuming the actual dose at 4 h was delivered by only mini-tablets that had dissolved. As shown in FIG. 8, between 51.5 and 74.9% of the ICVD dose was accounted for.

This study has shown that an anti-TNF-alpha ICVD of the invention can be delivered at high concentrations to the lower GI tract of Cynomolgus monkeys. The finding that some mini-tablets remained intact 4 h after dosing suggests that the dose will be delivered over a period of time, offering the potential of prolonged exposure. If these findings are mirrored in treatment of IBD patients when using an anti-TNF-alpha binding polypeptide, then it is reasonable to expect that the concentrations of anti-TNF-alpha polypeptide exposed to the lower GI tract will be more than adequate for effective TNF-alpha neutralisation.

12.2 Polypeptide Concentration in Faeces

A single capsule containing 11 mini-tablets was administered orally to each of three Cynomolgus monkeys. The mini-tablet composition varied from that of Example 11 in that each mini-tablet contained an additional 1 mg of methylene blue (dye) and 8 of the mini-tablets also contained 0.7 mg of isoprenalin. The methylene blue dye was for visual analysis of the dissolution of mini-tablets in faeces and the isoprenalin was for use in a study monitoring heart rate (not discussed herein).

Pooled faeces from the monkeys were collected at 8, 12, 20, 24 and 36 h (no samples were collected at 16 h). No mini-tablets were found in any of the faecal samples. These were mixed with extraction buffer (0.1% BSA, 0.6M NaCl, 0.05% Tween 20, 1× protease inhibitors, 5 mM EDTA in PBS), at 1 g faeces/4 ml buffer, then homogenised and the slurries frozen at −80° C. for storage before analysis. Visual examination revealed blue colouration of the 12 h, 20 h, 24 h and 36 h slurries. Previous in vitro experiments (not shown) have demonstrated that the increasing methylene blue concentration upon dissolution of the mini-tablets is closely correlated with ICVD concentration.

Slurries were thawed and centrifuged for 5 min at 4,000 rpm (3,200 g) to remove the bulk of particulate matter. About 1 ml of each supernatant was transferred to Eppendorf tubes and centrifuged in a microfuge at 13.5K, 10° C. for 5 min, after which supernatants were placed in new tubes and centrifuged for 20 min at 10° C. Supernatants were then used immediately for ICVD measurement using a Humira competition ELISA.

Figure 9:
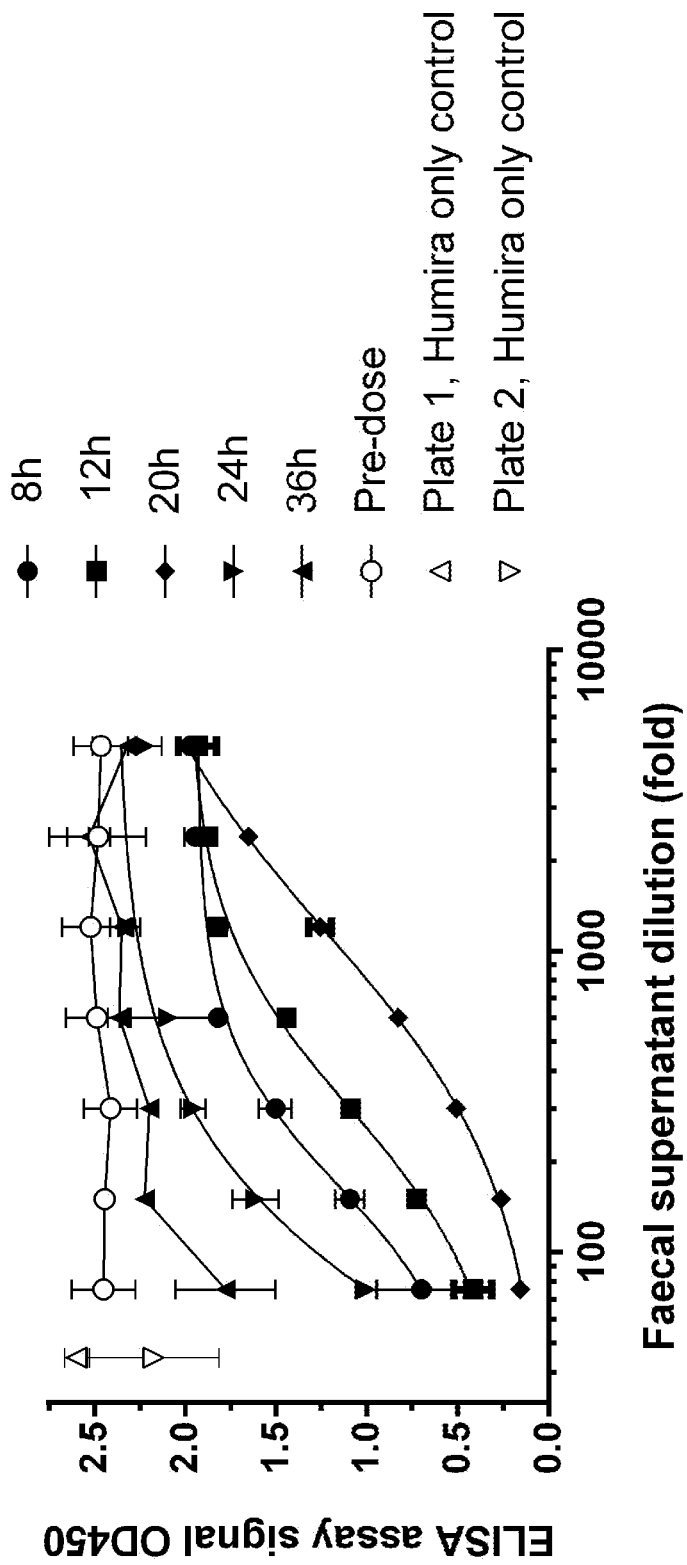

The ELISA OD450 readings for the different faecal supernatants are shown in FIG. 9. The data clearly show that ICVD is present in the faeces supernatant samples at all time points, with the possible exception of the 36 h supernatant (though there may be slight activity visible at the lowest dilution).

Figure 10:
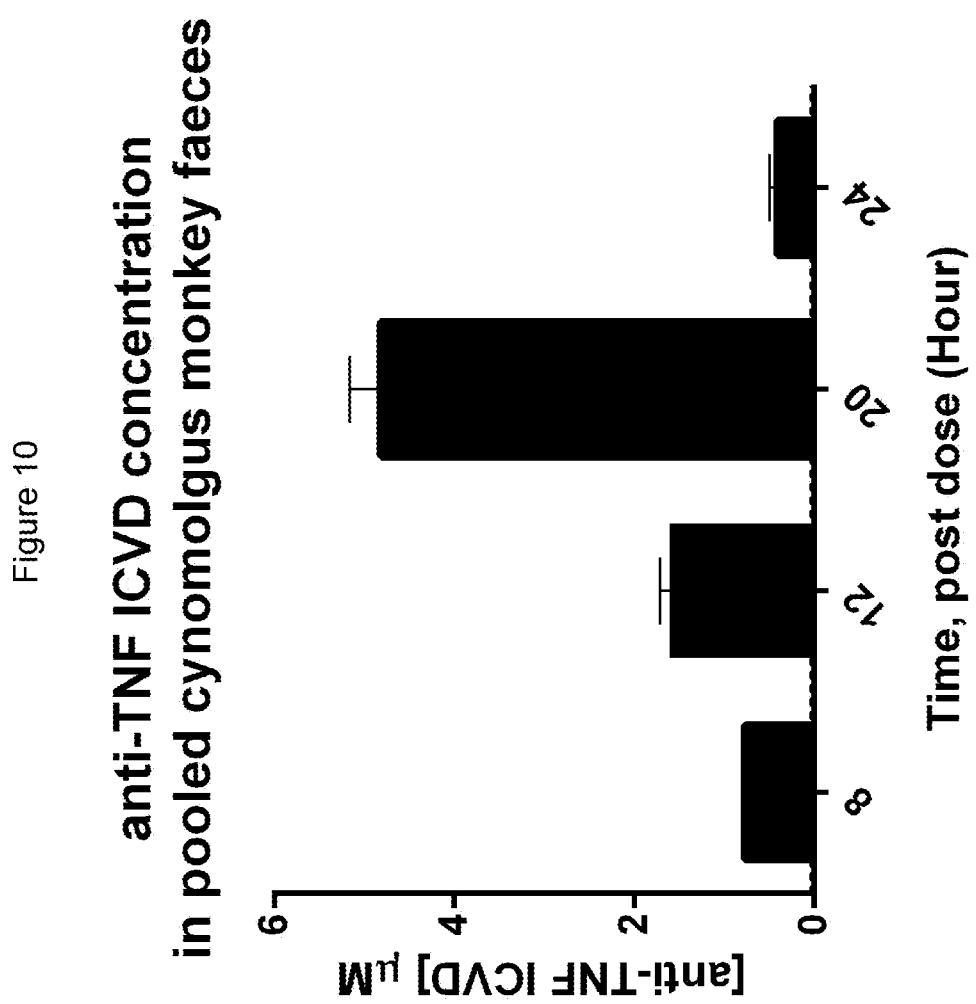

Interpolating these data against standard curves for ICVD using GraphPad Prism and multiplication by the dilution factor of buffer added gave the ICVD concentrations in each faecal sample, using the assumptions that 1 g faeces is equivalent to 1 mL liquid volume and that the polypeptide is uniformly distributed in the faeces. These are shown in FIG. 10.

Figure 11:
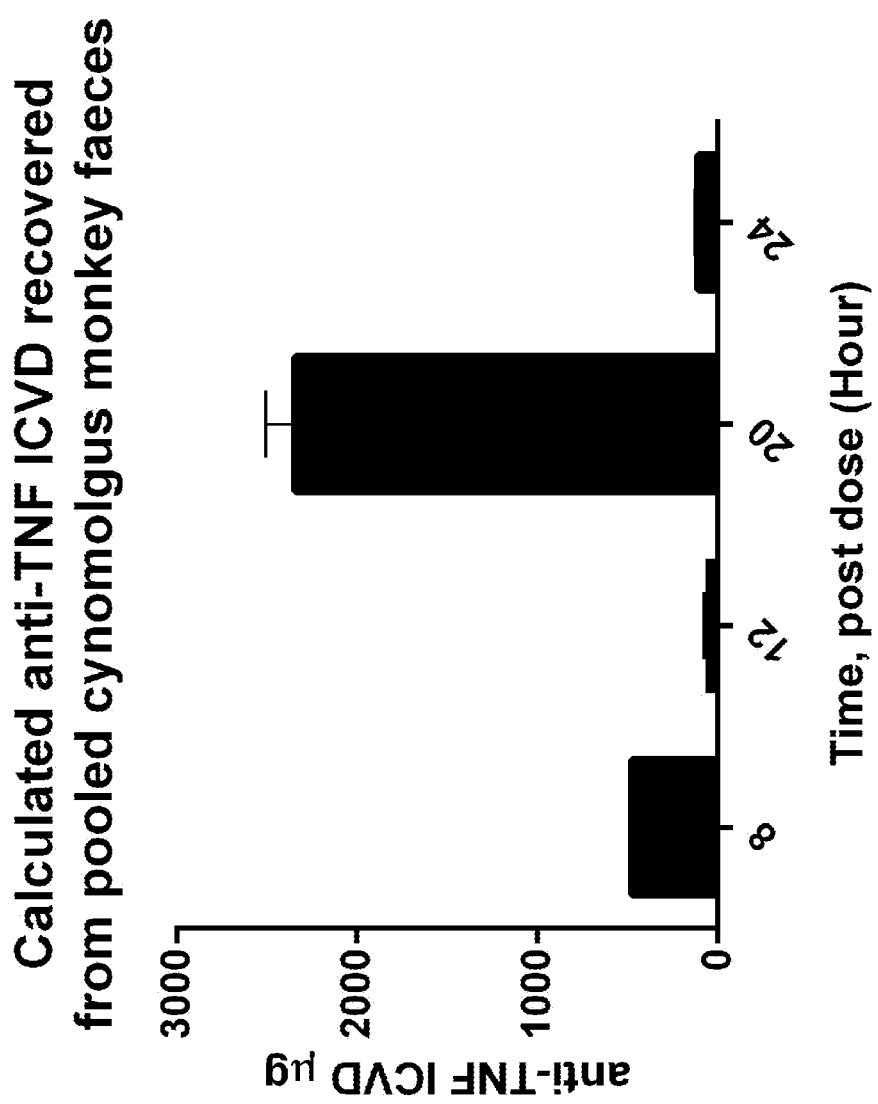

Using slurry volumes (calculated on the basis of 1 g faeces=1 ml, +volume of buffer for extraction) the pg amounts of ICVD in each sample were determined (FIG. 11)).

In summary, a sustained substantial concentration of pharmaceutically active binding polypeptide was achieved through the cynomolgus monkey intestinal tract for greater than 8 hours.

Example 13: Administration to Humans: Polypeptide Concentration at the Ileal-Caecal Junction and in Faeces 13.1 Polypeptide Concentration at the Ileal-Caecal Junction The aim of this study was to demonstrate that the anti-TNF-alpha ICVD of the invention incorporated into the composition of Example 11 is delivered at high concentrations to the ileal-caecal junction in man, a major site for Crohn's disease and the proximal site of Crohn's disease lesions in the intestine of many patients.

Four human volunteers, fitted with terminal ileostomy bags each received a single oral dose of 1665 mg ICVD, formulated into mini-tabs inside size 00 capsules (9 capsules in total). In these otherwise healthy individuals, the entire contents of the terminal ileum drains into the detachable external bag. At each hourly time point post-dosing, the fitted bag containing the total ileal effluent was removed, frozen and a new bag was fitted. Ileostomy samples were collected in this manner every hour for a period of 12 hours post dosing. Following this time, ileostomy samples were collected every four hours up to 24 hours post dosing. A Pre-dosing sample (day −1) was also taken as a control. Any partially dissolved mini-tablets observed in the bags were removed prior to analysis such that only fully soluble ICVD was analysed. The ICVD was extracted from the ileal fluid and concentrations of active ICVD were determined by functional ELISA, assuming that 1 g ileal fluid is equivalent to 1 mL liquid volume.

The data revealed high concentrations of active ICVD present in the ileostomy bags, in the range 200 nM up to 1 mM. In addition, high concentrations were observed over several hours of bag changes for each subject (see Table 10).

TABLE 10

| Subject | Hour post dose | ICVD concentration in ileal fluid (nM) |
|---|---|---|
| 31001 | 2 | 406350 |
| 31001 | 3 | 305560 |
| 31001 | 4 | 791 |
| 31002 | 2 | 32780 |
| 31002 | 3 | 1130000 |
| 31002 | 4 | 792060 |
| 31002 | 5 | 81750 |
| 31002 | 6 | 12780 |
| 31002 | 7 | 1300 |
| 31002 | 8 | 422 |
| 31002 | 9 | 1410 |
| 31002 | 10 | 7520 |
| 31002 | 11 | 10080 |
| 31002 | 12 | 9210 |
| 31002 | 16 | 6980 |
| 31003 | 3 | 1060000 |
| 31003 | 4 | 496030 |
| 31003 | 5 | 7080 |

TABLE 10-continued

| Subject | Hour post dose | ICVD concentration in ileal fluid (nM) |
|---|---|---|
| 31003 | 8 | 46110 |
| 31003 | 9 | 75480 |
| 31003 | 10 | 16030 |
| 31003 | 11 | 72940 |
| 31003 | 12 | 15870 |
| 31003 | 16 | 881 |
| 31004 | 2 | 126190 |
| 31004 | 3 | 235 |
| 31004 | 4 | 11110 |
| 31004 | 5 | 3770 |
| 31004 | 6 | 6730 |

ICVD was not detected in any of the predose (Day −1) samples from any subject.

In summary, a sustained and high concentration of pharmaceutically active binding polypeptide was achieved at the ileal-caecal junction in these human volunteers.

13.2 Polypeptide Concentration in Faeces

Healthy male subjects aged 18-45 were dosed orally with a single dose of either 62, 555, 1665 or 4995 mg of ICVD, using the composition detailed in Example 11. Each single dose per subject was administered between 8:30 to 12:00 on day 1. Faecal samples were collected pre dose (either on day −1, or prior to dosing on day 1) and at all available times post dosing up to the morning of day 4 (the end of the study). ICVD was extracted from the faeces and concentrations of active ICVD were determined by functional ELISA, assuming that 1 g faeces is equivalent to 1 mL liquid volume and that the polypeptide is uniformly distributed in the faeces.

High concentrations in the range 180 nM to 724 μM were obtained in the faeces of subjects (see Table 11).

TABLE 11

| Subject ID | mg dose ICVD | Faecal sample collection day | Pre or post dose | [ICVD] in faeces (nM) |
|---|---|---|---|---|
| 11001 | 62 | −1 | PRE DOSE | 0 |
| 11001 |  | 1 | POST DOSE | 1013 |
| 13001 | 555 | −1 | PRE DOSE | 0 |
| 13001 |  | 2 | POST DOSE | 1052 |
| 13003 | 555 | −1 | PRE DOSE | 0 |
| 13003 |  | 1 | POST DOSE | 1938 |
| 13003 |  | 2 | POST DOSE | 1511 |
| 14002 | 1665 | −1 | PRE DOSE | 0 |
| 14002 |  | 1 | POST DOSE | 5491 |
| 14002 |  | 2 | POST DOSE | 558 |
| 14004 | 1665 | −1 | PRE DOSE | 0 |
| 14004 |  | 2 | POST DOSE | 27532 |
| 14006 | 1665 | −1 | PRE DOSE | 0 |
| 14006 |  | 2 | POST DOSE | 62579 |
| 15001 | 4995 | −1 | PREDOSE | 0 |
| 15001 |  | 1 | POST DOSE | 10047 |
| 15001 |  | 2 | POST DOSE | 135285 |
| 15001 |  | 3 | POST DOSE | 330 |
| 15004 | 4995 | −1 | PREDOSE | 0 |
| 15004 |  | 3 | POST DOSE | 273 |
| 15005 | 4995 | 1 | PRE DOSE | 0 |
| 15005 |  | 1 | POST DOSE | 724684 |
| 15005 |  | 2 | POST DOSE | 258703 |
| 15005 |  | 3 | POST DOSE | 3536 |
| 15006 | 4995 | −1 | PRE DOSE | 0 |
| 15006 |  | 1 | POST DOSE | 57120 |
| 15006 |  | 2 | POST DOSE | 358 |
| 15006 |  | 2 | POST DOSE | 186 |

Anti-TNF agents that are used clinically to treat Crohn's disease, such as adalimumab (Humira) and infliximab (Remicade), are administered either by intravenous infusion or subcutaneous injection. Ungar et al. (2016) Clin Gastroenterol Hepatol. 14(4):550-557 state that trough serum levels of 56-83 nM (8-12 pg/mL) for adalimumab and 42-70 nM (6-10 pg/mL) for infliximab are required to achieve mucosal healing in 80%-90% of patients with IBD, and that this could be considered as a "therapeutic window". These trough serum levels are also indicated in FIG. 7 in respect of calculated luminal anti-TNF-alpha ICVD concentrations in cynomolgus monkey gastrointestinal tract sections established above under point 12.1.

Concentrations of anti-TNF-alpha ICVD delivered to the ileal-caecal junction (section 13.1 above) and recovered in the faeces of human volunteers during the clinical work in this section were significantly higher than these levels and are thus predicted to be efficacious as a treatment for Crohn's disease. This assumes that gut luminal concentrations of anti-TNF-alpha ICVD are comparable to serum concentrations of marketed anti-TNF agents with respect to access/penetration to the gut mucosa and sub-mucosa. However, it has been demonstrated in further experimental work (not shown) that this anti-TNF-alpha ICVD of the invention, dosed orally in DSS colitis mice, is able to penetrate to the lamina propia where it is resident for several hours, despite a lack of target (TNF) engagement in mice.

Taken together with the data presented under 13.1 above, these results demonstrate successful delivery of therapeutic levels of ICVD from the ileal-caecal junction to the anus.

Example 14: Administration to Humans: Immunogenicity Study

Protein drugs, including therapeutic antibodies, may elicit an antibody response in patients. Antibodies (of multiple Ig classes) produced in patients that recognise epitopes of protein drugs are termed anti-drug antibodies (ADAs). The presence of ADAs can result in loss of drug efficacy/potency or adverse patient effects (van Schie et al., Ann Rheum Dis 2015 74:311-314).

A study was undertaken to assess whether sustained oral dosing in man of the composition of Example 11 elicits an ADA response. Healthy male subjects aged 18-45 were dosed orally, three times daily, for 14 days with capsules containing 1665 mg (a total of 4995 mg per day) ICVD or placebo, formulated into mini-tabs according to Example 11. Serum samples from subjects were taken prior to dosing, at days 7 and 14 post-dosing, and finally at 28 days (14 days after treatment cessation). These samples were analysed by Sandwich ELISA for the presence of ICVD anti-drug antibodies (ADA). This analysis revealed ADA positive sera, albeit at low titres, from 4 volunteers, two of whom received placebo. In all of these individuals ADAs were present at some level prior to ICVD dosing (pre-existing ADAs).

Analysis of ICVD potency in a TNF-TNFR2 ELISA revealed that the presence of all ADA-positive human sera samples at 5% did not affect ICVD activity against TNF-alpha. Therefore, no evidence of ICVD neutralising ADAs was found in the sera of any volunteer at any timepoint (see Table 12).

TABLE 12

| Subject ID | Active or placebo | Sample | ADA sandwich ELISA screening | ADA Titre/serum dilution | ICVD neutralisation |
|---|---|---|---|---|---|
| 21001 | Active | Predose | Negative |  |  |
| 21001 | Active | Day 7 | Negative |  |  |

TABLE 12-continued

| Subject ID | Active or placebo | Sample | ADA sandwich ELISA screening | ADA Titre/serum dilution | ICVD neutralisation |
|---|---|---|---|---|---|
| 21001 | Active | Day 14 | Negative | | |
| 21001 | Active | Day 28 | Negative | | |
| 21002 | Active | Predose | Negative | | |
| 21002 | Active | Day 7 | Negative | | |
| 21002 | Active | Day 14 | Negative | | |
| 21002 | Active | Day 28 | Negative | | |
| 21003 | Active | Predose | Negative | | |
| 21003 | Active | Day 7 | Negative | | |
| 21003 | Active | Day 14 | Negative | | |
| 21003 | Active | Day 28 | Negative | | |
| 21004 | Placebo | Predose | Positive | 64 | No |
| 21004 | Placebo | Day 7 | Positive | 64 | No |
| 21004 | Placebo | Day 14 | Positive | 64 | No |
| 21004 | Placebo | Day 28 | Positive | 64 | No |
| 21005 | Active | Predose | Positive | 64 | No |
| 21005 | Active | Day 7 | Positive | 32 | No |
| 21005 | Active | Day 14 | Positive | 32 | No |
| 21005 | Active | Day 28 | Positive | 32 | No |
| 21006 | Active | Predose | Negative | | |
| 21006 | Active | Day 7 | Negative | | |
| 21006 | Active | Day 14 | Negative | | |
| 21006 | Active | Day 28 | Negative | | |
| 21007 | Active | Predose | Negative | | |
| 21007 | Active | Day 7 | Negative | | |
| 21007 | Active | Day 14 | Negative | | |
| 21007 | Active | Day 28 | Negative | | |
| 21008 | Active | Predose | Positive | 4 | No |
| 21008 | Active | Day 7 | Positive | 4 | No |
| 21008 | Active | Day 14 | Positive | 8 | No |
| 21008 | Active | Day 28 | Positive | 128 | No |
| 21009 | Placebo | Predose | Positive | 8 | No |
| 21009 | Placebo | Day 7 | Positive | 8 | No |
| 21009 | Placebo | Day 14 | Positive | 16 | No |
| 21009 | Placebo | Day 28 | Positive | 8 | No |
| 21010 | Active | Predose | Negative | | |
| 21010 | Active | Day 7 | Negative | | |
| 21010 | Active | Day 14 | Negative | | |
| 21010 | Active | Day 28 | Negative | | |

Clauses

A set of clauses defining the invention and its preferred aspects is as follows:

1. A polypeptide comprising an immunoglobulin chain variable domain which binds to TNF-alpha, wherein the immunoglobulin chain variable domain comprises three complementarity determining regions (CDR1-CDR3) and four framework regions (FR1-FR4), wherein CDR1 comprises a sequence sharing 60% or greater sequence identity with SEQ ID NO: 1, CDR2 comprises a sequence sharing 50% or greater sequence identity with SEQ ID NO: 2 and
   (a) CDR3 comprises a sequence sharing 80% or greater sequence identity with SEQ ID NO: 3 or
   (b) CDR3 comprises a sequence sharing 50% or greater sequence identity with SEQ ID NO: 3 and wherein the residue of CDR3 corresponding to residue number 3 of SEQ ID NO: 3 is R, D, N, C, E, Q, G, H, I, L, K, M, F, P, S, T, W, Y or V.
2. The polypeptide according to clause 1, wherein the residue of CDR3 corresponding to residue number 3 of SEQ ID NO: 3 is R, H, D, E, N, Q, S, T, Y, G, V, L, W, P, M, C, F or I.
3. The polypeptide according to clause 2, wherein the residue of CDR3 corresponding to residue number 3 of SEQ ID NO: 3 is H.
4. The polypeptide according to clause 3, wherein CDR3 comprises SEQ ID NO: 3.
5. The polypeptide according to clause 1, wherein the sequence of CDR3 is SEQ ID NO: 3, SEQ ID NO: 70, SEQ ID NO: 71 or SEQ ID NO: 72.
6. The polypeptide according to any one of clauses 1 to 5, wherein CDR1 comprises a sequence sharing 80% or greater sequence identity with SEQ ID NO: 1.
7. The polypeptide according to clause 6, wherein CDR1 comprises SEQ ID NO: 1.
8. The polypeptide according to clause 6, wherein the sequence of CDR1 is SEQ ID NO: 1, SEQ ID NO: 59 or SEQ ID NO: 60.
9. The polypeptide according to any one of clauses 1 to 8, wherein CDR2 comprises a sequence sharing 55% or greater sequence identity, such as sharing 60% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, with SEQ ID NO: 2.
10. The polypeptide according to clause 9, wherein CDR2 comprises SEQ ID NO: 2.
11. The polypeptide according to clause 9 wherein the sequence of CDR2 is SEQ ID NO: 61, SEQ ID NO: 62, SEQ ID NO: 2, SEQ ID NO: 63, SEQ ID NO: 64, SEQ ID NO: 65, SEQ ID NO: 66, SEQ ID NO: 67, SEQ ID NO: 68, SEQ ID NO: 69.
12. The polypeptide according to any one of clauses 1 to 11 which comprises a sequence sharing 50% or greater sequence identity, such as sharing 55% or greater sequence identity, such as sharing 60% or greater sequence identity, such as sharing 65% or greater sequence identity, such as sharing 70% or greater sequence identity, such as sharing 75% or greater sequence identity, such as sharing 80% or greater sequence identity, such as sharing 85% or greater sequence identity, such as sharing 90% or greater sequence identity, such as sharing 95% or greater sequence identity, such as sharing 96% or greater sequence identity, such as sharing 97% or greater sequence identity, such as sharing 98% or greater sequence identity, such as sharing 99% or greater sequence identity, with SEQ ID NO: 8.
13. The polypeptide according to clause 12 which comprises SEQ ID NO: 8.
14. The polypeptide according to any one of clauses 1 to 13, which is selected from the list consisting of: a VHH, a VH, a VL, a V-NAR, a Fab fragment and a F(ab')2 fragment.
15. A polynucleotide encoding the polypeptide according to any one of clauses 1 to 14, especially wherein the polynucleotide comprises or consists of a sequence sharing 70% or greater, such as 80% or greater, such as 90% or greater, such as 95% or greater, such as 99% or greater sequence identity with any one of SEQ ID NOs: 83 to 88, or more especially wherein the polynucleotide comprises or consists of any one of SEQ ID NOs: 83 to 88.

Miscellaneous

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

| Name (SEQ ID NO) | FR1 | CDR1 | FR2 | CDR2 | FR3 | CDR3 | FR4 |
|---|---|---|---|---|---|---|---|
| | | | | SEQUENCES | | | |
| | | | | Family 1 sequences | | | |
| Q65F2 (23) | EVQLVESGGGLVQPGGSLRLSCAASGFDFS | SHWMY | WVRQAPGKGLEWVS | EINTNGLITSVDSVKG | RFTVSRDNAANTLYLEMTSLEPEDTALYYCAR | NQKGLN | KGQGTQVTVSS |
| Q65F3 (24) | EVQLVESGGGLVQPGGSLRLSCAASGFDFS | SHWMY | WVRQAPGKGLEWVS | EINTNGLITKYIDSVRG | RFTASRDNAANTLYLEMTNLEPEDTALYYCAR | NQKGLN | KGQGTQVTVSS |
| Q62F2 (25) | QVQLVESGGGLVQPGGSLRLSCAASGFDFN | SHWMY | WVRQAPGKGLEWVS | EINTNGLITNVVDSVKG | RFTVSRDNAANTLYLEMTSLKPEDTALYYCAR | NQKGLN | KGQGTQVTVSS |
| Q65G1 (26) | EVQLVESGGGLVQPGGSLRLSCVASGFDFY | SHWMY | WVRQAPGKGLEWVS | EINTNGLITKYIDSVRG | RFTVSRDNAANTLYLEMTNLEPEDTALYYCAR | NQKGLN | KGQGTQVTVSS |
| Q65H6 (27) | EVQLVESGGGLVQPGGSLRLSCVASGFDFY | SHWMY | WVRQAPGKGLEWVS | EINTNGLITKYIDSVRG | RFTVSRDNAANTLYLEMTNLEPEDTALYYCAR | NQKGLN | KGQGTQVTVSS |
| Q65F1 (28) | EVQLVESGGGLVQPGGSLRLSCAASGFDFG | VHWMY | WVRQAPGKGLEWVS | EINTNGLITKYIDSVGG | RFTVSRDNAANRLYLEMTNLEPEDTALYYCAR | NQMGLN | KGQGTQVTVSS |
| Q65D1 (29) | EVQLVESGGGLVQPGGSLRLSCTASGFDFD | NHWMC | WVRQAPGKGLEWVS | EINTNGLITKYADFVKG | RFTVSRDNAANTLYLQIIRLKPEDTALYYCAR | NQKGLN | KGQGTQVTVSS |
| Q65C7 (30) | EVQLVESGGGLVQPGRSLRLSCVASGFDFS | SHWMY | WVRQAPGKGLEWVS | EINTNGLITKYADFVKG | RFTVSRDNAANTLYLEIITRLEPEDTALYYCAR | NQKGLN | KGQGTQVTVSS |
| Q65D3 (31) | EVQLVESGGGLVQPGGSLRLSCVASGFDFS | SHWMY | WVRQAPGKGLEWVS | EINTNGLITKYADSTKG | RFTVSRDNAANMLNLEMTSLEPEDTALYYCAR | NERGLN | KGQGTQVTVSS |
| Q65B1 (32) | EVQLVESGGGLVQPGGSLRKLSCAASGFDFS | SHWMY | WVRQAPGKELEWLS | EINTNGLITKYGDSVKG | RFTVSANNAANKMYLELTRLEPEDTALYYCAR | NQKGLN | KGQGTQVTVSS |
| | | | | Family 2 sequences | | | |
| Q65F6 (33) | EVQLVESGGGLVQPGGSLRLSCTASGFDFG | IHWMY | WVRQAPGKELEWVA | EINTNGLITLYSDSVRG | RFTASRDNANNALFLQMNDLKFEDTAVYYCAK | SRNGAA | KGQGTQVTVSS |
| Q65F11 (34) | EVQLVESGGGLVQPGGSLRLSCTASGFDFG | IHNMY | WVRQAPGKELEWVA | EINTNGLITLYADSVKG | RFTASRDNAKNALFLQMNDLKFEDTAVYYCAK | ARNGAA | KGQGTQVTVSS |
| Q65E12 (35) | EVQLVESGGGLVQPGGSLRLSCSCASGFDFS | IHWMY | WVRQAPGKELEWVA | EINTNGLITLYADSVKG | RFTASRDNAKNALFLQMNDLKFEDTAVYYCAK | SRNGAA | GGQGTQVTVSS |
| Q65C12 (36) | EVQLVESGGGLVQPGGSLRLSCTASGFPFD | IHNMY | WVRQAPGKELEWVA | EINTNALITTYADSVKG | RFTISRDNAKNTLFLQMNDLKFEDTAVYYCTH | SRNGAA | KGQGTQVTVSS |

| Name (SEQ ID NO) | FR1 | CDR1 | FR2 | CDR2 | FR3 | CDR3 | FR4 |
|---|---|---|---|---|---|---|---|
| Q65A6 (37) | EVQLVESGGGLVQPGGSLRLSCTASGLDFG | IHNMY | WVRQAPGKELEWVA | EINTNGLITHYTDSVSG | RFTISRDNAKNTLFLQMNDLKPEDTAVYACAT | SRNGAA | KGQGTQVTVSS |
| Q65A3 (38) | EVQLVESGGGLVQPGGSLRPSCTTSGLDFG | IHNMY | WFRQAPGKELEWVA | EINTNALITKYADSVKG | RFTISRDNAKNTLFLQMNDLKSEDTAVYYCSN | TQNGAA | KGQGVQVTVSS |
| Q62E10 (22) | QVQLVESGGGLVQPGGSLRLSCTTSGLDFG | IHWMY | WFRQAPGKELEWVA | EINTNALITKYADSVKG | RFTISRDNAKNTLFLQMNDLKSEDTAVYYCSN | TQNGAA | KGQGVQVTVSS |
| Q62F10 (39) | EVQLVESGGGLVQPGGSLRLSCVASGFDFN | IHWMY | WVRQAPGKELEWVA | EINTNGLITVYPDSVKG | RFTISRDNAKNTLFLQMNNLKPEDTAVYYCTN | TQNGKT | KGQGTQVTVSS |

Q65B1-based constructs and mutants

| Name (SEQ ID NO) | FR1 | CDR1 | FR2 | CDR2 | FR3 | CDR3 | FR4 |
|---|---|---|---|---|---|---|---|
| ID7F-EV (41) | EVQLVESGGGLVQPGASLKLSCAASGFDFS | SHWMY | WVRQAPGKELEWLS | EINTNGLITKYGDSVKG | RFTVSANNAANKMYLELTRLEPEDTALYYCAR | NQKGLN | KGQGTQVTVSS |
| ID9F-EV (43) | EVQLVESGGGLVQPGGSLKLSCAASGFDFS | SHWMY | WVRQAPGKELEWLS | EINTNGLITKYGDSVKG | RFTVSANNAANKMYLELTRLEPEDTALYYCAR | NQKGLN | KGQGTQVTVSS |
| ID13F-EV (44) | EVQLVESGGGLVQPGGSLKLSCAASGFDFS | SHWMY | WVRQAPGKELEWLS | EINTNGLITKYGDSVHG | RFTVSANNAANKMYLELTRLEPEDTALYYCAR | NQHGLN | KGQGTQVTVSS |
| ID14F-EV (45) | EVQLVESGGGLVQPGGSLKLSGAASGFDFS | SHWMY | WVRQAPGKELEWLS | EINTNGLITKYGDSVKG | RFTVSANNAANKMYLELTRLEPEDTALYYCAR | NQKGLN | KGQGTQVTVSS |
| ID15F-EV (46) | EVQLVESGGGLVQPGGSLKLSCAASGFDFS | SHWMY | WVRQAPGKELEWLS | EINTNGLITKYGDSVKG | RFTVSANNAANKMYLELTRLEPEDTALYYCAR | NQHGLN | HGQGTQVTVSS |
| ID22F (47) | EVQLVESGGGLVQPGGSLKLSCAASGFDFS GGGSGGGSGGGSGGGSGGGSGGGSGGGS EVQLVESGGGLVQPGGSLKLSCAASGFDFS | SHWMY | WVRQAPGKELEWLS | EINTNGLITKYGDSVKG | RFTVSANNAANKMYLELTRLEPEDTALYYCAR | NQHGLN | HGQGTQVTVSS |
| ID23F (48) | EVQLVESGGGLVQPGGSLKLSCAASGFDFS GGGSGGGSGGGSGGGSGGGSGGGSGGGS EVQLVESGGGLVQPGGSLKLSCAASGFDFS | SHWMY | WVRQAPGKELEWLS | EINTNGLITKYGDSVKG | RFTVSANNAANKMYLELTRLEPEDTALYYCAR | NQKGLN | KGQGTQVTVSS |
| ID24F (49) | EVQLVESGGGLVQPGGSLKLSCAASGFDFS GGGSGGGSGGGSGGGSGGGSGGGSGGGS EVQLVESGGGLVQPGGSLKLSCAASGFDFS | SHWMY | WVRQAPGKELEWLS | EINTNGLITHYGDSVKG | RFTVSRNNAANSMYLELTRLEPEDTALYYCAR | NQKGLN | KGQGTQVTVSS |
| ID25F (50) | EVQLVESGGGLVQPGGSLKLSCAASGFDFS GGGSGGGSGGGSGGGSGGGSGGGSGGGS EVQLVESGGGLVQPGGSLKLSCAASGFDFS | SHWMY | WVRQAPGKELEWLS | EINTNGLITHYGDSVKG | RFTVSRNNAANKMYLELTRLEPEDTALYYCAR | NQHGLN | KGQGTQVTVSS |

| Name (SEQ ID NO) | FR1 | CDR1 | FR2 | CDR2 | FR3 | CDR3 | FR4 |
|---|---|---|---|---|---|---|---|
| ID26F (51) | EVQLVESGGGLVQPGGSLKLSCAASGFDFS GGGSGGGGSGGGGSGGGGSGGGGSGGGGS EVQLVESGGGLVQPGGSLKLSCAASGFDFS | SHWMY | WVRQAPGKELEWLS | EINTNGLITHYGDSVKG | RFTVSRNNAANSMYLELTRLEPEDTALYYCAR | NQHGLN | KGQGTQVTVSS |
| ID27F (52) | EVQLVESGGGLVQPGGSLKLSCAASGFDFS GGGSGGGGSGGGGSGGGGSGGGGSGGGGS EVQLVESGGGLVQPGGSLKLSCAASGFDFS | SHWMY | WVRQAPGKELEWLS | EINTNGLITHYGDSVKG | RFTVSRNNAANKMYLELTRLEPEDTALYYCAR | NQKGLN | KGQGTLVTVSS |
| ID28F (53) | EVQLVESGGGLVQPGGSLKLSCAASGFDFS GGGSGGGGSGGGGSGGGGSGGGGSGGGGS EVQLVESGGGLVQPGGSLKLSCAASGFDFS | SHWMY | WVRQAPGKELEWLS | EINTNGLITHYGDSVHG | RFTVSRNNAANKMYLELTRLEPEDTALYYCAR | NQKGLN | KGQGTQVTVSS |
| ID29F (54) | EVQLVESGGGLVQPGGSLKLSCAASGFDFS GGGSGGGGSGGGGSGGGGSGGGGSGGGGS EVQLVESGGGLVQPGGSLKLSCAASGFDFS | SHWMY | WVRQAPGKELEWLS | EINTNGLITKYGDSVHG | RFTVSRNNAANKMYLELTRLEPEDTALYYCAR | NQHGLN | KGQGTQVTVSS |
| ID8F-EV (42) | EVQLVESGGGLVQPGGSLKLSCAASGFDFS | SHWMY | WVRQAPGKELEWLS | EINTNGLITKYGDSVKG | RFTVSRNNAANKMYLELTRLEPEDTALYYCAR | NQKGLN | KGQGTQVTVSS |
| ID34F (56) | EVQLVESGGGLVQPGGSLKLSCAASGFDFS | SHWMY | WVRQAPGKELEWLS | EINTNGLITHYGDSVKG | RFTVSRNNAANKMYLELTRLEPEDTALYYCAR | NQHGLN | KGQGTQVTVSS |
| ID37F (57) | DVQLVESGGGLVQPGGSLKLSCAASGFDFS | SHWMY | WVRQAPGKELEWLS | EINTNGLITHYGDSVKG | RFTVSRNNAANKMYLELTRLEPEDTALYYCAR | NQKGLN | KGQGTQVTVSS |
| ID38F (8) | DVQLVESGGGLVQPGGSLKLSCAASGFDFS | SHWMY | WVRQAPGKELEWLS | EINTNGLITHYGDSVKG | RFTVSRNNAANKMYLELTRLEPEDTALYYCAR | NQHGLN | KGQGTQVTVSS |
| Comparative examples |
| Q62F11 (40) | QVQLVESGGGLVQPGGSLRLSCAASGFSFS | DYVMG | WFRQAPGKEREFVG | FIRWDGLVTRYADAVKG | RFTISRDNARNTLSLQTIGLLAEDTAVYYCAA | SGGGSGPVNAGSYEY | WGQGTQVTVSS |

The invention claimed is:

1. A VH or VHH which binds to TNF-alpha and comprises a set of three complementarity determining regions (CDRs) comprising CDR1, CDR2 and CDR3, wherein the respective SEQ ID Nos of CDR1, CDR2 and CDR3 of said set are selected from the group consisting of:
   (a) SEQ ID NO: 1, SEQ ID NO: 2 and SEQ ID NO: 3,
   (b) SEQ ID NO: 1, SEQ ID NO: 63 and SEQ ID NO: 70,
   (c) SEQ ID NO: 1, SEQ ID NO: 64 and SEQ ID NO: 70,
   (d) SEQ ID NO: 1, SEQ ID NO: 65 and SEQ ID NO: 70,
   (e) SEQ ID NO: 59, SEQ ID NO: 66 and SEQ ID NO: 71,
   (f) SEQ ID NO: 60, SEQ ID NO: 67, and SEQ ID NO: 70,
   (g) SEQ ID NO: 1, SEQ ID NO: 67 and SEQ ID NO: 70,
   (h) SEQ ID NO: 1, SEQ ID NO: 68 and SEQ ID NO: 72,
   (i) SEQ ID NO: 1, SEQ ID NO: 69 and SEQ ID NO: 70,
   (j) SEQ ID NO: 1, SEQ ID NO: 62 and SEQ ID NO: 70,
   (k) SEQ ID NO: 1, SEQ ID NO: 69 and SEQ ID NO: 3,
   (l) SEQ ID NO: 1, SEQ ID NO: 2 and SEQ ID NO: 70,
   (m) SEQ ID NO: 1, SEQ ID NO: 61 and SEQ ID NO: 70 and
   (n) SEQ ID NO: 1, SEQ ID NO: 62 and SEQ ID NO: 3.

2. The VH or VHH of claim 1 which comprises SEQ ID NO: 8.

3. The VH or VHH of claim 1 wherein the CDR1 comprises the sequence of SEQ ID NO: 1, the CDR2 comprises the sequence of SEQ ID NO: 2 and the CDR3 comprises the sequence of SEQ ID NO: 3.

4. A pharmaceutical composition comprising the VH or VHH of claim 1 and one or more pharmaceutically acceptable diluents or carriers.

5. The pharmaceutical composition of claim 4, wherein the composition is presented in enterically coated form.

6. A method of treating autoimmune and/or inflammatory disease comprising administering to a person in need thereof a therapeutically effective amount of the VH or VHH of claim 1.

7. The method of treating autoimmune and/or inflammatory disease of claim 6 wherein the autoimmune and/or inflammatory disease is selected from the list consisting of Crohn's disease, ulcerative colitis, irritable bowel syndrome, diabetes type II, glomerulonephritis, autoimmune hepatitis, Sjogren's syndrome, celiac disease, drug- or radiation-induced mucositis, pemphigus, psoriasis, eczema and scleroderma.

8. The method of treating autoimmune disease of claim 6, wherein the VH or VHH is administered orally.

* * * * *

UNITED STATES PATENT AND TRADEMARK OFFICE
CERTIFICATE OF CORRECTION

PATENT NO. : 10,633,438 B2  
APPLICATION NO. : 15/273353  
DATED : April 28, 2020  
INVENTOR(S) : Scott Crowe et al.

Page 1 of 1

It is certified that error appears in the above-identified patent and that said Letters Patent is hereby corrected as shown below:

On the Title Page

Item (73) Assignee should read: VHsquared Limited, Cambridge (GB)

Signed and Sealed this  
Eighth Day of December, 2020

Andrei Iancu  
*Director of the United States Patent and Trademark Office*

SEQUENCE LISTING

<160> NUMBER OF SEQ ID NOS: 88

<210> SEQ ID NO 1
<211> LENGTH: 5
<212> TYPE: PRT
<213> ORGANISM: Artificial Sequence
<220> FEATURE:
<223> OTHER INFORMATION: ID38F CDR1

<400> SEQUENCE: 1

Ser His Trp Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: ID38F CDR2

<400> SEQUENCE: 2

Glu Ile Asn Thr Asn Gly Leu Ile Thr His Tyr Gly Asp Ser Val Lys
1               5                   10                  15

Gly

<210> SEQ ID NO 3
<211> LENGTH: 6
<212> TYPE: PRT
<213> ORGANISM: Artificial Sequence
<220> FEATURE:
<223> OTHER INFORMATION: ID38F CDR3

<400> SEQUENCE: 3

Asn Gln His Gly Leu Asn
1               5

<210> SEQ ID NO 4
<211> LENGTH: 30
<212> TYPE: PRT
<213> ORGANISM: Artificial Sequence
<220> FEATURE:
<223> OTHER INFORMATION: ID38F FR1

<400> SEQUENCE: 4

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: ID38F FR2

<400> SEQUENCE: 5

Trp Val Arg Gln Ala Pro Gly Lys Glu Leu Glu Trp Leu Ser
1               5                   10

<210> SEQ ID NO 6
<211> LENGTH: 32
<212> TYPE: PRT
<213> ORGANISM: Artificial Sequence
<220> FEATURE:
<223> OTHER INFORMATION: ID38F FR3

<400> SEQUENCE: 6

Arg Phe Thr Val Ser Arg Asn Asn Ala Ala Asn Lys Met Tyr Leu Glu
1               5                   10                  15

Leu Thr Arg Leu Glu Pro Glu Asp Thr Ala Leu Tyr Tyr Cys Ala Arg
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: ID38F FR4

<400> SEQUENCE: 7

Lys Gly Gln Gly Thr Gln Val Thr Val Ser Ser
1               5                   10

<210> SEQ ID NO 8
<211> LENGTH: 115
<212> TYPE: PRT
<213> ORGANISM: Artificial Sequence
<220> FEATURE:
<223> OTHER INFORMATION: ID38F

<400> SEQUENCE: 8

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser
        115

<210> SEQ ID NO 9
<211> LENGTH: 157
<212> TYPE: PRT
<213> ORGANISM: Homo sapiens
<220> FEATURE:
<223> OTHER INFORMATION: Soluble human TNF-alpha

<400> SEQUENCE: 9

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile

```
                65                  70                  75                  80
Ser Arg Ile Ala Val Ser Tyr Gln Thr Lys Val Asn Leu Leu Ser Ala
                    85                  90                  95

Ile Lys Ser Pro Cys Gln Arg Glu Thr Pro Glu Gly Ala Glu Ala Lys
                100                 105                 110

Pro Trp Tyr Glu Pro Ile Tyr Leu Gly Gly Val Phe Gln Leu Glu Lys
                115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 10
<211> LENGTH: 233
<212> TYPE: PRT
<213> ORGANISM: Homo sapiens
<220> FEATURE:
<223> OTHER INFORMATION: Membrane-bound human TNF-alpha

<400> SEQUENCE: 10

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 11
<211> LENGTH: 157
<212> TYPE: PRT
<213> ORGANISM: Macaca fascicularis
<220> FEATURE:
<223> OTHER INFORMATION: Soluble cynomolgus monkey TNF-alpha
```

<400> SEQUENCE: 11

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Val Ala Asn Gly Val Glu Leu Thr Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Asn His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Leu Pro Asp Tyr Leu Asp Phe
    130                 135                 140

Ala Glu Ser Gly Gln Val Tyr Phe Gly Ile Ile Ala Leu
145                 150                 155

<210> SEQ ID NO 12
<211> LENGTH: 233
<212> TYPE: PRT
<213> ORGANISM: Macaca fascicularis
<220> FEATURE:
<223> OTHER INFORMATION: Membrane-bound cynomolgus monkey TNF-alpha

<400> SEQUENCE: 12

Met Ser Thr Glu Ser Met Ile Gln Asp Val Glu Leu Ala Glu Glu Ala
1               5                   10                  15

Leu Pro Arg Lys Thr Ala Gly Pro Gln Gly Ser Arg Arg Cys Trp Phe
            20                  25                  30

Leu Ser Leu Phe Ser Phe Leu Leu Val Ala Gly Ala Thr Leu Phe
        35                  40                  45

Cys Leu Leu His Phe Gly Val Ile Gly Pro Gln Arg Glu Glu Phe Pro
    50                  55                  60

Lys Asp Pro Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Val Ala Asn Gly Val Glu Leu Thr Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Asn His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Leu Pro Asp Tyr Leu Asp Phe Ala Glu Ser Gly
    210                 215                 220

Gln Val Tyr Phe Gly Ile Ile Ala Leu
225                 230

<210> SEQ ID NO 13
<211> LENGTH: 156
<212> TYPE: PRT
<213> ORGANISM: Mus musculus
<220> FEATURE:
<223> OTHER INFORMATION: Soluble mouse TNF-alpha

<400> SEQUENCE: 13

Leu Arg Ser Ser Gln Asn Ser Ser Asp Lys Pro Val Ala His Val Val
1               5                   10                  15

Val Ala Asn His Gln Val Glu Glu Gln Leu Glu Trp Leu Ser Gln Arg
            20                  25                  30

Ala Asn Ala Leu Leu Ala Asn Gly Met Asp Leu Lys Asp Asn Gln Leu
        35                  40                  45

Val Val Pro Ala Asp Gly Leu Tyr Leu Val Tyr Ser Gln Val Leu Phe
    50                  55                  60

Lys Gly Gln Gly Cys Pro Asp Tyr Val Leu Leu Thr His Thr Val Ser
65                  70                  75                  80

Arg Phe Ala Ile Ser Tyr Gln Glu Lys Val Asn Leu Leu Ser Ala Val
                85                  90                  95

Lys Ser Pro Cys Pro Lys Asp Thr Pro Glu Gly Ala Glu Leu Lys Pro
            100                 105                 110

Trp Tyr Glu Pro Ile Tyr Leu Gly Gly Val Phe Gln Leu Glu Lys Gly
        115                 120                 125

Asp Gln Leu Ser Ala Glu Val Asn Leu Pro Lys Tyr Leu Asp Phe Ala
    130                 135                 140

Glu Ser Gly Gln Val Tyr Phe Gly Val Ile Ala Leu
145                 150                 155

<210> SEQ ID NO 14
<211> LENGTH: 235
<212> TYPE: PRT
<213> ORGANISM: Mus musculus
<220> FEATURE:
<223> OTHER INFORMATION: Membrane-bound mouse TNF-alpha

<400> SEQUENCE: 14

Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Gln Arg Asp Glu Lys Phe
    50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
            100                 105                 110

-continued

Asn Ala Leu Leu Ala Asn Gly Met Asp Leu Lys Asp Asn Gln Leu Val
            115                 120                 125

Val Pro Ala Asp Gly Leu Tyr Leu Val Tyr Ser Gln Val Leu Phe Lys
        130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
    210                 215                 220

Ser Gly Gln Val Tyr Phe Gly Val Ile Ala Leu
225                 230                 235

<210> SEQ ID NO 15
<211> LENGTH: 5
<212> TYPE: PRT
<213> ORGANISM: Artificial Sequence
<220> FEATURE:
<223> OTHER INFORMATION: Q62E10 CDR1

<400> SEQUENCE: 15

Ile His Trp Met Tyr
1               5

<210> SEQ ID NO 16
<211> LENGTH: 17
<212> TYPE: PRT
<213> ORGANISM: Artificial Sequence
<220> FEATURE:
<223> OTHER INFORMATION: Q62E10 CDR2

<400> SEQUENCE: 16

Glu Ile Asn Thr Asn Ala Leu Ile Thr Lys Tyr Ala Asp Ser Val Lys
1               5                   10                  15

Gly

<210> SEQ ID NO 17
<211> LENGTH: 6
<212> TYPE: PRT
<213> ORGANISM: Artificial Sequence
<220> FEATURE:
<223> OTHER INFORMATION: Q62E10 CDR3

<400> SEQUENCE: 17

Thr Gln Asn Gly Ala Ala
1               5

<210> SEQ ID NO 18
<211> LENGTH: 30
<212> TYPE: PRT
<213> ORGANISM: Artificial Sequence
<220> FEATURE:
<223> OTHER INFORMATION: Q62E10 FR1

<400> SEQUENCE: 18

Gln Val Gln Leu Val Glu Ser Gly Gly Gly Leu Val Gln Pro Gly Gly
1               5                   10                  15

```
Ser Leu Arg Leu Ser Cys Thr Thr Ser Gly Leu Asp Phe Gly
            20                  25                  30
```

<210> SEQ ID NO 19
<211> LENGTH: 14
<212> TYPE: PRT
<213> ORGANISM: Artificial Sequence
<220> FEATURE:
<223> OTHER INFORMATION: Q62E10 FR2

<400> SEQUENCE: 19

```
Trp Phe Arg Gln Ala Pro Gly Lys Glu Leu Glu Trp Val Ala
1               5                   10
```

<210> SEQ ID NO 20
<211> LENGTH: 32
<212> TYPE: PRT
<213> ORGANISM: Artificial Sequence
<220> FEATURE:
<223> OTHER INFORMATION: Q62E10 FR3

<400> SEQUENCE: 20

```
Arg Phe Thr Ile Ser Arg Asp Asn Ala Lys Asn Thr Leu Phe Leu Gln
1               5                   10                  15

Met Asn Asp Leu Lys Ser Glu Asp Thr Ala Val Tyr Tyr Cys Ser Asn
            20                  25                  30
```

<210> SEQ ID NO 21
<211> LENGTH: 11
<212> TYPE: PRT
<213> ORGANISM: Artificial Sequence
<220> FEATURE:
<223> OTHER INFORMATION: Q62E10 FR4

<400> SEQUENCE: 21

```
Lys Gly Gln Gly Val Gln Val Thr Val Ser Ser
1               5                   10
```

<210> SEQ ID NO 22
<211> LENGTH: 115
<212> TYPE: PRT
<213> ORGANISM: Artificial Sequence
<220> FEATURE:
<223> OTHER INFORMATION: Q62E10

<400> SEQUENCE: 22

```
Gln Val Gln Leu Val Glu Ser Gly Gly Gly Leu Val Gln Pro Gly Gly
1               5                   10                  15

Ser Leu Arg Leu Ser Cys Thr Thr Ser Gly Leu Asp Phe Gly Ile His
            20                  25                  30

Trp Met Tyr Trp Phe Arg Gln Ala Pro Gly Lys Glu Leu Glu Trp Val
        35                  40                  45

Ala Glu Ile Asn Thr Asn Ala Leu Ile Thr Lys Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Asp Leu Lys Ser Glu Asp Thr Ala Val Tyr Tyr Cys
                85                  90                  95

Ser Asn Thr Gln Asn Gly Ala Ala Lys Gly Gln Gly Val Gln Val Thr
            100                 105                 110

Val Ser Ser
        115
```

```
<210> SEQ ID NO 23
<211> LENGTH: 115
<212> TYPE: PRT
<213> ORGANISM: Artificial Sequence
<220> FEATURE:
<223> OTHER INFORMATION: Q65F2

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser His
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Ser Tyr Val Asp Ser Val
    50                  55                  60

Lys Gly Arg Phe Thr Val Ser Arg Asp Asn Ala Ala Asn Thr Leu Tyr
65                  70                  75                  80

Leu Glu Met Thr Ser Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115

<210> SEQ ID NO 24
<211> LENGTH: 115
<212> TYPE: PRT
<213> ORGANISM: Artificial Sequence
<220> FEATURE:
<223> OTHER INFORMATION: Q65F3

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser His
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Ile Asp Ser Val
    50                  55                  60

Arg Gly Arg Phe Thr Ala Ser Arg Asp Asn Ala Ala Asn Thr Leu Tyr
65                  70                  75                  80

Leu Glu Met Thr Asn Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115

<210> SEQ ID NO 25
<211> LENGTH: 115
<212> TYPE: PRT
<213> ORGANISM: Artificial Sequence
<220> FEATURE:
<223> OTHER INFORMATION: Q62F2

<400> SEQUENCE: 25

Gln Val Gln Leu Val Glu Ser Gly Gly Gly Leu Val Gln Pro Gly Gly
```

```
                1               5                   10                  15
Ser Leu Arg Leu Ser Cys Ala Ala Ser Gly Phe Asp Phe Asn Ser His
                20                  25                  30

Trp Met Tyr Trp Val Arg Gln Ala Pro Gly Lys Gly Leu Glu Trp Val
            35                  40                  45

Ser Glu Ile Asn Thr Asn Gly Leu Ile Thr Asn Tyr Val Asp Ser Val
        50                  55                  60

Lys Gly Arg Phe Thr Val Ser Arg Asp Asn Ala Ala Asn Thr Leu Tyr
65                  70                  75                  80

Leu Glu Met Thr Ser Leu Lys Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115
```

<210> SEQ ID NO 26
<211> LENGTH: 115
<212> TYPE: PRT
<213> ORGANISM: Artificial Sequence
<220> FEATURE:
<223> OTHER INFORMATION: Q65G1

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Asp Phe Tyr Ser His
                20                  25                  30

Trp Met Tyr Trp Val Arg Gln Ala Pro Gly Lys Gly Leu Glu Trp Val
            35                  40                  45

Ser Glu Ile Asn Thr Asn Gly Leu Ile Thr Lys Tyr Ile Asp Ser Val
        50                  55                  60

Arg Gly Arg Phe Thr Val Ser Arg Asp Asn Ala Ala Asn Thr Leu Tyr
65                  70                  75                  80

Leu Glu Met Thr Asn Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115
```

<210> SEQ ID NO 27
<211> LENGTH: 115
<212> TYPE: PRT
<213> ORGANISM: Artificial Sequence
<220> FEATURE:
<223> OTHER INFORMATION: Q65H6

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Asp Phe Tyr Ser His
                20                  25                  30

Trp Met Tyr Trp Val Arg Gln Ala Pro Gly Lys Gly Leu Glu Trp Val
            35                  40                  45

Ser Glu Ile Asn Thr Asn Gly Leu Ile Thr Lys Tyr Ile Asp Ser Val
        50                  55                  60
```

```
Arg Gly Arg Phe Thr Val Ser Arg Asp Asn Ala Ala Asn Thr Leu Tyr
 65                  70                  75                  80

Leu Glu Met Thr Asn Leu Glu Pro Glu Asp Thr Ala Leu Tyr Tyr Cys
                 85                  90                  95

Ala Arg Asn Gln Lys Gly Leu Asn Lys Gly Gln Gly Thr Gln Val Thr
            100                 105                 110

Val Ser Ser
        115

<210> SEQ ID NO 28
<211> LENGTH: 115
<212> TYPE: PRT
<213> ORGANISM: Artificial Sequence
<220> FEATURE:
<223> OTHER INFORMATION: Q65F1

<400> SEQUENCE: 28

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Phe Gly Val His
             20                  25                  30

Trp Met Tyr Trp Val Arg Gln Ala Pro Gly Lys Gly Leu Glu Trp Val
         35                  40                  45

Ser Glu Ile Asn Thr Asn Gly Leu Ile Thr Lys Tyr Ile Asp Ser Val
 50                  55                  60

Gly Gly Arg Phe Thr Val Ser Arg Asp Asn Ala Ala Asn Arg Leu Tyr
 65                  70                  75                  80

Leu Glu Met Thr Asn Leu Glu Pro Glu Asp Thr Ala Leu Tyr Tyr Cys
                 85                  90                  95

Ala Arg Asn Gln Met Gly Leu Asn Lys Gly Gln Gly Thr Gln Val Thr
            100                 105                 110

Val Ser Ser
        115

<210> SEQ ID NO 29
<211> LENGTH: 115
<212> TYPE: PRT
<213> ORGANISM: Artificial Sequence
<220> FEATURE:
<223> OTHER INFORMATION: Q65D1

<400> SEQUENCE: 29

Glu Val Gln Leu Val Glu Ser Gly Gly Gly Leu Val Gln Pro Gly Gly
  1               5                  10                  15

Ser Leu Arg Leu Ser Cys Thr Ala Ser Gly Phe Asp Phe Asp Asn His
             20                  25                  30

Trp Met Cys Trp Val Arg Gln Ala Pro Gly Lys Gly Leu Glu Trp Val
         35                  40                  45

Ser Glu Ile Asn Thr Asn Gly Leu Ile Thr Lys Tyr Ala Asp Phe Val
 50                  55                  60

Lys Gly Arg Phe Thr Val Ser Arg Asp Asn Ala Ala Asn Thr Leu Tyr
 65                  70                  75                  80

Leu Gln Ile Thr Arg Leu Lys Pro Glu Asp Thr Ala Leu Tyr Tyr Cys
                 85                  90                  95

Ala Arg Asn Gln Lys Gly Leu Asn Lys Gly Gln Gly Thr Gln Val Thr
            100                 105                 110

Val Ser Ser
        115
```

<210> SEQ ID NO 30
<211> LENGTH: 115
<212> TYPE: PRT
<213> ORGANISM: Artificial Sequence
<220> FEATURE:
<223> OTHER INFORMATION: Q65C7

<400> SEQUENCE: 30

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Asp Phe Ser Ser His
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Ala Asp Phe Val
    50                  55                  60

Lys Gly Arg Phe Thr Val Ser Arg Asp Asn Ala Ala Asn Thr Leu Tyr
65                  70                  75                  80

Leu Glu Ile Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115
```

<210> SEQ ID NO 31
<211> LENGTH: 115
<212> TYPE: PRT
<213> ORGANISM: Artificial Sequence
<220> FEATURE:
<223> OTHER INFORMATION: Q65D3

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Asp Phe Ser Ser His
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Ala Asp Ser Thr
    50                  55                  60

Lys Gly Arg Phe Thr Val Ser Arg Asp Asn Ala Ala Asn Met Leu Asn
65                  70                  75                  80

Leu Glu Met Thr Ser Leu Glu Pro Glu Asp Thr Ala Leu Tyr Tyr Cys
                85                  90                  95

Ala Arg Asn Glu Arg Gly Leu Asn Lys Gly Gln Gly Thr Gln Val Thr
            100                 105                 110

Val Ser Ser
        115
```

<210> SEQ ID NO 32
<211> LENGTH: 115
<212> TYPE: PRT
<213> ORGANISM: Artificial Sequence
<220> FEATURE:
<223> OTHER INFORMATION: Q65B1

<400> SEQUENCE: 32

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60

Lys Gly Arg Phe Thr Val Ser Arg Asn Asn Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
                100                 105                 110

Val Ser Ser
        115

<210> SEQ ID NO 33
<211> LENGTH: 115
<212> TYPE: PRT
<213> ORGANISM: Artificial Sequence
<220> FEATURE:
<223> OTHER INFORMATION: Q65F6

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Asp Phe Gly Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr Leu Tyr Ser Asp Ser Val
    50                  55                  60

Arg Gly Arg Phe Thr Ala Ser Arg Asp Asn Ala Asn Asn Ala Leu Phe
65                  70                  75                  80

Leu Gln Met Asn Asp Leu Lys Phe Glu Asp Thr Ala Val Tyr Tyr Cys
                85                  90                  95

Ala Lys Ser Arg Asn Gly Ala Ala Lys Gly Gln Gly Thr Gln Val Thr
                100                 105                 110

Val Ser Ser
        115

<210> SEQ ID NO 34
<211> LENGTH: 115
<212> TYPE: PRT
<213> ORGANISM: Artificial Sequence
<220> FEATURE:
<223> OTHER INFORMATION: Q65F11

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Asp Phe Gly Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr Leu Tyr Ser Asp Ser Val
    50                  55                  60

Arg Gly Arg Phe Thr Ala Ser Arg Asp Asn Ala Asn Ala Leu Phe
65                  70                  75                  80

Leu Gln Met Asn Asp Leu Lys Phe Glu Asp Thr Ala Val Tyr Tyr Cys
                85                  90                  95

Ala Lys Ser Arg Asn Gly Ala Ala Lys Gly Gln Gly Thr Gln Val Thr
            100                 105                 110

Val Ser Ser
        115

<210> SEQ ID NO 35
<211> LENGTH: 115
<212> TYPE: PRT
<213> ORGANISM: Artificial Sequence
<220> FEATURE:
<223> OTHER INFORMATION: Q65E12

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Asp Phe Ser Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr Leu Tyr Ala Asp Ser Val
    50                  55                  60

Lys Gly Arg Phe Thr Ala Ser Arg Asp Asn Lys Asn Ala Leu Phe
65                  70                  75                  80

Leu Gln Met Asn Asp Leu Lys Phe Glu Asp Thr Ala Val Tyr Tyr Cys
                85                  90                  95

Ala Lys Ser Arg Asn Gly Ala Ala Gly Gly Gln Gly Thr Gln Val Thr
            100                 105                 110

Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: Q65C12

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Pro Phe Asp Ile His
            20                  25                  30

Trp Met Tyr Trp Val Arg Gln Ala Pro Gly Lys Glu Leu Glu Trp Val
        35                  40                  45

Ala Glu Ile Asn Thr Asn Ala Leu Ile Thr Thr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Asp Leu Lys Phe Glu Asp Thr Ala Val Tyr Tyr Cys
                85                  90                  95

Thr His Ser Arg Asn Gly Ala Ala Lys Gly Gln Gly Thr Gln Val Thr
            100                 105                 110

Val Ser Ser

```
<210> SEQ ID NO 37
<211> LENGTH: 115
<212> TYPE: PRT
<213> ORGANISM: Artificial Sequence
<220> FEATURE:
<223> OTHER INFORMATION: Q65A6

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Thr Ala Ser Gly Leu Asp Phe Gly Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr His Tyr Thr Asp Ser Val
    50                  55                  60

Ser Gly Arg Phe Thr Ile Ser Arg Asp Asn Ala Lys Asn Thr Leu Phe
65                  70                  75                  80

Leu Gln Met Asn Asp Leu Lys Phe Glu Asp Thr Ala Val Tyr Ala Cys
                85                  90                  95

Ala Thr Ser Arg Asn Gly Ala Ala Lys Gly Gln Gly Thr Gln Val Thr
            100                 105                 110

Val Ser Ser
        115

<210> SEQ ID NO 38
<211> LENGTH: 115
<212> TYPE: PRT
<213> ORGANISM: Artificial Sequence
<220> FEATURE:
<223> OTHER INFORMATION: Q65A3

<400> SEQUENCE: 38

Glu Val Gln Leu Val Glu Ser Gly Gly Gly Leu Val Gln Pro Gly Gly
1               5                   10                  15

Ser Leu Arg Pro Ser Cys Thr Thr Ser Gly Leu Asp Phe Gly Ile His
            20                  25                  30

Trp Met Tyr Trp Phe Arg Gln Ala Pro Gly Lys Glu Leu Glu Trp Val
        35                  40                  45

Ala Glu Ile Asn Thr Asn Ala Leu Ile Thr Lys Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Asp Leu Lys Ser Glu Asp Thr Ala Val Tyr Tyr Cys
                85                  90                  95

Ser Asn Thr Gln Asn Gly Ala Ala Lys Gly Gln Gly Val Gln Val Thr
            100                 105                 110

Val Ser Ser
        115

<210> SEQ ID NO 39
<211> LENGTH: 115
<212> TYPE: PRT
<213> ORGANISM: Artificial Sequence
<220> FEATURE:
<223> OTHER INFORMATION: Q62F10

<400> SEQUENCE: 39
```

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Asp Phe Asn Ile His
            20                  25                  30

Trp Met Tyr Trp Val Arg Gln Ala Pro Gly Lys Glu Leu Glu Trp Val
        35                  40                  45

Ala Glu Ile Asn Thr Asn Gly Leu Ile Thr Val Tyr Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Asn Leu Lys Phe Glu Asp Thr Ala Val Tyr Tyr Cys
            85                  90                  95

Thr Asn Thr Gln Asn Gly Lys Thr Lys Gly Gln Gly Thr Gln Val Thr
            100                 105                 110

Val Ser Ser
        115

<210> SEQ ID NO 40
<211> LENGTH: 124
<212> TYPE: PRT
<213> ORGANISM: Artificial Sequence
<220> FEATURE:
<223> OTHER INFORMATION: Q62F11

<400> SEQUENCE: 40

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Val Met Gly Trp Phe Arg Gln Ala Pro Gly Lys Glu Arg Glu Phe Val
        35                  40                  45

Gly Phe Ile Arg Trp Asp Gly Leu Val Thr Arg Tyr Ala Asp Ala Val
    50                  55                  60

Lys Gly Arg Phe Thr Ile Ser Arg Asp Asn Ala Arg Asn Thr Leu Ser
65                  70                  75                  80

Leu Gln Thr Ile Gly Leu Leu Ala Glu Asp Thr Ala Val Tyr Tyr Cys
            85                  90                  95

Ala Ala Ser Gly Gly Gly Ser Gly Pro Val Asn Ala Gly Ser Tyr Glu
            100                 105                 110

Tyr Trp Gly Gln Gly Thr Gln Val Thr Val Ser Ser
        115                 120

<210> SEQ ID NO 41
<211> LENGTH: 115
<212> TYPE: PRT
<213> ORGANISM: Artificial Sequence
<220> FEATURE:
<223> OTHER INFORMATION: ID7F-EV

<400> SEQUENCE: 41

Glu Val Gln Leu Val Glu Ser Gly Gly Gly Leu Val Gln Pro Gly Ala
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
```

```
                    50                  55                  60
Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                    85                  90                  95

Ala Arg Asn Gln Lys Gly Leu Asn Lys Gly Gln Gly Thr Gln Val Thr
                   100                 105                 110

Val Ser Ser
        115

<210> SEQ ID NO 42
<211> LENGTH: 115
<212> TYPE: PRT
<213> ORGANISM: Artificial Sequence
<220> FEATURE:
<223> OTHER INFORMATION: ID8F-EV

<400> SEQUENCE: 42

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Asp Phe Ser Ser His
                 20                  25                  30

Trp Met Tyr Trp Val Arg Gln Ala Pro Gly Lys Glu Leu Glu Trp Leu
             35                  40                  45

Ser Glu Ile Asn Thr Asn Gly Leu Ile Thr His Tyr Gly Asp Ser Val
         50                  55                  60

Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                    85                  90                  95

Ala Arg Asn Gln Lys Gly Leu Asn Lys Gly Gln Gly Thr Gln Val Thr
                   100                 105                 110

Val Ser Ser
        115

<210> SEQ ID NO 43
<211> LENGTH: 115
<212> TYPE: PRT
<213> ORGANISM: Artificial Sequence
<220> FEATURE:
<223> OTHER INFORMATION: ID9F-EV

<400> SEQUENCE: 43

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Asp Phe Ser Ser His
                 20                  25                  30

Trp Met Tyr Trp Val Arg Gln Ala Pro Gly Lys Glu Leu Glu Trp Leu
             35                  40                  45

Ser Glu Ile Asn Thr Asn Gly Leu Ile Thr Lys Tyr Gly Asp Ser Val
         50                  55                  60

His Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                    85                  90                  95

Ala Arg Asn Gln Lys Gly Leu Asn Lys Gly Gln Gly Thr Gln Val Thr
                   100                 105                 110
```

Val Ser Ser
    115

<210> SEQ ID NO 44
<211> LENGTH: 115
<212> TYPE: PRT
<213> ORGANISM: Artificial Sequence
<220> FEATURE:
<223> OTHER INFORMATION: ID13F-EV

<400> SEQUENCE: 44

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser
    115

<210> SEQ ID NO 45
<211> LENGTH: 115
<212> TYPE: PRT
<213> ORGANISM: Artificial Sequence
<220> FEATURE:
<223> OTHER INFORMATION: ID14F-EV

<400> SEQUENCE: 45

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn His Gly Gln Gly Thr Gln Val Thr
            100                 105                 110

Val Ser Ser
    115

<210> SEQ ID NO 46
<211> LENGTH: 115
<212> TYPE: PRT
<213> ORGANISM: Artificial Sequence
<220> FEATURE:
<223> OTHER INFORMATION: ID15F-EV

```
<400> SEQUENCE: 46

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn His Gly Gln Gly Thr Gln Val Thr
            100                 105                 110

Val Ser Ser
        115

<210> SEQ ID NO 47
<211> LENGTH: 260
<212> TYPE: PRT
<213> ORGANISM: Artificial Sequence
<220> FEATURE:
<223> OTHER INFORMATION: ID22F

<400> SEQUENCE: 47

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser Gly Gly Gly Ser Gly Gly Gly Ser Gly Gly
        115                 120                 125

Gly Ser Gly Gly Gly Ser Gly Gly Gly Ser Gly Gly Gly
        130                 135                 140

Ser Glu Val Gln Leu Val Glu Ser Gly Gly Gly Leu Val Gln Pro Gly
145                 150                 155                 160

Gly Ser Leu Lys Leu Ser Cys Ala Ala Ser Gly Phe Asp Phe Ser Ser
                165                 170                 175

His Trp Met Tyr Trp Val Arg Gln Ala Pro Gly Lys Glu Leu Glu Trp
            180                 185                 190

Leu Ser Glu Ile Asn Thr Asn Gly Leu Ile Thr Lys Tyr Gly Asp Ser
        195                 200                 205

Val Lys Gly Arg Phe Thr Val Ser Arg Asn Asn Ala Ala Asn Lys Met
    210                 215                 220

Tyr Leu Glu Leu Thr Arg Leu Glu Pro Glu Asp Thr Ala Leu Tyr Tyr
```

-continued

```
                225                 230                 235                 240
Cys Ala Arg Asn Gln Lys Gly Leu Asn Lys Gly Gln Gly Thr Gln Val
                    245                 250                 255

Thr Val Ser Ser
            260

<210> SEQ ID NO 48
<211> LENGTH: 260
<212> TYPE: PRT
<213> ORGANISM: Artificial Sequence
<220> FEATURE:
<223> OTHER INFORMATION: ID23F

<400> SEQUENCE: 48

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Glu Val Gln Leu Val Glu Ser Gly Gly Gly Leu Val Gln Pro Gly
145                 150                 155                 160

Gly Ser Leu Lys Leu Ser Cys Ala Ala Ser Gly Phe Asp Phe Ser Ser
                165                 170                 175

His Trp Met Tyr Trp Val Arg Gln Ala Pro Gly Lys Glu Leu Glu Trp
            180                 185                 190

Leu Ser Glu Ile Asn Thr Asn Gly Leu Ile Thr His Tyr Gly Asp Ser
        195                 200                 205

Val Lys Gly Arg Phe Thr Val Ser Arg Asn Asn Ala Ala Asn Lys Met
    210                 215                 220

Tyr Leu Glu Leu Thr Arg Leu Glu Pro Glu Asp Thr Ala Leu Tyr Tyr
225                 230                 235                 240

Cys Ala Arg Asn Gln Lys Gly Leu Asn Lys Gly Gln Gly Thr Gln Val
                245                 250                 255

Thr Val Ser Ser
            260

<210> SEQ ID NO 49
<211> LENGTH: 260
<212> TYPE: PRT
<213> ORGANISM: Artificial Sequence
<220> FEATURE:
<223> OTHER INFORMATION: ID24F

<400> SEQUENCE: 49
```

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
            35                  40                  45

Ser Glu Ile Asn Thr Asn Gly Leu Ile Thr His Tyr Gly Asp Ser Val
50                  55                  60

Lys Gly Arg Phe Thr Val Ser Arg Asn Asn Ala Ala Asn Ser Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser Gly Gly Gly Gly Ser Gly Gly Gly Gly Ser Gly Gly Gly
            115                 120                 125

Gly Ser Gly Gly Gly Gly Ser Gly Gly Gly Gly Ser Gly Gly Gly Gly
            130                 135                 140

Ser Glu Val Gln Leu Val Glu Ser Gly Gly Gly Leu Val Gln Pro Gly
145                 150                 155                 160

Gly Ser Leu Lys Leu Ser Cys Ala Ala Ser Gly Phe Asp Phe Ser Ser
            165                 170                 175

His Trp Met Tyr Trp Val Arg Gln Ala Pro Gly Lys Glu Leu Glu Trp
                180                 185                 190

Leu Ser Glu Ile Asn Thr Asn Gly Leu Ile Thr His Tyr Gly Asp Ser
            195                 200                 205

Val Lys Gly Arg Phe Thr Val Ser Arg Asn Asn Ala Ala Asn Ser Met
            210                 215                 220

Tyr Leu Glu Leu Thr Arg Leu Glu Pro Glu Asp Thr Ala Leu Tyr Tyr
225                 230                 235                 240

Cys Ala Arg Asn Gln Lys Gly Leu Asn Lys Gly Gln Gly Thr Gln Val
                245                 250                 255

Thr Val Ser Ser
            260

<210> SEQ ID NO 50
<211> LENGTH: 260
<212> TYPE: PRT
<213> ORGANISM: Artificial Sequence
<220> FEATURE:
<223> OTHER INFORMATION: ID25F

<400> SEQUENCE: 50

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
            35                  40                  45

Ser Glu Ile Asn Thr Asn Gly Leu Ile Thr His Tyr Gly Asp Ser Val
50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Glu Val Gln Leu Val Glu Ser Gly Gly Leu Val Gln Pro Gly
145                 150                 155                 160

Gly Ser Leu Lys Leu Ser Cys Ala Ala Ser Gly Phe Asp Phe Ser Ser
                165                 170                 175

His Trp Met Tyr Trp Val Arg Gln Ala Pro Gly Lys Glu Leu Glu Trp
            180                 185                 190

Leu Ser Glu Ile Asn Thr Asn Gly Leu Ile Thr His Tyr Gly Asp Ser
        195                 200                 205

Val Lys Gly Arg Phe Thr Val Ser Arg Asn Asn Ala Ala Asn Lys Met
    210                 215                 220

Tyr Leu Glu Leu Thr Arg Leu Glu Pro Glu Asp Thr Ala Leu Tyr Tyr
225                 230                 235                 240

Cys Ala Arg Asn Gln His Gly Leu Asn Lys Gly Gln Gly Thr Gln Val
                245                 250                 255

Thr Val Ser Ser
            260

<210> SEQ ID NO 51
<211> LENGTH: 260
<212> TYPE: PRT
<213> ORGANISM: Artificial Sequence
<220> FEATURE:
<223> OTHER INFORMATION: ID26F

<400> SEQUENCE: 51

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Ser Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Glu Val Gln Leu Val Glu Ser Gly Gly Leu Val Gln Pro Gly
145                 150                 155                 160

Gly Ser Leu Lys Leu Ser Cys Ala Ala Ser Gly Phe Asp Phe Ser Ser
                165                 170                 175

His Trp Met Tyr Trp Val Arg Gln Ala Pro Gly Lys Glu Leu Glu Trp
            180                 185                 190

```
Leu Ser Glu Ile Asn Thr Asn Gly Leu Ile Thr His Tyr Gly Asp Ser
            195                 200                 205

Val Lys Gly Arg Phe Thr Val Ser Arg Asn Asn Ala Ala Asn Ser Met
    210                 215                 220

Tyr Leu Glu Leu Thr Arg Leu Glu Pro Glu Asp Thr Ala Leu Tyr Tyr
225                 230                 235                 240

Cys Ala Arg Asn Gln His Gly Leu Asn Lys Gly Gln Gly Thr Gln Val
                245                 250                 255

Thr Val Ser Ser
            260

<210> SEQ ID NO 52
<211> LENGTH: 260
<212> TYPE: PRT
<213> ORGANISM: Artificial Sequence
<220> FEATURE:
<223> OTHER INFORMATION: ID27F

<400> SEQUENCE: 52

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

His Gly Arg Phe Thr Val Ser Arg Asn Asn Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Glu Val Gln Leu Val Glu Ser Gly Gly Gly Leu Val Gln Pro Gly
145                 150                 155                 160

Gly Ser Leu Lys Leu Ser Cys Ala Ala Ser Gly Phe Asp Phe Ser Ser
                165                 170                 175

His Trp Met Tyr Trp Val Arg Gln Ala Pro Gly Lys Glu Leu Glu Trp
            180                 185                 190

Leu Ser Glu Ile Asn Thr Asn Gly Leu Ile Thr His Tyr Gly Asp Ser
        195                 200                 205

Val His Gly Arg Phe Thr Val Ser Arg Asn Asn Ala Ala Asn Lys Met
    210                 215                 220

Tyr Leu Glu Leu Thr Arg Leu Glu Pro Glu Asp Thr Ala Leu Tyr Tyr
225                 230                 235                 240

Cys Ala Arg Asn Gln Lys Gly Leu Asn Lys Gly Gln Gly Thr Leu Val
                245                 250                 255

Thr Val Ser Ser
            260

<210> SEQ ID NO 53
<211> LENGTH: 260
```

```
<212> TYPE: PRT
<213> ORGANISM: Artificial Sequence
<220> FEATURE:
<223> OTHER INFORMATION: ID28F

<400> SEQUENCE: 53

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60

His Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Glu Val Gln Leu Val Glu Ser Gly Gly Gly Leu Val Gln Pro Gly
145                 150                 155                 160

Gly Ser Leu Lys Leu Ser Cys Ala Ala Ser Gly Phe Asp Phe Ser Ser
                165                 170                 175

His Trp Met Tyr Trp Val Arg Gln Ala Pro Gly Lys Glu Leu Glu Trp
            180                 185                 190

Leu Ser Glu Ile Asn Thr Asn Gly Leu Ile Thr Lys Tyr Gly Asp Ser
        195                 200                 205

Val His Gly Arg Phe Thr Val Ser Arg Asn Asn Ala Ala Asn Lys Met
    210                 215                 220

Tyr Leu Glu Leu Thr Arg Leu Glu Pro Glu Asp Thr Ala Leu Tyr Tyr
225                 230                 235                 240

Cys Ala Arg Asn Gln Lys Gly Leu Asn Lys Gly Gln Gly Thr Gln Val
                245                 250                 255

Thr Val Ser Ser
            260

<210> SEQ ID NO 54
<211> LENGTH: 260
<212> TYPE: PRT
<213> ORGANISM: Artificial Sequence
<220> FEATURE:
<223> OTHER INFORMATION: ID29F

<400> SEQUENCE: 54

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
    50                  55                  60
```

-continued

His Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
130                 135                 140

Ser Glu Val Gln Leu Val Glu Ser Gly Gly Gly Leu Val Gln Pro Gly
145                 150                 155                 160

Gly Ser Leu Lys Leu Ser Cys Ala Ala Ser Gly Phe Asp Phe Ser Ser
                165                 170                 175

His Trp Met Tyr Trp Val Arg Gln Ala Pro Gly Lys Glu Leu Glu Trp
            180                 185                 190

Leu Ser Glu Ile Asn Thr Asn Gly Leu Ile Thr Lys Tyr Gly Asp Ser
        195                 200                 205

Val His Gly Arg Phe Thr Val Ser Arg Asn Asn Ala Ala Asn Lys Met
    210                 215                 220

Tyr Leu Glu Leu Thr Arg Leu Glu Pro Glu Asp Thr Ala Leu Tyr Tyr
225                 230                 235                 240

Cys Ala Arg Asn Gln His Gly Leu Asn Lys Gly Gln Gly Thr Gln Val
                245                 250                 255

Thr Val Ser Ser
            260

<210> SEQ ID NO 55
<211> LENGTH: 115
<212> TYPE: PRT
<213> ORGANISM: Artificial Sequence
<220> FEATURE:
<223> OTHER INFORMATION: Q62E10-DVQLV

<400> SEQUENCE: 55

Asp Val Gln Leu Val Glu Ser Gly Gly Gly Leu Val Gln Pro Gly Gly
1               5                   10                  15

Ser Leu Arg Leu Ser Cys Thr Thr Ser Gly Leu Asp Phe Gly Ile His
            20                  25                  30

Trp Met Tyr Trp Phe Arg Gln Ala Pro Gly Lys Glu Leu Glu Trp Val
        35                  40                  45

Ala Glu Ile Asn Thr Asn Ala Leu Ile Thr Lys Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Asp Leu Lys Ser Glu Asp Thr Ala Val Tyr Tyr Cys
                85                  90                  95

Ser Asn Thr Gln Asn Gly Ala Ala Lys Gly Gln Gly Val Gln Val Thr
            100                 105                 110

Val Ser Ser
        115

<210> SEQ ID NO 56
<211> LENGTH: 115
<212> TYPE: PRT
<213> ORGANISM: Artificial Sequence

```
<220> FEATURE:
<223> OTHER INFORMATION: ID34F

<400> SEQUENCE: 56

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser
        115

<210> SEQ ID NO 57
<211> LENGTH: 115
<212> TYPE: PRT
<213> ORGANISM: Artificial Sequence
<220> FEATURE:
<223> OTHER INFORMATION: ID37F

<400> SEQUENCE: 57

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
            100                 105                 110

Val Ser Ser
        115

<210> SEQ ID NO 58
<211> LENGTH: 28
<212> TYPE: DNA
<213> ORGANISM: Artificial Sequence
<220> FEATURE:
<223> OTHER INFORMATION: 3' Primer with Spe site

<400> SEQUENCE: 58
tcttaactag tgaggagacg gtgacctg                                              28

<210> SEQ ID NO 59
<211> LENGTH: 5
<212> TYPE: PRT
```

```
<213> ORGANISM: Artificial Sequence
<220> FEATURE:
<223> OTHER INFORMATION: Q65F1 CDR1

<400> SEQUENCE: 59

Val His Trp Met Tyr
1               5

<210> SEQ ID NO 60
<211> LENGTH: 5
<212> TYPE: PRT
<213> ORGANISM: Artificial Sequence
<220> FEATURE:
<223> OTHER INFORMATION: Q65D1 CDR1

<400> SEQUENCE: 60

Asn His Trp Met Cys
1               5

<210> SEQ ID NO 61
<211> LENGTH: 17
<212> TYPE: PRT
<213> ORGANISM: Artificial Sequence
<220> FEATURE:
<223> OTHER INFORMATION: ID27F CDR2

<400> SEQUENCE: 61

Glu Ile Asn Thr Asn Gly Leu Ile Thr His Tyr Gly Asp Ser Val His
1               5                   10                  15

Gly

<210> SEQ ID NO 62
<211> LENGTH: 17
<212> TYPE: PRT
<213> ORGANISM: Artificial Sequence
<220> FEATURE:
<223> OTHER INFORMATION: ID28F CDR2

<400> SEQUENCE: 62

Glu Ile Asn Thr Asn Gly Leu Ile Thr Lys Tyr Gly Asp Ser Val His
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: Q65F2 CDR2

<400> SEQUENCE: 63

Glu Ile Asn Thr Asn Gly Leu Ile Thr Ser Tyr Val Asp Ser Val Lys
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Q65F3 CDR2

<400> SEQUENCE: 64

Glu Ile Asn Thr Asn Gly Leu Ile Thr Lys Tyr Ile Asp Ser Val Arg
1               5                   10                  15
```

Gly

<210> SEQ ID NO 65
<211> LENGTH: 17
<212> TYPE: PRT
<213> ORGANISM: Artificial Sequence
<220> FEATURE:
<223> OTHER INFORMATION: Q62F2 CDR2

<400> SEQUENCE: 65

Glu Ile Asn Thr Asn Gly Leu Ile Thr Asn Tyr Val Asp Ser Val Lys
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: Q65F1 CDR2

<400> SEQUENCE: 66

Glu Ile Asn Thr Asn Gly Leu Ile Thr Lys Tyr Ile Asp Ser Val Gly
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: Q65D1 CDR2

<400> SEQUENCE: 67

Glu Ile Asn Thr Asn Gly Leu Ile Thr Lys Tyr Ala Asp Phe Val Lys
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Q65D3 CDR2

<400> SEQUENCE: 68

Glu Ile Asn Thr Asn Gly Leu Ile Thr Lys Tyr Ala Asp Ser Thr Lys
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: Q65B1 CDR2

<400> SEQUENCE: 69

Glu Ile Asn Thr Asn Gly Leu Ile Thr Lys Tyr Gly Asp Ser Val Lys
1               5                   10                  15

Gly

```
<210> SEQ ID NO 70
<211> LENGTH: 6
<212> TYPE: PRT
<213> ORGANISM: Artificial Sequence
<220> FEATURE:
<223> OTHER INFORMATION: Q65F2 CDR3

<400> SEQUENCE: 70

Asn Gln Lys Gly Leu Asn
1               5

<210> SEQ ID NO 71
<211> LENGTH: 6
<212> TYPE: PRT
<213> ORGANISM: Artificial Sequence
<220> FEATURE:
<223> OTHER INFORMATION: Q65F1 CDR3

<400> SEQUENCE: 71

Asn Gln Met Gly Leu Asn
1               5

<210> SEQ ID NO 72
<211> LENGTH: 6
<212> TYPE: PRT
<213> ORGANISM: Artificial Sequence
<220> FEATURE:
<223> OTHER INFORMATION: Q65D3 CDR3

<400> SEQUENCE: 72

Asn Glu Arg Gly Leu Asn
1               5

<210> SEQ ID NO 73
<211> LENGTH: 17
<212> TYPE: PRT
<213> ORGANISM: Artificial Sequence
<220> FEATURE:
<223> OTHER INFORMATION: Q65F6 CDR2

<400> SEQUENCE: 73

Glu Ile Asn Thr Asn Gly Leu Ile Thr Leu Tyr Ser Asp Ser Val Arg
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Q65F11 CDR2

<400> SEQUENCE: 74

Glu Ile Asn Thr Asn Gly Leu Ile Thr Leu Tyr Ala Asp Ser Val Lys
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: Q65C12 CDR2

<400> SEQUENCE: 75

Glu Ile Asn Thr Asn Ala Leu Ile Thr Thr Tyr Ala Asp Ser Val Lys
```

-continued

```
1               5                   10                  15

Gly

<210> SEQ ID NO 76
<211> LENGTH: 17
<212> TYPE: PRT
<213> ORGANISM: Artificial Sequence
<220> FEATURE:
<223> OTHER INFORMATION: Q65A6 CDR2

<400> SEQUENCE: 76

Glu Ile Asn Thr Asn Gly Leu Ile Thr His Tyr Thr Asp Ser Val Ser
1               5                   10                  15

Gly

<210> SEQ ID NO 77
<211> LENGTH: 17
<212> TYPE: PRT
<213> ORGANISM: Artificial Sequence
<220> FEATURE:
<223> OTHER INFORMATION: Q65A3 CDR2

<400> SEQUENCE: 77

Glu Ile Asn Thr Asn Ala Leu Ile Thr Lys Tyr Ala Asp Ser Val Lys
1               5                   10                  15

Gly

<210> SEQ ID NO 78
<211> LENGTH: 6
<212> TYPE: PRT
<213> ORGANISM: Artificial Sequence
<220> FEATURE:
<223> OTHER INFORMATION: Q65F6 CDR3

<400> SEQUENCE: 78

Ser Arg Asn Gly Ala Ala
1               5

<210> SEQ ID NO 79
<211> LENGTH: 6
<212> TYPE: PRT
<213> ORGANISM: Artificial Sequence
<220> FEATURE:
<223> OTHER INFORMATION: Q65F11 CDR3

<400> SEQUENCE: 79

Ala Arg Asn Gly Ala Ala
1               5

<210> SEQ ID NO 80
<211> LENGTH: 6
<212> TYPE: PRT
<213> ORGANISM: Artificial Sequence
<220> FEATURE:
<223> OTHER INFORMATION: Q62F10 CDR3

<400> SEQUENCE: 80

Thr Gln Asn Gly Lys Thr
1               5

<210> SEQ ID NO 81
<211> LENGTH: 17
<212> TYPE: DNA
<213> ORGANISM: Artificial Sequence
<220> FEATURE:
```

<223> OTHER INFORMATION: M13.rev

<400> SEQUENCE: 81
caggaaacag ctatgac                                                    17

<210> SEQ ID NO 82
<211> LENGTH: 16
<212> TYPE: DNA
<213> ORGANISM: Artificial Sequence
<220> FEATURE:
<223> OTHER INFORMATION: M13.fw

<400> SEQUENCE: 82
gtaaaacgac ggccag                                                     16

<210> SEQ ID NO 83
<211> LENGTH: 345
<212> TYPE: DNA
<213> ORGANISM: Artificial Sequence
<220> FEATURE:
<223> OTHER INFORMATION: Polynucleotide coding sequence of ID38F, codon
      optimised for yeast expression

<400> SEQUENCE: 83
gatgttcaat tggttgaatc tggtggtggt ttggttcaac caggtggttc tttgaaattg      60
tcttgtgctg cttctggttt cgatttctct tctcattgga gtactgggt tagacaagct     120 ccaggtaaag aattggaatg gttgtctgaa atcaacacca acggtttgat tacccattat    180
ggtgattctg tcaagggtag attcactgtc tctagaaaca atgctgctaa caagatgtac    240
ttggaattga ccagattgga accagaagat actgccttgt attactgcgc tagaaatcaa    300
catggtttga caaaggtca aggtactcaa gttaccgttt cctca                     345

<210> SEQ ID NO 84
<211> LENGTH: 345
<212> TYPE: DNA
<213> ORGANISM: Artificial Sequence
<220> FEATURE:
<223> OTHER INFORMATION: Polynucleotide coding sequence of Q62E10, codon
      optimised for yeast expression

<400> SEQUENCE: 84
caagtccaat tgcaagaatc tggtggtggt ttggttcaac caggtggttc tttgagattg      60
tcttgtacta cttctggttt ggatttcggt atccattgga tgtactggtt tagacaagct    120
ccaggtaaag aattggaatg ggttgctgaa atcaacacca atgctttgat taccaagtac    180
gccgattctg ttaagggtag attcaccatt tctagagata cgctaagaa caccttgttc     240 ttgcaaatga cgacttgaa gtctgaagat accgctgttt actactgttc taacactcaa     300
aatggtgctg ctaaaggtca aggtgtacaa gttactgttt cctcc                    345

<210> SEQ ID NO 85
<211> LENGTH: 345
<212> TYPE: DNA
<213> ORGANISM: Artificial Sequence
<220> FEATURE:
<223> OTHER INFORMATION: Polynucleotide coding sequence of ID38F, codon
      optimised for E. coli expression

<400> SEQUENCE: 85
gatgttcagc tggttgaaag cggtggtggt ctggttcagc ctggtggtag cctgaaactg      60
agctgtgcag caagcggttt tgattttagc agccattgga tgtattgggt tcgtcaggca    120

```
ccgggtaaag aactggaatg gctgagcgaa attaacacca atggtctgat tacccattat    180
ggcgatagcg ttaaaggtcg ttttaccgtt agccgtaata atgcagccaa caaaatgtat    240
ctggaactga cccgtctgga accggaagat accgcactgt attattgtgc acgtaatcag    300
catggtctga taaaggtca gggcacccag gttaccgtga gcagc                    345
```

<210> SEQ ID NO 86
<211> LENGTH: 345
<212> TYPE: DNA
<213> ORGANISM: Artificial Sequence
<220> FEATURE:
<223> OTHER INFORMATION: Polynucleotide coding sequence of Q62E10, codon optimised for E. coli expression

<400> SEQUENCE: 86

```
caggttcagc tgcaagaaag cggtggtggt ctggttcagc ctggtggtag cctgcgtctg    60
agctgtacca ccagtggtct ggattttggt attcattgga tgtattggtt cgtcaggca    120 ccgggtaaag aactggaatg ggttgcagaa attaacacca atgcactgat taccaaatat    180
gccgatagcg tgaaaggtcg ttttaccatt agccgtgata atgccaaaaa taccctgttt    240
ctgcagatga acgatctgaa aagcgaagat accgcagtgt attattgtag caataccccag    300 aatggtgcag caaaaggtca gggtgttcag gttaccgtta gcagc                    345
```

<210> SEQ ID NO 87
<211> LENGTH: 501
<212> TYPE: DNA
<213> ORGANISM: Artificial Sequence
<220> FEATURE:
<223> OTHER INFORMATION: Polynucleotide consisting of ID38F open reading frame for E. coli expression (PelB leader to c-myc-6His tag 2x stop codon)

<400> SEQUENCE: 87

```
atgaaatatc tgctgccgac cgcagcagcg ggtctgctgc tgctggcagc acagcctgca    60
atggcagatg ttcagctggt tgaaagcggt ggtggtctgg ttcagcctgg tggtagcctg    120
aaactgagct gtgcagcaag cggtttttgat tttagcagcc attggatgta ttgggttcgt    180
caggcaccgg gtaaagaact ggaatggctg agcgaaatta acaccaatgg tctgattacc    240
cattatggcg atagcgttaa aggtcgtttt accgttagcc gtaataatgc agccaacaaa    300
atgtatctgg aactgacccg tctggaaccg gaagataccg cactgtatta ttgtgcacgt    360
aatcagcatg gtctgaataa aggtcagggc acccaggtta ccgtgagcag cgcagcagcc    420
agcggtagcc tggaacagaa actgattagc gaagaggatc tgaatggtgc agcacatcat    480
catcaccatc atggtgccgc a                                              501
```

<210> SEQ ID NO 88
<211> LENGTH: 486
<212> TYPE: DNA
<213> ORGANISM: Artificial Sequence
<220> FEATURE:
<223> OTHER INFORMATION: Polynucleotide consisting of ID38F open reading frame for E. coli expression (PelB leader to Flag-6His tag 2xstop codon)

<400> SEQUENCE: 88

```
atgaaatacc tattgcctac ggcagccgct ggattgttat actcgcggcc cagccggcc    60 atggccgatg ttcagctggt tgaaagcggt ggtggtctgg ttcagcctgg tggtagcctg    120
aaactgagct gtgcagcaag cggtttttgat tttagcagcc attggatgta ttgggttcgt    180
```

```
caggcaccgg gtaaagaact ggaatggctg agcgaaatta acaccaatgg tctgattacc    240
cattatggcg atagcgttaa aggtcgtttt accgttagcc gtaataatgc agccaacaaa    300
atgtatctgg aactgacccg tctggaaccg gaagataccg cactgtatta ttgtgcacgt    360
aatcagcatg gtctgaataa aggtcagggc acccaggtca ccgtctcctc agcggccgca    420
gactacaaag acgacgacga caaagggggct gcacatcacc atcatcacca cggggctgca    480
taataa                                                                486
```